(12) United States Patent
Butt et al.

(10) Patent No.: US 7,655,413 B2
(45) Date of Patent: Feb. 2, 2010

(54) METHODS AND COMPOSITIONS FOR ENHANCED PROTEIN EXPRESSION AND PURIFICATION

(75) Inventors: Tauseef R. Butt, Audubon, PA (US); Oxana A. Malakhova, West Chester, PA (US); Michael P. Malakhov, West Chester, PA (US)

(73) Assignee: Lifesensors, Inc., Malvern, PA (US)

( * ) Notice: Subject to any disclaimer, the term of this patent is extended or adjusted under 35 U.S.C. 154(b) by 0 days.

(21) Appl. No.: 10/504,785

(22) PCT Filed: Jun. 28, 2004

(86) PCT No.: PCT/US2004/020778

§ 371 (c)(1),
(2), (4) Date: Nov. 15, 2005

(87) PCT Pub. No.: WO2005/003313

PCT Pub. Date: Jan. 13, 2005

(65) Prior Publication Data

US 2007/0037246 A1    Feb. 15, 2007

Related U.S. Application Data

(60) Provisional application No. 60/482,817, filed on Jun. 26, 2003.

(51) Int. Cl.
*G01N 33/53* (2006.01)
(52) U.S. Cl. ........................................ 435/7.1
(58) Field of Classification Search ............ None
See application file for complete search history.

(56) References Cited

U.S. PATENT DOCUMENTS

| | | | |
|---|---|---|---|
| 6,576,469 B1 | 6/2003 | Struhl | |
| 6,872,551 B2 | 3/2005 | Lima | |
| 7,220,576 B2 * | 5/2007 | Butt et al. | 435/320.1 |
| 2003/0086918 A1 * | 5/2003 | Lima et al. | 424/94.63 |

OTHER PUBLICATIONS

Ciechanover et al 1982 vol. 257 No. 5 pp. 2537-2542.*
Strous et al EP1356819A1 Date Oct. 29, 2003.*
Bowie et al (Science, 1990, 247:1306-1310).*
Varshavsky, A., "The N-end rule and regulation of apoptosis," Nature Cell Biology, 5:373-376, (2003).
Malakhov, M.P., et al., "SUMO fusions and SUMO-specific protease for efficient expression and purification of proteins," Journal of Structural and Functional Genomics, 5:75-86, (2004).
Johnsson, N., et al., "Splint ubiquitin as a sensor of protein interactions in vivo," Proc. Natl. Acad. Sci. U.S.A., 91:10340-10344, (1994).
Waldo, G.S., et al., "Rapid protein-folding assay using green fluorescent protein," Nature Biotechnology, 17:691-695, (1999).
Kapust, R.B., et al., "*Escherichia coli* maltose-binding protein is uncommonly effective at promoting the solubility of polypeptides to which it is fused," Protein Science, 8:1668-1674, (1999).
Ecker, D.J., et al., "Increasing Gene Expression in Yeast by Fusion to Ubiquitin," The Journal of Biological Chemistry, 264:7715-7719, (1989).
Butt, T.R., et al., "Ubiquitin fusion augments the yield of cloned gene products in *Escherichia coli*," Proc. Natl. Acad. Sci. U.S.A., 86:2540-2544, (1989).
Power, R.F., et al., "High level expression of a truncated chicken progesterone receptor . . . ," J. Biol. Chem., 265:1419-1424, (1990).
Johnsson, N., "A split-ubiquitin-based assay detects the influence of mutations on the conformational stability of . . . ," FEBS Letters, 531:259-264, (2002).
Baker, R.T., "Protein expression using ubiquitin fusion and cleavage", Current Opinion in Biotechnology, vol. 7: pp. 541-546, (1996).
Bayer, P., et al., "Structure Determination of the Small Ubiquitin-related Modifier SUMO-1", Journal of Molecular Biology, vol. 280: pp. 275-286 (1998).
Liu, Q., et al., "The Binding Interface between an E2 (UBC9) and a Ubiquitin Homologue (UBL1)", The Journal of Biological Chemistry, vol. 274: pp. 16979-16987, (1999).
Yeh, E.T.H., et al., "Ubiquitin-like proteins: new wines in new bottles," Gene, 248:1-14, (2000).
Varshavsky, A., "Ubiquitin Fusion Technique and its Descendants," Methods in Enzymology 327:578-593, (2000).
Saitoh, H., et al., "SUMO-1: wrestling with a new ubiquitin-related modifier," Trends Biochem. Sci., 22:374-6, (1997).
Johnson, E.S., et al., "The ubiquitin-like protein Smt3p is activated for conjugation . . . ," EMBO J., 16:5509-5519, (1997).
Tanaka, K., et al., "Characterization of a Fission Yeast SUMO-1 Homologue, Pmt3p, Required for . . . ", Molecular and Cellular Biology, 19:8660-8672, (1999).
Li, S-J, et al., "The Yeast ULLP2 (SMT4) Gene Encodes a Novel Protease Specific for . . . ", Molecular and Cellular Biology, 20:2367-2377, (2000).
Ichimura, Y., et al., "A ubiquitin-like system mediates protein lipidation," Nature, 408:488-492, (2000).
Li, S-J, et al., "A new protease required for cell-cycle progression in yeast," Nature, 398:246-251, (1999).
Mossessova, E., et al., "Ulp1-SUMO Cyrstal Structure and Genetic Analysis Reveal Conserved Interactions . . . ", Molecular Cell, 5:865-876, (2000).
Genebank Accession No. U37458 (Printed on Jul. 25, 2006).
Bachmair, et al., In vivo half-life of a protein is a function of its amino-terminal residue, Science 234:179-186, (1986).
pQE-30 Xa Vector, Qiagen product cataglog on the world wide web (2005).
Muller, S., et al., "Conjugation with the ubiquitin-related modifier SUMO-1 regulates the partioning of . . . ," EMBO J., 17:61-70, (1998).

* cited by examiner

*Primary Examiner*—Robert B Mondesi
*Assistant Examiner*—Nina A Archie
(74) *Attorney, Agent, or Firm*—Dann, Dorfman, Herrell & Skillman; Robert C. Netter, Jr.; Kathleen D. Rigaut

(57) ABSTRACT

Methods for enhancing expression levels and secretion of heterologous fusion proteins in a host cell are disclosed.

52 Claims, 42 Drawing Sheets

Amino acid sequence of mature SUMO protein; (SEQ ID NO: 1)
msdsevnqea kpevkpevkp ethinlkvsd gsseiffkik kttplrrlme
afakrqgkem dslrflydgi riqadqaped ldmedndiie ahreqigg Nucleotide sequence encoding mature SUMO protein; (SEQ ID NO: 2)
atg tcggactcag aagtcaatca agaagctaag ccagaggtca agccagaagt
caagcctgag actcacatca atttaaaggt gtccgatgga tcttcagaga
tcttcttcaa gatcaaaaag accactcctt taagaaggct gatggaagcg
ttcgctaaaa gacagggtaa ggaaatggac tccttaagat tcttgtacga
cggtattaga attcaagctg atcaggcccc tgaagatttg gacatggagg
ataacgatat tattgaggct cacagagaac agattggtgg t

Figure 12

Amino acid sequence of 6xHis-SUMO protein as it is encoded in pET-6xHis-SUMO, (SEQ ID NO: 3)
mghhhhhhgs dsevnqea kpevkpevkp ethinlkvsd gsseiffkik
kttplrrlme afakrqgkem dslrflydgi riqadqaped ldmedndiie
ahreqigg Nucleotide sequence of 6xHis-SUMO protein as it is encoded in pET-6xHis-SUMO, (SEQ ID NO: 4)
atgggtcatc accatcatca tcacggg tcggactcag aagtcaatca agaagctaag
ccagaggtca agccagaagt caagcctgag actcacatca atttaaaggt
gtccgatgga tcttcagaga tcttcttcaa gatcaaaaag accactcctt
taagaaggct gatggaagcg ttcgctaaaa gacagggtaa ggaaatggac
tccttaagat tcttgtacga cggtattaga attcaagctg atcaggcccc
tgaagatttg gacatggagg ataacgatat tattgaggct cacagagaac
agattggagg ttga

Figure 13A

```
        BglII
        ~~~~~~
  1  AGATCTCGATCCCGCGAAATTAATACGACTCACTATAGGGGAATTGTGAG

XbaI
            ~~~~~~
 51  CGGATAACAATTCCCCTCTAGAAATAATTTTGTTTAACTTTAAGAAGGAG

NcoI
         ~~~~~~
         MetGlyHisHisHisHisHisHisGlySerAspSerGluValA
101  ATATACCATGGGTCATCACCATCATCATCACGGGTCGGACTCAGAAGTCA snGlnGluAlaLysProGluValLysProGluValLysProGluThrHis
151  ATCAAGAAGCTAAGCCAGAGGTCAAGCCAGAAGTCAAGCCTGAGACTCAC

BglII
                                          ~~~~~~
     IleAsnLeuLysValSerAspGlySerSerGluIlePhePheLysIleLy
201  ATCAATTTAAAGGTGTCCGATGGATCTTCAGAGATCTTCTTCAAGATCAA sLysThrThrProLeuArgArgLeuMetGluAlaPheAlaLysArgGlnG
251  AAAGACCACTCCTTTAAGAAGGCTGATGGAAGCGTTCGCTAAAAGACAGG

EcoRI
                                               ~~~~~
     lyLysGluMetAspSerLeuArgPheLeuTyrAspGlyIleArgIleGln
301  GTAAGGAAATGGACTCCTTAAGATTCTTGTACGACGGTATTAGAATTCAA

AlaAspGlnAlaProGluAspLeuAspMetGluAspAsnAspIleIleGl
351  GCTGATCAGGCCCCTGAAGATTTGGACATGGAGGATAACGATATTATTGA

BsaI BamHI EcoRI SacI
                              ~~~~~~~~~~~~~~~~~~~~~~~~~
     uAlaHisArgGluGlnIleGlyGly***
401  GGCTCACCGCGAACAGATTGGAGGTTGAGACCGGATCCGAATTCGAGCTC
                              ↑
                      Hydrolase Cleavage Site NotI
     SalI HindIII EagI   XhoI
     ~~~~~~~~~~~~~~~~~~~~~~~~~
451  CGTCGACAAGCTTGCGGCCGCACTCGAG
```

Figure 13C

Amino acid sequence of NTHS protein (SEQ ID NO: 5)
msdsevnqea kpevkpevkp ethinlkvsd gsseiffkik kttplrrlme afak Nucleotide sequence of NTHS gene (SEQ ID NO: 6)
atgtcggactcag aagtcaatca agaagctaag ccagaggtca agccagaagt
caagcctgag actcacatca atttaaaggt gtccgatgga tcttcagaga
tcttcttcaa gatcaaaaag accactcctt taagaaggct gatggaagcg
ttcgctaaatga

Figure 14A

Amino acid sequence of 6xHis-NTHS protein as it is encoded in pET-6xHis-NTHS, (SEQ ID NO: 7)
mghhhhhhgs dsevnqea kpevkpevkp ethinlkvsd gsseiffkik
kttplrrlme afak Nucleotide sequence of 6xHis-NTHS gene as it appears in pET-6xHis-NTHS, (SEQ ID NO: 8)
atgggtcatc accatcatca tcacggg tcggactcag aagtcaatca agaagctaag
ccagaggtca agccagaagt caagcctgag actcacatca atttaaaggt
gtccgatgga tcttcagaga tcttcttcaa gatcaaaaag accactcctt
taagaaggct gatggaagcg ttcgctaaatga

Figure 14B

Amino acid sequence of CTHS protein, (SEQ ID NO: 9)
mkrqgkem dslrflydgi riqadqaped ldmedndiie ahreqigg Nucleotide sequence of CTHS gene, (SEQ ID NO: 10)
atgaaaa gacagggtaa ggaaatggac tccttaagat tcttgtacga cggtattaga
attcaagctg atcaggcccc tgaagatttg gacatggagg ataacgatat
tattgaggct cacagagaac agattggagg ttga

Figure 15A

Amino acid sequence of 6xHis-CTHS protein as it is encoded in pET-6xHis-CTHS, (SEQ ID NO: 11)
mghhhhhhkrqgkem dslrflydgi riqadqtped ldmedndiie ahreqigg Nucleotide sequence of 6xHis-CTHS gene as it appears in pET-6xHis-CTHS, (SEQ ID NO: 12)
atgggtcatc accatcatca tcacaaaa gacagggtaa ggaaatggac
tccttaagat tcttgtacga cggtattaga attcaagctg atcagacccc
tgaagatttg gacatggagg ataacgatat tattgaggct cacagagaac
agattggagg ttga

Figure 15B

```
            BglII
            ~~~~~~
  1   AGATCTCGATCCCGCGAAATTAATACGACTCACTATAGGGGAATTGTGAG

XbaI
                  ~~~~~~
 51   CGGATAACAATTCCCCTCTAGAAATAATTTTGTTTAACTTTAAGAAGGAG

NcoI
              ~~~~~~
              MetGlyHisHisHisHisHisHisLysArgGlnGlyLysGluM
101   ATATACCATGGGTCATCACCATCATCATCACAAAAGACAGGGTAAGGAAA

EcoRI
                                                 ~~~~~~
      etAspSerLeuArgPheLeuTyrAspGlyIleArgIleGlnAlaAspGln
151   TGGACTCCTTAAGATTCTTGTACGACGGTATTAGAATTCAAGCTGATCAG

ThrProGluAspLeuAspMetGluAspAsnAspIleIleGluAlaHisAr
201   ACCCCTGAAGATTTGGACATGGAGGATAACGATATTATTGAGGCTCACCG

BsaI BamHI EcoRI   SacI    SalI
                          ~~~~~~~~~~~~~~~~~~~~~~~  ~~~~~~
      gGluGlnIleGlyGly***
251   CGAACAGATTGGAGGTTGAGACCGGATCCGAATTCGAGCTCCGTCGACAA
                           ↑
                   Hydrolase Cleavage Site EagI
      HindIII NotI       XhoI
      ~~~~~~~~~~~~~~~~~~~~~~~
301   GCTTGCGGCCGCACTCGAG
```

Figure 15D

Amino acid sequence of GFP (enhanced Green Fluorescent Protein);
(SEQ ID NO: 13)

```
mvskgeelft gvvpilveld gdvnghkfsv sgegegdaty gkltlkfict tgklpvpwpt
lvttltygvq cfsrypdhmk qhdffksamp egyvqertif fkddgnyktr aevkfegdtl
vnrielkgid fkedgnilgh kleynynshn vyimadkqkn gikvnfkirh niedgsvqla
dhyqqntpig dgpvllpdnh ylstqsalsk dpnekrdhmv llefvtaagi tlgmdelyk
```

Nucleotide sequence of GFP (enhanced Green Fluorescent Protein) gene; a fragment of NCBI acc. No. AF525449
(SEQ ID NO: 14)

```
atggt gagcaagggc gaggagctgt tcaccggggt ggtgcccatc ctggtcgagc
tggacggcga cgtaaacggc cacaagttca gcgtgtccgg cgagggcgag
ggcgatgcca cctacggcaa gctgaccctg aagttcatct gcaccaccgg
caagctgccc gtgccctggc ccaccctcgt gaccaccctg acctacggcg
tgcagtgctt cagccgctac cccgaccaca tgaagcagca cgacttcttc
aagtccgcca tgcccgaagg ctacgtccag gagcgcacca tcttcttcaa
ggacgacggc aactacaaga cccgcgccga ggtgaagttc gagggcgaca
ccctggtgaa ccgcatcgag ctgaagggca tcgacttcaa ggaggacggc
aacatcctgg ggcacaagct ggagtacaac tacaacagcc acaacgtcta
tatcatggcc gacaagcaga agaacggcat caaggtgaac ttcaagatcc
gccacaacat cgaggacggc agcgtgcagc tcgccgacca ctaccagcag
aacaccccca tcggcgacgg ccccgtgctg ctgcccgaca accactacct
gagcacccag tccgccctga gcaaagaccc caacgagaag cgcgatcaca
tggtcctgct ggagttcgtg accgccgccg ggatcactct cggcatggac
gagctgtaca agtaa
```

Figure 16

Amino acid sequence of 6xHis-GFP protein as it is encoded in pET-6xHis-GFP, Yep and pFastBac plasmids;
(SEQ ID NO: 15)
mghhhhhhg
mvskgeelft gvvpilveld gdvnghkfsv sgegegdaty gkltlkfict tgklpvpwpt
lvttltygvq cfsrypdhmk qhdffksamp egyvqertif fkddgnyktr aevkfegdtl
vnrielkgid fkedgnilgh kleynynshn vyimadkqkn gikvnfkirh niedgsvqla
dhyqqntpig dgpvllpdnh ylstqsalsk dpnekrdhmv llefvtaagi tlgmdelyk Nucleotide sequence of 6xHis-GFP gene as it appears in pET-6xHis-GFP, Yep and pFastBac plasmids;
(SEQ ID NO: 16)
atgggtcatc accatcatca tcacggg atggt gagcaagggc gaggagctgt
tcaccggggt ggtgcccatc ctggtcgagc tggacggcga cgtaaacggc
cacaagttca gcgtgtccgg cgagggcgag ggcgatgcca cctacggcaa
gctgaccctg aagttcatct gcaccaccgg caagctgccc gtgccctggc
ccaccctcgt gaccaccctg acctacggcg tgcagtgctt cagccgctac
cccgaccaca tgaagcagca cgacttcttc aagtccgcca tgcccgaagg
ctacgtccag gagcgcacca tcttcttcaa ggacgacggc aactacaaga
cccgcgccga ggtgaagttc gagggcgaca ccctggtgaa ccgcatcgag
ctgaagggca tcgacttcaa ggaggacggc aacatcctgg ggcacaagct
ggagtacaac tacaacagcc acaacgtcta tatcatggcc gacaagcaga
agaacggcat caaggtgaac ttcaagatcc gccacaacat cgaggacggc
agcgtgcagc tcgccgacca ctaccagcag aacacccca tcggcgacgg
ccccgtgctg ctgcccgaca ccactacct gagcacccag tccgccctga
gcaaagaccc caacgagaag cgcgatcaca tggtcctgct ggagttcgtg
accgccgccg ggatcactct cggcatggac gagctgtaca agtaa

Figure 17

Amino acid sequence of 6xHis-SUMO-GFP protein as it is encoded in pET-6xHis-SUMO-GFP, Yep and pFastBac plasmids;
(SEQ ID NO: 17)
mghhhhhhgs dsevnqea kpevkpevkp ethinlkvsd gsseiffkik kttplrrlme
afakrqgkem dslrflydgi riqadqaped ldmedndiie ahreqigg mvskgeelft
gvvpilveld gdvnghkfsv sgegegdaty gkltlkfict tgklpvpwpt lvttltygvq
cfsrypdhmk qhdffksamp egyvqertif fkddgnyktr aevkfegdtl vnrielkgid
fkedgnilgh kleynynshn vyimadkqkn gikvnfkirh niedgsvqla dhyqqntpig
dgpvllpdnh ylstqsalsk dpnekrdhmv llefvtaagi tlgmdelyk Nucleotide sequence of 6xHis-SUMO-GFP gene as it is encoded in pET-6xHis-SUMO-GFP, Yep and pFastBac plasmids;
(SEQ ID NO: 18)
atgggtcatc accatcatca tcacggg tcggactcag aagtcaatca agaagctaag
ccagaggtca agccagaagt caagcctgag actcacatca atttaaaggt
gtccgatgga tcttcagaga tcttcttcaa gatcaaaaag accactcctt
taagaaggct gatggaagcg ttcgctaaaa gacagggtaa ggaaatggac
tccttaagat tcttgtacga cggtattaga attcaagctg atcaggcccc
tgaagatttg gacatggagg ataacgatat tattgaggct cacagagaac
agattggagg tatggt gagcaagggc gaggagctgt tcaccggggt ggtgcccatc
ctggtcgagc tggacggcga cgtaaacggc cacaagttca gcgtgtccgg
cgagggcgag ggcgatgcca cctacggcaa gctgaccctg aagttcatct
gcaccaccgg caagctgccc gtgcctggc cacctcgt gaccaccctg
acctacggcg tgcagtgctt cagccgctac cccgaccaca tgaagcagca
cgacttcttc aagtccgcca tgcccgaagg ctacgtccag gagcgcacca
tcttcttcaa ggacgacggc aactacaaga cccgcgccga ggtgaagttc
gagggcgaca ccctggtgaa ccgcatcgag ctgaagggca tcgacttcaa
ggaggacggc aacatcctgg ggcacaagct ggagtacaac tacaacagcc
acaacgtcta tatcatggcc gacaagcaga gaacggcat caaggtgaac
ttcaagatcc gccacaacat cgaggacggc agcgtgcagc tcgccgacca
ctaccagcag aacacccca tcggcgacgg ccccgtgctg ctgcccgaca
accactacct gagcacccag tccgccctga caaagaccc caacgagaag
cgcgatcaca tggtcctgct ggagttcgtg accgccgccg ggatcactct
cggcatggac gagctgtaca agtaa

Figure 18

Amino acid sequence of 6xHis-CTHS-GFP protein as it is encoded in pET-6xHis-CTHS-GFP, Yep and pFastBac plasmids;
(SEQ ID NO: 19)
mghhhhhhkrqgkem dslrflydgi riqadqaped ldmedndiie ahreqigg
mvskgeelft gvvpilveld gdvnghkfsv sgegegdaty gkltlkfict tgklpvpwpt
lvttltygvq cfsrypdhmk qhdffksamp egyvqertif fkddgnyktr aevkfegdtl
vnrielkgid fkedgnilgh kleynynshn vyimadkqkn gikvnfkirh niedgsvqla
dhyqqntpig dgpvllpdnh ylstqsalsk dpnekrdhmv llefvtaagi tlgmdelyk Nucleotide sequence of 6xHis-CTHS-GFP gene as it appears in pET-6xHis-CTHS-GFP, Yep and pFastBac plasmids
(SEQ ID NO: 20)
atgggtcatc accatcatca tcacaaaa gacagggtaa ggaaatggac
tccttaagat tcttgtacga cggtattaga attcaagctg atcaggcccc
tgaagatttg gacatggagg ataacgatat tattgaggct cacagagaac
agattggagg tatggt gagcaagggc gaggagctgt tcaccggggt ggtgcccatc
ctggtcgagc tggacggcga cgtaaacggc cacaagttca gcgtgtccgg
cgagggcgag ggcgatgcca cctacggcaa gctgaccctg aagttcatct
gcaccaccgg caagctgccc gtgcctggc ccaccctcgt gaccaccctg
acctacggcg tgcagtgctt cagccgctac cccgaccaca tgaagcagca
cgacttcttc aagtccgcca tgcccgaagg ctacgtccag gagcgcacca
tcttcttcaa ggacgacggc aactacaaga cccgcgccga ggtgaagttc
gagggcgaca ccctggtgaa ccgcatcgag ctgaagggca tcgacttcaa
ggaggacggc aacatcctgg ggcacaagct ggagtacaac tacaacagcc
acaacgtcta tatcatggcc gacaagcaga gaacggcat caaggtgaac
ttcaagatcc gccacaacat cgaggacggc agcgtgcagc tcgccgacca
ctaccagcag aacacccca tcggcgacgg ccccgtgctg ctgcccgaca
accactacct gagcacccag tccgccctga gcaaagaccc caacgagaag
cgcgatcaca tggtcctgct ggagttcgtg accgccgccg ggatcactct
cggcatggac gagctgtaca agtaa

Figure 19

Amino acid sequence of GST protein (glutathione transferase) and the recognition site for Tev protease;
(SEQ ID NO: 21)

```
mspilgywki kglvqptrll leyleekyee hlyerdegdk wrnkkfelgl
efpnlpyyid gdvkltqsma iiryiadkhn mlggcpkera eismlegavl
dirygvsria yskdfetlkv dflsklpeml kmfedrlchk tylngdhvth
pdfmlydald vvlymdpmcl dafpklvcfk krieaipqid kylksskyia
wplqgwqatf gggdhpptsg sggggggwmse nlyfqg
```

Nucleotide sequence of GST gene;
(SEQ ID NO: 22)

```
atgtccccta tactaggtta ttggaaaatt aagggccttg tgcaacccac
tcgacttctt ttggaatatc ttgaagaaaa atatgaagag catttgtatg
agcgcgatga aggtgataaa tggcgaaaca aaaagtttga attgggtttg
gagtttccca atcttcctta ttatattgat ggtgatgtta aattaacaca
gtctatggcc atcatacgtt atatagctga caagcacaac atgttgggtg
gttgtccaaa agagcgtgca gagatttcaa tgcttgaagg agcggttttg
gatattagat acggtgtttc gagaattgca tatagtaaag actttgaaac
tctcaaagtt gatttttctta gcaagctacc tgaaatgctg aaaatgttcg
aagatcgttt atgtcataaa acatatttaa atggtgatca tgtaacccat
cctgacttca tgttgtatga cgctcttgat gttgttttat acatggaccc
aatgtgcctg gatgcgttcc caaaattagt ttgtttttaaa aaacgtattg
aagctatccc acaaattgat aagtacttga aatccagcaa gtatatagca
tggcctttgc agggctggca agccacgttt ggtggtggcg accatcctcc
aactagtgga tctggtggtg gtggcggatg gatgagcgag aatctttatt
ttcaaggttg a
```

Figure 20

Amino acid sequence of GST-6xHis-SUMO-GFP protein as it is encoded in pET-GST-6xHis-SUMO-GFP (SEQ ID NO: 23)

```
mspilgywki kglvqptrll leyleekyee hlyerdegdk wrnkkfelgl
efpnlpyyid gdvkltqsma iiryiadkhn mlggcpkera eismlegavl
dirygvsria yskdfetlkv dflsklpeml kmfedrlchk tylngdhvth
pdfmlydald vvlymdpmcl dafpklvcfk krieaipqid kylksskyia
wplqgwqatf gggdhpptsg sggggwmse nlyfqgamgh hhhhhgsdse
vnqeakpevk pevkpethin lkvsdgssei ffkikkttpl rrlmeafakr
qgkemdslrf lydgiriqad qapedldmed ndiieahreq iggmvskgee
lftgvvpilv eldgdvnghk fsvsgegegd atygkltlkf icttgklpvp
wptlvttlty gvqcfsrypd hmkqhdffks ampegyvqer tiffkddgny
ktraevkfeg dtlvnrielk gidfkedgni lghkleynyn shnvyimadk
qkngikvnfk irhniedgsv qladhyqqnt pigdgpvllp dnhylstqsa
lskdpnekrd hmvllefvta agitlgmdel yk
```

Nucleotide sequence of GST-6xHis-SUMO-GFP gene as it appears in pET-GST-6xHis-SUMO-GFP (SEQ ID NO: 24)

```
atgtcccta tactaggtta ttggaaaatt aagggccttg tgcaacccac
tcgacttctt ttggaatatc ttgaagaaaa atatgaagag catttgtatg
agcgcgatga aggtgataaa tggcgaaaca aaaagtttga attgggtttg
gagtttccca atcttcctta ttatattgat ggtgatgtta aattaacaca
gtctatggcc atcatacgtt atatagctga caagcacaac atgttgggtg
gttgtccaaa agagcgtgca gagatttcaa tgcttgaagg agcggttttg
gatattgat acggtgtttc gagaattgca tatagtaaag actttgaaac
tctcaaagtt gatttctta gcaagctacc tgaaatgctg aaaatgttcg
aagatcgttt atgtcataaa acatatttaa atggtgatca tgtaacccat
cctgacttca tgttgtatga cgctcttgat gttgttttat acatggaccc
aatgtgcctg gatgcgttcc caaaattagt ttgttttaaa aaacgtattg
aagctatccc acaaattgat aagtacttga atccagcaa gtatatagca
tggcctttgc agggctggca agccacgttt ggtggtggcg accatcctcc
aactagtgga tctggtggtg gtggcggatg gatgagcgag aatctttatt
ttcaaggtgc catgggtcat caccatcatc atcacgggtc ggactcagaa
gtcaatcaag aagctaagcc agaggtcaag ccagaagtca agcctgagac
tcacatcaat ttaaaggtgt ccgatggatc ttcagagatc ttcttcaaga
tcaaaaagac cactccttta agaaggctga tggaagcgtt cgctaaaaga
cagggtaagg aaatggactc cttaagattc ttgtacgacg gtattagaat
tcaagctgat caggcccctg aagatttgga catggaggat aacgatatta
ttgaggctca ccgcgaacag attggaggta tggtgagcaa gggcgaggag
ctgttcaccg gggtggtgcc catcctggtc gagctggacg gcgacgtaaa
cggccacaag ttcagcgtgt ccggcgaggg cgagggcgat gccacctacg
gcaagctgac cctgaagttc atctgcacca ccggcaagct gcccgtgccc
tggcccaccc tcgtgaccac cctgacctac ggcgtgcagt gcttcagccg
ctacccgac cacatgaagc agcacgactt cttcaagtcc gccatgcccg
aaggctacgt ccaggagcgc accatcttct tcaaggacga cggcaactac
aagacccgcg ccgaggtgaa gttcgagggc gacaccctgg tgaaccgcat
cgagctgaag ggcatcgact tcaaggagga cggcaacatc ctggggcaca
agctggagta caactacaac agccacaacg tctatatcat ggccgacaag
cagaagaacg gcatcaaggt gaacttcaag atccgccaca acatcgagga
cggcagcgtg cagctcgccg accactacca gcagaacacc cccatcggcg
acggccccgt gctgctgccc gacaaccact acctgagcac ccagtccgcc
ctgagcaaag accccaacga aagcgcgat cacatggtcc tgctggagtt
cgtgaccgcc gccgggatca ctctcggcat ggacgagctg tacaagtaa
```

Figure 21

Amino acid sequence of GST-6xHis-CTHS-GFP protein as it is encoded in pET-GST-6xHis-CTHS-GFP (SEQ ID NO: 25)

```
mspilgywki kglvqptrll leyleekyee hlyerdegdk wrnkkfelgl
efpnlpyyid gdvkltqsma iiryiadkhn mlggcpkera eismlegavl
dirygvsria yskdfetlkv dflsklpeml kmfedrlchk tylngdhvth
pdfmlydald vvlymdpmcl dafpklvcfk krieaipqid kylksskyia
wplqgwqatf gggdhpptsg sggggwmse nlyfqgah mghhhhhhkr qgkem
dslrflydgi riqadqaped ldmedndiie ahreqigg mvskgeelft
gvvpilveld gdvnghkfsv sgegegdaty gkltlklict tgklpvpwpt
lvttlgxglq cfarypdhmk qhdffksamp egyvcertif fkddgnyktr
aevkfegdtl vnrielkgid fkedgnilgh kleynynshn vyitadkqkn
gikanfkirh niedggvqla dhyqqntpig dgpvllpdnh ylsyqsalsk
dpnekrdhmv llefvtaagi thgmdelyk
```

Nucleotide sequence of GST-6xHis-CTHS-GFP gene as it appears in pET-GST-6xHis-CTHS-GFP (SEQ ID NO: 26)

```
atgtcccta tactaggtta ttggaaaatt aagggccttg tgcaacccac
tcgacttctt ttggaatatc ttgaagaaaa atatgaagag catttgtatg
agcgcgatga aggtgataaa tggcgaaaca aaaagtttga attgggtttg
gagtttccca atcttcctta ttatattgat ggtgatgtta aattaacaca
gtctatggcc atcatacgtt atatagctga caagcacaac atgttgggtg
gttgtccaaa agagcgtgca gagatttcaa tgcttgaagg agcggttttg
gatattagat acggtgtttc gagaattgca tatagtaaag actttgaaac
tctcaaagtt gattttctta gcaagctacc tgaaatgctg aaaatgttcg
aagatcgttt atgtcataaa acatatttaa atggtgatca tgtaacccat
cctgacttca tgttgtatga cgctcttgat gttgttttat acatggaccc
aatgtgcctg gatgcgttcc caaaattagt ttgttttaaa aaacgtattg
aagctatccc acaaattgat aagtacttga atccagcaa gtatatagca
tggcctttgc agggctggca agccacgttt ggtggtggcg accatcctcc
aactagtgga tctggtggtg gtggcggatg gatgagcgag aatctttatt
ttcaaggtgc catgggtcat caccatcatc atcacagaca gggtaaggaa
atggactcct taagattctt gtacgacggt attagaattc aagctgatca
ggcccctgaa gatttggaca tggaggataa cgatattatt gaggctcacc
gcgaacagat tggaggtatg gtgagcaagg gcgaggagct gttcaccggg
gtggtgccca tcctggtcga gctggacggc gacgtaaacg gccacaagtt
cagcgtgtcc ggcgagggcg agggcgatgc cacctacggc aagctgaccc
tgaagttcat ctgcaccacc ggcaagctgc ccgtgccctg gcccaccctc
gtgaccaccc tgacctacgg cgtgcagtgc ttcagccgct accccgacca
catgaagcag cacgacttct tcaagtccgc catgcccgaa ggctacgtcc
aggagcgcac catcttcttc aaggacgacg gcaactacaa gacccgcgcc
gaggtgaagt tcgagggcga caccctggtg aaccgcatcg agctgaaggg
catcgacttc aaggaggacg gcaacatcct ggggcacaag ctggagtaca
actacaacag ccacaacgtc tatatcatgg ccgacaagca gaagaacggc
atcaaggtga acttcaagat ccgccacaac atcgaggacg gcagcgtgca
gctcgccgac cactaccagc agaacacccc catcggcgac ggccccgtgc
tgctgcccga caaccactac ctgagcaccc agtccgccct gagcaaagac
cccaacgaga agcgcgatca catggtcctg ctggagttcg tgaccgccgc
cgggatcact ctcggcatgg acgagctgta caagtaa
```

Figure 22

Amino acid sequence of Cys-6xHis-NTHS protein as it is encoded in pET-Cys-6xHis-NTHS (SEQ ID NO: 27)
mgchhhhhhgs dsevnqea kpevkpevkp ethinlkvsd gsseiffkik
kttplrrlme afak Nucleotide sequence of Cys-6xHis-NTHS gene as it appears in pET-Cys-6xHis-NTHS (SEQ ID NO: 28)
atgggttgcc atcaccatca tcatcacggg tcggactcag aagtcaatca
agaagctaag ccagaggtca agccagaagt caagcctgag actcacatca
atttaaaggt gtccgatgga tcttcagaga tcttcttcaa gatcaaaaag
accactcctt taagaaggct gatggaagcg ttcgctaaatga

Figure 23

The amino acid (SEQ ID NO: 29) and nucleotide (SEQ ID NO: 30) sequences of catalytic domain of Ulp1 SUMO protease (hydrolase).

(SEQ ID NO: 29)
```
lvpelnek   dddqvqkala  srentqlmnr  dnieitvrdf  ktlaprrwln
dtiieffmky iekstpntva  fnsffytnls  ergyqgvrrw  mkrkktqidk
ldkiftpinl nqshwalgii  dlkkktigyv  dslsngpnam  sfailtdlqk
yvmeeskhti gedfdlihld  cpqqpngydc  giyvcmntly  gsadapldfd
ykdairmrrf iahliltdal  k
```

(SEQ ID NO: 30)
```
cttg ttcctgaatt aaatgaaaaa gacgatgacc aagtacaaaa agctttggca
tctagagaaa atactcagtt aatgaataga gataatatag agataacagt
acgtgatttt aagaccttgg caccacgaag atggctaaat gacactatca
ttgagttttt tatgaaatac attgaaaaat ctacccctaa tacagtggcg
tttaattcat ttttctatac caatttatca gaaggggtt atcaaggcgt
ccggaggtgg atgaagagaa agaagacaca aattgataaa cttgataaaa
tctttacacc aataaatttg aaccaatccc actgggcgtt gggcataatt
gatttaaaaa agaaaactat aggttacgta gattcattat cgaatggtcc
aaatgctatg agtttcgcta tactgactga cttgcaaaaa tatgttatgg
aggaaagtaa gcatacaata ggagaagact tgatttgat tcatttagat
tgtccgcagc aaccaaatgg ctacgactgt ggaatatatg tttgtatgaa
tactctctat ggaagtgcag atgcgccatt ggattttgat tataaagatg
cgattaggat gagaagattt attgcccatt tgattttaac cgacgcttta
aaa
```

Figure 24

Amino acid sequence of CTHS-1 protein, (SEQ ID NO: 31)
mkem dslrflydgi riqadqaped ldmedndiie ahreqigg Nucleotide sequence of CTHS-1 gene, (SEQ ID NO: 32)
atgaa ggaaatggac tccttaagat tcttgtacga cggtattaga attcaagctg
atcaggcccc tgaagatttg gacatggagg ataacgatat tattgaggct
cacagagaac agattggagg ttga Amino acid sequence of 6xHis-CTHS-1 protein as it is encoded in pET-6xHis-CTHS,
(SEQ ID NO: 33)
mghhhhhhkem dslrflydgi riqadqaped ldmedndiie ahreqigg Nucleotide sequence of 6xHis-CTHS-1 gene as it appears in pET-6xHis-CTHS,
(SEQ ID NO: 34)
atgggtcatc accatcatca tcacaa ggaaatggac tccttaagat tcttgtacga
cggtattaga attcaagctg atcaggcccc tgaagatttg gacatggagg
ataacgatat tattgaggct cacagagaac agattggagg ttga Amino acid sequence of NTHS-1 protein (SEQ ID NO: 91)
msdsevnqea kpevkpevkp ethinlkvsd gsseiffkik kttplrrlme afak Nucleotide sequence of NTHS-1 gene,(SEQ ID NO: 92)
atgtcggactcag aagtcaatca agaagctaag
ccagaggtca agccagaagt caagcctgag actcacatca atttaaaggt
gtccgatgga tcttcagaga tcttcttcaa gatcaaaaag accactcctt
taagaaggct gatggaagcg ttcgctaaa Amino acid sequence of 6xHis-NTHS-1-6xHis protein as it is encoded in pET-6xHis-
NTHS-1,
(SEQ ID NO: 93)
mghhhhhhgs dsevnqea kpevkpevkp ethinlkvsd gsseiffkik
kttplrrlme afakrqgkek laaalehhhh hh Nucleotide sequence of 6xHis-NTHS-1-6xHis gene as it appears in pET-6xHis-
NTHS-1,
(SEQ ID NO: 94)
atgggtcatc accatcatca tcacggg tcggactcag aagtcaatca agaagctaag
ccagaggtca agccagaagt caagcctgag actcacatca atttaaaggt
gtccgatgga tcttcagaga tcttcttcaa gatcaaaaag accactcctt
taagaaggct gatggaagcg ttcgctaaaa gacagggtaa ggaaaagctt
gcggccgcac tcgagcacca ccaccaccac cactga

Figure 25

Ubiquitin ACC.# NP_002945
Amino-acid sequence of Amino-terminal domain, Version 1
MQIFVKTLTG KTITLEVEPS DTIENVKAKI Q    (SEQ ID NO: 95)
Amino-acid sequence of Carboxy-terminal domain, Version 1
DKEGIPPDQQ RLIFAGKQLE DGRTLSDYNI QKESTLHLVL RLRGG    (SEQ ID NO: 96)

Amino-acid sequence of Amino-terminal domain, Version 2
MQIFVKTLTG KTITLEVEPS DTIENVKAKI QDKEGIPP    (SEQ ID NO: 97)
Amino-acid sequence of Carboxy-terminal domain, Version 2
DQQRLIFAGK QLEDGRTLSD YNIQKESTLH LVLRLRGG    (SEQ ID NO: 98)

Nedd8 ACC.# Q15843
Amino-acid sequence of Amino-terminal domain, Version 1
MLIKVKTLTG KEIEIDIEPT DKVERIKERV EE    (SEQ ID NO: 37)
Amino-acid sequence of Carboxy-terminal domain, Version 1
KEGIPPQQQR LIYSGKQMND EKTAADYKIL GG    (SEQ ID NO: 38)

Amino-acid sequence of Amino-terminal domain, Version 2
MLIKVKTLTG KEIEIDIEPT DKVERIKERV EEKEGIPPQ    (SEQ ID NO: 39)
Amino-acid sequence of Carboxy-terminal domain, Version 2
QQRLIYSGKQ MNDEKTAADY KILGG    (SEQ ID NO: 40)

Hub1 ACC.# NP_014430
Amino-acid sequence of Amino-terminal domain, Version 1
MIEVVVNDRL GKKVRVKCLA EDSVGDFKKV LS    (SEQ ID NO: 41)
Amino-acid sequence of Carboxy-terminal domain, Version 1
LQIGTQPNKI VLQKGGSVLK DHISLEDYEV HDQTNLELYY    (SEQ ID NO: 42)

Amino-acid sequence of Amino-terminal domain, Version 2
MIEVVVNDRL GKKVRVKCLA EDSVGDFKKV LSLQIGTQPN    (SEQ ID NO: 43)
Amino-acid sequence of Carboxy-terminal domain, Version 2
KIVLQKGGSV LKDHISLEDY EVHDQTNLEL YY    (SEQ ID NO: 44)

Figure 26A

ISG15 ACC.# P05161
Amino-acid sequence of Amino-terminal domain, Version 1
MGWDLTVKML AGNEFQVSLS SSMSVSELKA QITQNIGVHA FQQRLAVHPS
GVALQDRVPL ASQGLGPGST VLLVVDKCDE PLSILVRNNK GRSSTYEVRL
TQTVAHLKQQ VSG (SEQ ID NO: 45)
Amino-acid sequence of Carboxy-terminal domain, Version 1
LEGVQDDLFW LTFEGKPLED QLPLGEYGLK PLSTVFMNLR LRGG (SEQ ID NO: 46)

Amino-acid sequence of Amino-terminal domain, Version 2
MGWDLTVKML AGNEFQVSLS SSMSVSELKA QITQNIGVHA FQQRLAVHPS
GVALQDRVPL ASQGLGPGST VLLVVDKCDE PLSILVRNNK GRSSTYEVRL
TQTVAHLKQQ VSGLEGVQDD (SEQ ID NO: 47)
Amino-acid sequence of Carboxy-terminal domain, Version 2
LFWLTFEGKP LEDQLPLGEY GLKPLSTVFM NLRLRGG (SEQ ID NO: 48)

APG12 ACC.# NP_009776
Amino-acid sequence of Amino-terminal domain, Version 1
MSRILESENE TESDESSIIS TNNGTAMERS RNNQELRSSP HTVQNRLELF
SRRLSQLGLA SDISVDQQVE DSSSGTYEQE ETIKTNAQTS KQKSHKDEKN
IQKIQIKFQP IGSIGQLKPS VCKISMSQSF AMVILFL (SEQ ID NO: 49)
Amino-acid sequence of Carboxy-terminal domain, Version 1
KRRLKMDHVY CYINNSFAPS PQQNIGELWM QFKTNDELIV SYCASVAFG
(SEQ ID NO: 50)

Amino-acid sequence of Amino-terminal domain, Version 2
MSRILESENE TESDESSIIS TNNGTAMERS RNNQELRSSP HTVQNRLELF
SRRLSQLGLA SDISVDQQVE DSSSGTYEQE ETIKTNAQTS KQKSHKDEKN
IQKIQIKFQP IGSIGQLKPS VCKISMSQSF AMVILFLKRR LKMDH (SEQ ID NO: 51)
Amino-acid sequence of Carboxy-terminal domain, Version 2
VYCYINNSFA PSPQQNIGEL WMQFKTNDEL IVSYCASVAF G (SEQ ID NO: 52)

Apg8, ACC.# P38182
Amino-acid sequence of Amino-terminal domain, Version 1
MKSTFKSEYP FEKRKAESER IADRFKNRIP VICEKAEKSD IPEIDKRKYL
VPADLTVGQF VYVIRKRIML (SEQ ID NO: 53)
Amino-acid sequence of Carboxy-terminal domain, Version 1
PPEKAIFIFV NDTLPPTAAL MSAIYQEHKD KDGFLYVTYS GENTFG (SEQ ID NO: 54)

Amino-acid sequence of Amino-terminal domain, Version 2
MKSTFKSEYP FEKRKAESER IADRFKNRIP VICEKAEKSD IPEIDKRKYL
VPADLTVGQF VYVIRKRIML PPEKAI (SEQ ID NO: 55)
Amino-acid sequence of Carboxy-terminal domain, Version 2
FIFVNDTLPP TAALMSAIYQ EHKDKDGFLY VTYSGENTFG (SEQ ID NO: 56)

Figure 26B

FAT10, ACC.# NP_006389
Amino-acid sequence of Amino-terminal domain, Version 1
MAPNASCLCV HVRSEEWDLM TFDANPYDSV KKIKEHVRSK TKVPVQDQVL
LLGSKILKPR RSLSSYGIDK EKTIHLTLKV VKPSDEELPL FLVESGDEAK
RHLLQVRRSS SVAQVKAMI  (SEQ ID NO: 57)
Amino-acid sequence of Carboxy-terminal domain, Version 1
ETKTGIIPET QIVTCNGKRL EDGKMMADYG IRKGNLLPLA SYCIGG  (SEQ ID NO: 58)

Amino-acid sequence of Amino-terminal domain, Version 2
MAPNASCLCV HVRSEEWDLM TFDANPYDSV KKIKEHVRSK TKVPVQDQVL
LLGSKILKPR RSLSSYGIDK EKTIHLTLKV VKPSDEELPL FLVESGDEAK
RHLLQVRRSS SVAQVKAMIE TKTGIIP  (SEQ ID NO: 59)
Amino-acid sequence of Carboxy-terminal domain, Version 2
ETQIVTCNGK RLEDGKMMAD YGIRKGNLLF LASYCIGG  (SEQ ID NO: 60)

URM1, ACC.# NP_012258
Amino-acid sequence of Amino-terminal domain, Version 1
MVNVKVEFLG GLDAIFGKQR VHKIKMDKED PVTVGDLIDH IVSTMINNPN
DVSIFI  (SEQ ID NO: 61)
Amino-acid sequence of Carboxy-terminal domain, Version 1
EDDS IRPGIITLIN DTDWELEGEK DYILEDGDII SFTSTLHGG  (SEQ ID NO: 62)

Amino-acid sequence of Amino-terminal domain, Version 2
MVNVKVEFLG GLDAIFGKQR VHKIKMDKED PVTVGDLIDH IVSTMINNPN
DVSIFIEDDS I  (SEQ ID NO: 63)
Amino-acid sequence of Carboxy-terminal domain, Version 2
RPGIITLIND TDWELEGEKD YILEDGDIIS FTSTLHGG  (SEQ ID NO: 64)

Ubi-L, ACC.# P35545
Amino-acid sequence of Amino-terminal domain, Version 1
MQLFVRAQEL HTLEVTGQET VAQIKDHVA  (SEQ ID NO: 65)
Amino-acid sequence of Carboxy-terminal domain, Version 1
SLEGIAPEDQ VVLLAGSPLE DEATLGQCGV EALTTLEVAG RMLGG  (SEQ ID NO: 66)

Amino-acid sequence of Amino-terminal domain, Version 2
MQLFVRAQEL HTLEVTGQET VAQIKDHVAS LEGIAPE  (SEQ ID NO: 67)
Amino-acid sequence of Carboxy-terminal domain, Version 2
DQVVLLAGSP LEDEATLGQC GVEALTTLEV AGRMLGG  (SEQ ID NO: 68)

Figure 26C

PARK2, ACC.# NP_054642
MIVFVRFNSS HGFPVEVDSD TSIFQLKEVV AKRQGVPADQ LRVIFAGKEL
RNDWTVQNCD LDQQSIVHIV QRPWRK (SEQ ID NO: 105)

Amino-acid sequence of Amino-terminal domain, Version 1
MIVFVRFNSS HGFPVEVDSD TSIFQLKEVV AKR (SEQ ID NO: 106)
Amino-acid sequence of Carboxy-terminal domain, Version 1
QGVPADQ LRVIFAGKEL RNDWTVQNCD LDQQSIVHIV QRPWRK (SEQ ID NO:
107)

Amino-acid sequence of Amino-terminal domain, Version 2
MIVFVRFNSS HGFPVEVDSD TSIFQLKEVV AKRQGVPADQ (SEQ ID NO: 108)
Amino-acid sequence of Carboxy-terminal domain, Version 2
LRVIFAGKEL RNDWTVQNCD LDQQSIVHIV QRPWRK (SEQ ID NO: 109)

MoaD, ACC.# NP_752796
MTLRWKRMIN VLFFAQVREL VGTDATEVAA DFPTVEALRQ HLAAQSDRWA
LALEDGKLLA AVNQTLVSFD HSLTDGDEVA FFPPVTGG (SEQ ID NO: 110)

Amino-acid sequence of Amino-terminal domain, Version 1
MTLRWKRMIN VLFFAQVREL VGTDATEVAA DFPTVEALRQ HLAAQSDRWA LAL
(SEQ ID NO: 111)
Amino-acid sequence of Carboxy-terminal domain, Version 1
EDGKLLA AVNQTLVSFD HSLTDGDEVA FFPPVTGG (SEQ ID NO: 112)

Amino-acid sequence of Amino-terminal domain, Version 2
MTLRWKRMIN VLFFAQVREL VGTDATEVAA DFPTVEALRQ HLAAQSDRWA
LALEDGKL (SEQ ID NO: 113)
Amino-acid sequence of Carboxy-terminal domain, Version 2
LA AVNQTLVSFD HSLTDGDEVA FFPPVTGG (SEQ ID NO: 114)

Bem1p, ACC.# 1IP9_A
GAMGSSTSGL KTTKIKFYYK DDIFALMLKG DTTYKELRSK IAPRIDTDNF
KLQTKLFDGS GEEIKTDSQV SNIIQAKLKI SVHDI (SEQ ID NO: 115)

Amino-acid sequence of Amino-terminal domain, Version 1
GAMGSSTSGL KTTKIKFYYK DDIFALMLKG DTTYKELRSK I (SEQ ID NO: 116)
Amino-acid sequence of Carboxy-terminal domain, Version 1
APRIDTDNF KLQTKLFDGS GEEIKTDSQV SNIIQAKLKI SVHDI (SEQ ID NO:
117)

Amino-acid sequence of Amino-terminal domain, Version 2
GAMGSSTSGL KTTKIKFYYK DDIFALMLKG DTTYKELRSK IAPRIDTD (SEQ ID
NO: 118)
Amino-acid sequence of Carboxy-terminal domain, Version 2
NF KLQTKLFDGS GEEIKTDSQV SNIIQAKLKI SVHDI (SEQ ID NO: 119)

Figure 27A

CPAN, ACC.# AAC39709
MLQKPKSVKL RALRSPRKFG VAGRSCQEVL RKGCLRFQLP ERGSRLCLYE
DGTELTEDYF PSVPDNAELV LLTLGQAWQG (SEQ ID NO: 120)

Amino-acid sequence of Amino-terminal domain, Version 1
MLQKPKSVKL RALRSPRKFG VAGRSCQEVL RKGCLR (SEQ ID NO: 121)
Amino-acid sequence of Carboxy-terminal domain, Version 1
FQLP ERGSRLCLYE DGTELTEDYF PSVPDNAELV LLTLGQAWQG (SEQ ID NO: 122)

Amino-acid sequence of Amino-terminal domain, Version 2
MLQKPKSVKL RALRSPRKFG VAGRSCQEVL RKGCLRFQLP ERG (SEQ ID NO: 123)
Amino-acid sequence of Carboxy-terminal domain, Version 2
SRLCLYE DGTELTEDYF PSVPDNAELV LLTLGQAWQG (SEQ ID NO: 124)

SpeH, ACC.# NP_269186
KEI KVPVNVWDKS KQQPPMFITV NKPKVTAQEV DIKVRKLLIK KYDIYNNREQ
KYSKGTVTLD LNSGKDIVFD LYYFGNGDFN SMLKIYSNNE RIDSTQFHVD
VSIS (SEQ ID NO: 125)

Amino-acid sequence of Amino-terminal domain, Version 1
KEI KVPVNVWDKS KQQPPMFITV NKPKVTAQEV DIKVRKLLIK K (SEQ ID NO: 126)
Amino-acid sequence of Carboxy-terminal domain, Version 1
YDIYNNREQ KYSKGTVTLD LNSGKDIVFD LYYFGNGDFN SMLKIYSNNE
RIDSTQFHVD VSIS (SEQ ID NO: 127)

Amino-acid sequence of Amino-terminal domain, Version 2
KEI KVPVNVWDKS KQQPPMFITV NKPKVTAQEV DIKVRKLLIK KYDIYNNREQ KYS
(SEQ ID NO: 128)
Amino-acid sequence of Carboxy-terminal domain, Version 2
KGTVTLD LNSGKDIVFD LYYFGNGDFN SMLKIYSNNE RIDSTQFHVD VSIS (SEQ
ID NO: 129)

SPG, ACC.# P06654
MTPAVTTYKL VINGKTLKGE TTTKAVDAET AEKAFKQYAN DNGVDGVWTY
DDATKTFTVT E (SEQ ID NO: 130)

Amino-acid sequence of Amino-terminal domain, Version 1
MTPAVTTYKL VINGKTLKGE TTTKAVDAET AEKAFKQYAN DNG (SEQ ID NO: 131)
Amino-acid sequence of Carboxy-terminal domain, Version 1
VDGVWTY DDATKTFTVT E (SEQ ID NO: 132)

Amino-acid sequence of Amino-terminal domain, Version 2
MTPAVTTYKL VINGKTLKGE TTTKAVDAET AEKAFKQYAN DNGVDG (SEQ ID NO: 133)
Amino-acid sequence of Carboxy-terminal domain, Version 2
VWTY DDATKTFTVT E (SEQ ID NO: 134)

Figure 27B

INFC, ACC.# P03000
MSKDFIINEQ IRAREVRLID QNGDQLGIKS KQEALEIAAR RNLDLVLVAP
NAKPPVCRIM DY (SEQ ID NO: 135)

Amino-acid sequence of Amino-terminal domain, Version 1
MSKDFIINEQ IRAREVRLID QNGDQLGIKS KQEALEIAA (SEQ ID NO: 136)
Amino-acid sequence of Carboxy-terminal domain, Version 1
RRNLDLVLVAP NAKPPVCRIM DY (SEQ ID NO: 137)

Amino-acid sequence of Amino-terminal domain, Version 2
MSKDFIINEQ IRAREVRLID QNGDQLGIKS KQEALEIAAR RNL (SEQ ID NO: 138)
Amino-acid sequence of Carboxy-terminal domain, Version 2
DLVLVAP NAKPPVCRIM DY (SEQ ID NO: 139)

Figure 27C

SEQUENCE LISTING

<160> NUMBER OF SEQ ID NOS: 140

<210> SEQ ID NO 1
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 1

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Ala Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 2
<211> LENGTH: 294
<212> TYPE: DNA
<213> ORGANISM: Artificial Sequence
<220> FEATURE:
<223> OTHER INFORMATION: Synthetic Sequence

<400> SEQUENCE: 2
atgtcggact cagaagtcaa tcaagaagct aagccagagg tcaagccaga agtcaagcct      60
gagactcaca tcaatttaaa ggtgtccgat ggatcttcag agatcttctt caagatcaaa     120
aagaccactc ctttaagaag gctgatggaa gcgttcgcta aaagacaggg taaggaaatg     180
gactccttaa gattcttgta cgacggtatt agaattcaag ctgatcaggc ccctgaagat     240
ttggacatgg aggataacga tattattgag gctcacagag aacagattgg tggt           294

<210> SEQ ID NO 3
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 3

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

```
Gln Ala Asp Gln Ala Pro Glu Asp Leu Asp Met Glu Asp Asn Asp Ile
            85                  90                  95

Ile Glu Ala His Arg Glu Gln Ile Gly Gly
            100                 105

<210> SEQ ID NO 4
<211> LENGTH: 321
<212> TYPE: DNA
<213> ORGANISM: Artificial Sequence
<220> FEATURE:
<223> OTHER INFORMATION: Synthetic Sequence

<400> SEQUENCE: 4
atgggtcatc accatcatca tcacgggtcg gactcagaag tcaatcaaga agctaagcca        60
gaggtcaagc cagaagtcaa gcctgagact cacatcaatt taaaggtgtc cgatggatct       120
tcagagatct tcttcaagat caaaaagacc actcctttaa aaggctgat ggaagcgttc        180 gctaaaagac agggtaagga atggactcc ttaagattct tgtacgacgg tattagaatt       240
caagctgatc aggcccctga agatttggac atggaggata cgatattat tgaggctcac        300 agagaacaga ttggaggttg a                                                 321

<210> SEQ ID NO 5
<211> LENGTH: 54
<212> TYPE: PRT
<213> ORGANISM: Artificial Sequence
<220> FEATURE:
<223> OTHER INFORMATION: Synthetic Sequence

<400> SEQUENCE: 5

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys
    50

<210> SEQ ID NO 6
<211> LENGTH: 165
<212> TYPE: DNA
<213> ORGANISM: Artificial Sequence
<220> FEATURE:
<223> OTHER INFORMATION: Synthetic Sequence

<400> SEQUENCE: 6
atgtcggact cagaagtcaa tcaagaagct aagccagagg tcaagccaga agtcaagcct        60
gagactcaca tcaatttaaa ggtgtccgat ggatcttcag agatcttctt caagatcaaa       120
aagaccactc ctttaagaag gctgatggaa gcgttcgcta aatga                       165

<210> SEQ ID NO 7
<211> LENGTH: 62
<212> TYPE: PRT
<213> ORGANISM: Artificial Sequence
<220> FEATURE:
<223> OTHER INFORMATION: Synthetic Sequence

<400> SEQUENCE: 7

Met Gly His His His His His His Gly Ser Asp Ser Glu Val Asn Gln
1               5                   10                  15
```

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
            35                  40                  45

Lys Thr Thr Pro Leu Arg Arg Leu Met Glu Ala Phe Ala Lys
        50                  55                  60

<210> SEQ ID NO 8
<211> LENGTH: 189
<212> TYPE: DNA
<213> ORGANISM: Artificial Sequence
<220> FEATURE:
<223> OTHER INFORMATION: Synthetic Sequence

<400> SEQUENCE: 8
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaatga                                                            189

<210> SEQ ID NO 9
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 9

Met Lys Arg Gln Gly Lys Glu Met Asp Ser Leu Arg Phe Leu Tyr Asp
  1               5                  10                  15

Gly Ile Arg Ile Gln Ala Asp Gln Ala Pro Glu Asp Leu Asp Met Glu
            20                  25                  30

Asp Asn Asp Ile Ile Glu Ala His Arg Glu Gln Ile Gly Gly
            35                  40                  45

<210> SEQ ID NO 10
<211> LENGTH: 141
<212> TYPE: DNA
<213> ORGANISM: Artificial Sequence
<220> FEATURE:
<223> OTHER INFORMATION: Synthetic Sequence

<400> SEQUENCE: 10
atgaaaagac agggtaagga aatggactcc ttaagattct gtacgacgg tattagaatt       60 caagctgatc aggcccctga agatttggac atggaggata cgatattat tgaggctcac      120 agagaacaga ttggaggttg a                                                141

<210> SEQ ID NO 11
<211> LENGTH: 53
<212> TYPE: PRT
<213> ORGANISM: Artificial Sequence
<220> FEATURE:
<223> OTHER INFORMATION: Synthetic Sequence

<400> SEQUENCE: 11

Met Gly His His His His His His Lys Arg Gln Gly Lys Glu Met Asp
  1               5                  10                  15

Ser Leu Arg Phe Leu Tyr Asp Gly Ile Arg Ile Gln Ala Asp Gln Thr
            20                  25                  30

Pro Glu Asp Leu Asp Met Glu Asp Asn Asp Ile Ile Glu Ala His Arg

<210> SEQ ID NO 12
<211> LENGTH: 162
<212> TYPE: DNA
<213> ORGANISM: Artificial Sequence
<220> FEATURE:
<223> OTHER INFORMATION: Synthetic Sequence

<400> SEQUENCE: 12

```
atgggtcatc accatcatca tcacaaaaga cagggtaagg aaatggactc cttaagattc      60
ttgtacgacg gtattagaat tcaagctgat cagacccctg aagatttgga catggaggat     120
aacgatatta ttgaggctca cagagaacag attggaggtt ga                        162
```

<210> SEQ ID NO 13
<211> LENGTH: 239
<212> TYPE: PRT
<213> ORGANISM: Artificial Sequence
<220> FEATURE:
<223> OTHER INFORMATION: Synthetic Sequence

<400> SEQUENCE: 13

```
Met Val Ser Lys Gly Glu Glu Leu Phe Thr Gly Val Val Pro Ile Leu
  1               5                  10                  15
Val Glu Leu Asp Gly Asp Val Asn Gly His Lys Phe Ser Val Ser Gly
             20                  25                  30
Glu Gly Glu Gly Asp Ala Thr Tyr Gly Lys Leu Thr Leu Lys Phe Ile
         35                  40                  45
Cys Thr Thr Gly Lys Leu Pro Val Pro Trp Pro Thr Leu Val Thr Thr
     50                  55                  60
Leu Thr Tyr Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys
225                 230                 235
```

<210> SEQ ID NO 14
<211> LENGTH: 720

<212> TYPE: DNA
<213> ORGANISM: Artificial Sequence
<220> FEATURE:
<223> OTHER INFORMATION: Synthetic Sequence

<400> SEQUENCE: 14

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 15
<211> LENGTH: 248
<212> TYPE: PRT
<213> ORGANISM: Artificial Sequence
<220> FEATURE:
<223> OTHER INFORMATION: Synthetic Sequence

<400> SEQUENCE: 15

```
Met Gly His His His His His Gly Met Val Ser Lys Gly Glu Glu
  1               5                  10                  15

Leu Phe Thr Gly Val Val Pro Ile Leu Val Glu Leu Asp Gly Asp Val
             20                  25                  30

Asn Gly His Lys Phe Ser Val Ser Gly Glu Gly Glu Gly Asp Ala Thr
         35                  40                  45

Tyr Gly Lys Leu Thr Leu Lys Phe Ile Cys Thr Thr Gly Lys Leu Pro
     50                  55                  60

Val Pro Trp Pro Thr Leu Val Thr Thr Leu Thr Tyr Gly Val Gln Cys
 65                  70                  75                  80

Phe Ser Arg Tyr Pro Asp His Met Lys Gln His Asp Phe Phe Lys Ser
                 85                  90                  95

Ala Met Pro Glu Gly Tyr Val Gln Glu Arg Thr Ile Phe Phe Lys Asp
            100                 105                 110

Asp Gly Asn Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Tyr Asn Ser His Asn Val
145                 150                 155                 160

Tyr Ile Met Ala Asp Lys Gln Lys Asn Gly Ile Lys Val Asn Phe Lys
                165                 170                 175

Ile Arg His Asn Ile Glu Asp Gly Ser Val Gln Leu Ala Asp His Tyr
            180                 185                 190

Gln Gln Asn Thr Pro Ile Gly Asp Gly Pro Val Leu Leu Pro Asp Asn
        195                 200                 205
```

His Tyr Leu Ser Thr Gln Ser Ala Leu Ser Lys Asp Pro Asn Glu Lys
    210                 215                 220

Arg Asp His Met Val Leu Leu Glu Phe Val Thr Ala Ala Gly Ile Thr
225                 230                 235                 240

Leu Gly Met Asp Glu Leu Tyr Lys
            245

<210> SEQ ID NO 16
<211> LENGTH: 747
<212> TYPE: DNA
<213> ORGANISM: Artificial Sequence
<220> FEATURE:
<223> OTHER INFORMATION: Synthetic Sequence

<400> SEQUENCE: 16
atgggtcatc accatcatca tcacgggatg gtgagcaagg gcgaggagct gttcaccggg    60
gtggtgccca tcctggtcga gctggacggc gacgtaaacg gccacaagtt cagcgtgtcc   120
ggcgagggcg agggcgatgc cacctacggc aagctgaccc tgaagttcat ctgcaccacc   180
ggcaagctgc ccgtgccctg cccaccctc gtgaccaccc tgacctacgg cgtgcagtgc    240
ttcagccgct accccgacca catgaagcag cacgacttct tcaagtccgc catgcccgaa   300
ggctacgtcc aggagcgcac catcttcttc aaggacgacg gcaactacaa gacccgcgcc   360
gaggtgaagt tcgagggcga caccctggtg aaccgcatcg agctgaaggg catcgacttc   420
aaggaggacg gcaacatcct ggggcacaag ctggagtaca actacaacag ccacaacgtc   480
tatatcatgg ccgacaagca gaagaacggc atcaaggtga acttcaagat ccgccacaac   540
atcgaggacg gcagcgtgca gctcgccgac cactaccagc agaacacccc catcggcgac   600
ggccccgtgc tgctgcccga caaccactac ctgagcaccc agtccgccct gagcaaagac   660
cccaacgaga gcgcgatca catggtcctg ctggagttcg tgaccgccgc cgggatcact   720
ctcggcatgg acgagctgta caagtaa                                      747

<210> SEQ ID NO 17
<211> LENGTH: 345
<212> TYPE: PRT
<213> ORGANISM: Artificial Sequence
<220> FEATURE:
<223> OTHER INFORMATION: Synthetic Sequence

<400> SEQUENCE: 17

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
            85                  90                  95

Ile Glu Ala His Arg Glu Gln Ile Gly Gly Met Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
    130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Leu Thr Tyr Gly Val Gln
                165                 170                 175

Cys Phe Ser Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
    290                 295                 300

Asn His Tyr Leu Ser Thr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Glu Leu Tyr Lys
            340                 345

<210> SEQ ID NO 18
<211> LENGTH: 1038
<212> TYPE: DNA
<213> ORGANISM: Artificial Sequence
<220> FEATURE:
<223> OTHER INFORMATION: Synthetic Sequence

<400> SEQUENCE: 18
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaaagac agggtaagga aatggactcc ttaagattct tgtacgacgg tattagaatt     240
caagctgatc aggcccctga agatttggac atggaggata cgatattat tgaggctcac      300 agagaacaga ttggaggtat ggtgagcaag ggcgaggagc tgttcaccgg ggtggtgccc     360
atcctggtcg agctggacgg cgacgtaaac ggccacaagt tcagcgtgtc cggcgagggc     420
gagggcgatg ccacctacgg caagctgacc ctgaagttca tctgcaccac cggcaagctg     480
cccgtgccct ggcccaccct cgtgaccacc ctgacctacg gcgtgcagtg cttcagccgc     540
taccccgacc acatgaagca gcacgacttc ttcaagtccg ccatgcccga aggctacgtc     600
caggagcgca ccatcttctt caaggacgac ggcaactaca agacccgcgc cgaggtgaag     660
ttcgagggcg acaccctggt gaaccgcatc gagctgaagg gcatcgactt caaggaggac     720
ggcaacatcc tggggcacaa gctggagtac aactacaaca gccacaacgt ctatatcatg     780

```
gccgacaagc agaagaacgg catcaaggtg aacttcaaga tccgccacaa catcgaggac    840
ggcagcgtgc agctcgccga ccactaccag cagaacaccc ccatcggcga cggccccgtg    900
ctgctgcccg acaaccacta cctgagcacc cagtccgccc tgagcaaaga ccccaacgag    960
aagcgcgatc acatggtcct gctggagttc gtgaccgccg ccgggatcac tctcggcatg   1020
gacgagctgt acaagtaa                                                  1038
```

```
<210> SEQ ID NO 19
<211> LENGTH: 292
<212> TYPE: PRT
<213> ORGANISM: Artificial Sequence
<220> FEATURE:
<223> OTHER INFORMATION: Synthetic Sequence

<400> SEQUENCE: 19

Met Gly His His His His His His Lys Arg Gln Gly Lys Glu Met Asp
  1               5                  10                  15

Ser Leu Arg Phe Leu Tyr Asp Gly Ile Arg Ile Gln Ala Asp Gln Ala
             20                  25                  30

Pro Glu Asp Leu Asp Met Glu Asp Asn Asp Ile Ile Glu Ala His Arg
         35                  40                  45

Glu Gln Ile Gly Gly Met Val Ser Lys Gly Glu Glu Leu Phe Thr Gly
     50                  55                  60

Val Val Pro Ile Leu Val Glu Leu Asp Gly Asp Val Asn Gly His Lys
 65                  70                  75                  80

Phe Ser Val Ser Gly Glu Gly Glu Gly Asp Ala Thr Tyr Gly Lys Leu
                 85                  90                  95

Thr Leu Lys Phe Ile Cys Thr Thr Gly Lys Leu Pro Val Pro Trp Pro
            100                 105                 110

Thr Leu Val Thr Thr Leu Thr Tyr Gly Val Gln Cys Phe Ser Arg Tyr
        115                 120                 125

Pro Asp His Met Lys Gln His Asp Phe Phe Lys Ser Ala Met Pro Glu
    130                 135                 140

Gly Tyr Val Gln Glu Arg Thr Ile Phe Phe Lys Asp Asp Gly Asn Tyr
145                 150                 155                 160

Lys Thr Arg Ala Glu Val Lys Phe Glu Gly Asp Thr Leu Val Asn Arg
                165                 170                 175

Ile Glu Leu Lys Gly Ile Asp Phe Lys Glu Asp Gly Asn Ile Leu Gly
            180                 185                 190

His Lys Leu Glu Tyr Asn Tyr Asn Ser His Asn Val Tyr Ile Met Ala
        195                 200                 205

Asp Lys Gln Lys Asn Gly Ile Lys Val Asn Phe Lys Ile Arg His Asn
    210                 215                 220

Ile Glu Asp Gly Ser Val Gln Leu Ala Asp His Tyr Gln Gln Asn Thr
225                 230                 235                 240

Pro Ile Gly Asp Gly Pro Val Leu Leu Pro Asp Asn His Tyr Leu Ser
                245                 250                 255

Thr Gln Ser Ala Leu Ser Lys Asp Pro Asn Glu Lys Arg Asp His Met
            260                 265                 270

Val Leu Leu Glu Phe Val Thr Ala Ala Gly Ile Thr Leu Gly Met Asp
        275                 280                 285

Glu Leu Tyr Lys
    290

<210> SEQ ID NO 20
```

<211> LENGTH: 879
<212> TYPE: DNA
<213> ORGANISM: Artificial Sequence
<220> FEATURE:
<223> OTHER INFORMATION: Synthetic Sequence

<400> SEQUENCE: 20

| | | | | | |
|---|---|---|---|---|---|
| atgggtcatc | accatcatca | tcacaaaaga | cagggtaagg | aaatggactc | cttaagattc | 60
| ttgtacgacg | gtattagaat | tcaagctgat | caggccctg | aagatttgga | catggaggat | 120
| aacgatatta | ttgaggctca | cagagaacag | attggaggta | tggtgagcaa | gggcgaggag | 180
| ctgttcaccg | gggtggtgcc | catcctggtc | gagctggacg | gcgacgtaaa | cggccacaag | 240
| ttcagcgtgt | ccggcgaggg | cgagggcgat | gccacctacg | gcaagctgac | cctgaagttc | 300
| atctgcacca | ccggcaagct | gcccgtgccc | tggcccaccc | tcgtgaccac | cctgacctac | 360
| ggcgtgcagt | gcttcagccg | ctaccccgac | cacatgaagc | agcacgactt | cttcaagtcc | 420
| gccatgcccg | aaggctacgt | ccaggagcgc | accatcttct | tcaaggacga | cggcaactac | 480
| aagacccgcg | ccgaggtgaa | gttcgagggc | gacaccctgg | tgaaccgcat | cgagctgaag | 540
| ggcatcgact | tcaaggagga | cggcaacatc | ctggggcaca | agctggagta | caactacaac | 600
| agccacaacg | tctatatcat | ggccgacaag | cagaagaacg | gcatcaaggt | gaacttcaag | 660
| atccgccaca | acatcgagga | cggcagcgtg | cagctcgccg | accactacca | gcagaacacc | 720
| cccatcggcg | acggccccgt | gctgctgccc | gacaaccact | acctgagcac | ccagtccgcc | 780
| ctgagcaaag | accccaacga | gaagcgcgat | cacatggtcc | tgctggagtt | cgtgaccgcc | 840
| gccgggatca | ctctcggcat | ggacgagctg | tacaagtaa | | | 879

<210> SEQ ID NO 21
<211> LENGTH: 236
<212> TYPE: PRT
<213> ORGANISM: Artificial Sequence
<220> FEATURE:
<223> OTHER INFORMATION: Synthetic Sequence

<400> SEQUENCE: 21

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu

```
                  165                 170                 175
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Thr Ser Gly Ser Gly Gly Gly
    210                 215                 220

Gly Gly Trp Met Ser Glu Asn Leu Tyr Phe Gln Gly
225                 230                 235
```

<210> SEQ ID NO 22
<211> LENGTH: 711
<212> TYPE: DNA
<213> ORGANISM: Artificial Sequence
<220> FEATURE:
<223> OTHER INFORMATION: Synthetic Sequence

<400> SEQUENCE: 22

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg agtttcccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aactagtgga    660
tctggtggtg gtggcggatg gatgagcgag aatctttatt ttcaaggttg a              711
```

<210> SEQ ID NO 23
<211> LENGTH: 582
<212> TYPE: PRT
<213> ORGANISM: Artificial Sequence
<220> FEATURE:
<223> OTHER INFORMATION: Synthetic Sequence

<400> SEQUENCE: 23

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110
```

-continued

```
Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Thr Ser Gly Ser Gly Gly Gly
        210                 215                 220

Gly Gly Trp Met Ser Glu Asn Leu Tyr Phe Gln Gly Ala Met Gly His
225                 230                 235                 240

His His His His His Gly Ser Asp Ser Glu Val Asn Gln Glu Ala Lys
                245                 250                 255

Pro Glu Val Lys Pro Glu Val Lys Pro Glu Thr His Ile Asn Leu Lys
            260                 265                 270

Val Ser Asp Gly Ser Ser Glu Ile Phe Phe Lys Ile Lys Lys Thr Thr
        275                 280                 285

Pro Leu Arg Arg Leu Met Glu Ala Phe Ala Lys Arg Gln Gly Lys Glu
        290                 295                 300

Met Asp Ser Leu Arg Phe Leu Tyr Asp Gly Ile Arg Ile Gln Ala Asp
305                 310                 315                 320

Gln Ala Pro Glu Asp Leu Asp Met Glu Asp Asn Asp Ile Ile Glu Ala
                325                 330                 335

His Arg Glu Gln Ile Gly Gly Met Val Ser Lys Gly Glu Glu Leu Phe
            340                 345                 350

Thr Gly Val Val Pro Ile Leu Val Glu Leu Asp Gly Asp Val Asn Gly
        355                 360                 365

His Lys Phe Ser Val Ser Gly Glu Gly Glu Gly Asp Ala Thr Tyr Gly
        370                 375                 380

Lys Leu Thr Leu Lys Phe Ile Cys Thr Thr Gly Lys Leu Pro Val Pro
385                 390                 395                 400

Trp Pro Thr Leu Val Thr Thr Leu Thr Tyr Gly Val Gln Cys Phe Ser
                405                 410                 415

Arg Tyr Pro Asp His Met Lys Gln His Asp Phe Phe Lys Ser Ala Met
            420                 425                 430

Pro Glu Gly Tyr Val Gln Glu Arg Thr Ile Phe Phe Lys Asp Asp Gly
        435                 440                 445

Asn Tyr Lys Thr Arg Ala Glu Val Lys Phe Glu Gly Asp Thr Leu Val
        450                 455                 460

Asn Arg Ile Glu Leu Lys Gly Ile Asp Phe Lys Glu Asp Gly Asn Ile
465                 470                 475                 480

Leu Gly His Lys Leu Glu Tyr Asn Tyr Asn Ser His Asn Val Tyr Ile
                485                 490                 495

Met Ala Asp Lys Gln Lys Asn Gly Ile Lys Val Asn Phe Lys Ile Arg
            500                 505                 510

His Asn Ile Glu Asp Gly Ser Val Gln Leu Ala Asp His Tyr Gln Gln
        515                 520                 525

Asn Thr Pro Ile Gly Asp Gly Pro Val Leu Leu Pro Asp Asn His Tyr
```

```
        530             535             540
Leu Ser Thr Gln Ser Ala Leu Ser Lys Asp Pro Asn Glu Lys Arg Asp
545                 550                 555                 560

His Met Val Leu Leu Glu Phe Val Thr Ala Ala Gly Ile Thr Leu Gly
                565                 570                 575

Met Asp Glu Leu Tyr Lys
            580

<210> SEQ ID NO 24
<211> LENGTH: 1749
<212> TYPE: DNA
<213> ORGANISM: Artificial Sequence
<220> FEATURE:
<223> OTHER INFORMATION: Synthetic Sequence

<400> SEQUENCE: 24 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aactagtgga    660
tctggtggtg gtggcggatg gatgagcgag aatctttatt ttcaaggtgc catgggtcat    720
caccatcatc atcacgggtc ggactcagaa gtcaatcaag aagctaagcc agaggtcaag    780
ccagaagtca agcctgagac tcacatcaat ttaaaggtgt ccgatggatc ttcagagatc    840
ttcttcaaga tcaaaaagac cactcctta agaaggctga tggaagcgtt cgctaaaaga    900
cagggtaagg aaatggactc cttaagattc ttgtacgacg gtattagaat tcaagctgat    960
caggcccctg aagatttgga catggaggat aacgatatta ttgaggctca ccgcgaacag   1020
attggaggta tggtgagcaa gggcgaggag ctgttcaccg gggtggtgcc catcctggtc   1080
gagctggacg gcgacgtaaa cggccacaag ttcagcgtgt ccggcgaggg cgagggcgat   1140
gccacctacg gcaagctgac cctgaagttc atctgcacca ccggcaagct gcccgtgccc   1200
tggcccaccc tcgtgaccac cctgacctac ggcgtgcagt gcttcagccg ctaccccgac   1260
cacatgaagc agcacgactt cttcaagtcc gccatgcccg aaggctacgt ccaggagcgc   1320
accatcttct tcaaggacga cggcaactac aagacccgcg ccgaggtgaa gttcgagggc   1380
gacaccctgg tgaaccgcat cgagctgaag ggcatcgact tcaaggagga cggcaacatc   1440
ctggggcaca gctggagta caactacaac agccacaacg tctatatcat ggccgacaag   1500
cagaagaacg gcatcaaggt gaacttcaag atccgccaca acatcgagga cggcagcgtg   1560
cagctcgccg accactacca gcagaacacc cccatcggcg acggccccgt gctgctgccc   1620
gacaaccact acctgagcac ccagtccgcc ctgagcaaag accccaacga gaagcgcgat   1680
cacatggtcc tgctggagtt cgtgaccgcc gccgggatca ctctcggcat ggacgagctg   1740
``` tacaagtaa                                                            1749

<210> SEQ ID NO 25
<211> LENGTH: 530
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: 358
<223> OTHER INFORMATION: Xaa = any amino acid

<400> SEQUENCE: 25

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Thr Ser Gly Ser Gly Gly Gly
    210                 215                 220

Gly Gly Trp Met Ser Glu Asn Leu Tyr Phe Gln Gly Ala His Met Gly
225                 230                 235                 240

His His His His His His Lys Arg Gln Gly Lys Glu Met Asp Ser Leu
                245                 250                 255

Arg Phe Leu Tyr Asp Gly Ile Arg Ile Gln Ala Asp Gln Ala Pro Glu
            260                 265                 270

Asp Leu Asp Met Glu Asp Asn Asp Ile Ile Glu Ala His Arg Glu Gln
        275                 280                 285

Ile Gly Gly Met Val Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335
```

-continued

```
Lys Leu Ile Cys Thr Thr Gly Lys Leu Pro Val Pro Trp Pro Thr Leu
            340                 345                 350
Val Thr Thr Leu Gly Xaa Gly Leu Gln Cys Phe Ala Arg Tyr Pro Asp
        355                 360                 365
His Met Lys Gln His Asp Phe Phe Lys Ser Ala Met Pro Glu Gly Tyr
    370                 375                 380
Val Gln Glu Arg Thr Ile Phe Phe Lys Asp Asp Gly Asn Tyr Lys Thr
385                 390                 395                 400
Arg Ala Glu Val Lys Phe Glu Gly Asp Thr Leu Val Asn Arg Ile Glu
                405                 410                 415
Leu Lys Gly Ile Asp Phe Lys Glu Asp Gly Asn Ile Leu Gly His Lys
            420                 425                 430
Leu Glu Tyr Asn Tyr Asn Ser His Asn Val Tyr Ile Thr Ala Asp Lys
        435                 440                 445
Gln Lys Asn Gly Ile Lys Ala Asn Phe Lys Ile Arg His Asn Ile Glu
    450                 455                 460
Asp Gly Gly Val Gln Leu Ala Asp His Tyr Gln Gln Asn Thr Pro Ile
465                 470                 475                 480
Gly Asp Gly Pro Val Leu Leu Pro Asp Asn His Tyr Leu Ser Tyr Gln
                485                 490                 495
Ser Ala Leu Ser Lys Asp Pro Asn Glu Lys Arg Asp His Met Val Leu
            500                 505                 510
Leu Glu Phe Val Thr Ala Ala Gly Ile Thr His Gly Met Asp Glu Leu
        515                 520                 525
Tyr Lys
    530

<210> SEQ ID NO 26
<211> LENGTH: 1587
<212> TYPE: DNA
<213> ORGANISM: Artificial Sequence
<220> FEATURE:
<223> OTHER INFORMATION: Synthetic Sequence

<400> SEQUENCE: 26
atgtccccta ctactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggtttg      300 gatattagat acgtgttttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aactagtgga     660
tctggtggtg gtgcggatg gatgagcgag aatctttatt ttcaaggtgc catgggtcat     720
caccatcatc atcacagaca gggtaaggaa atggactcct taagattctt gtacgacggt     780
attgaaattc aagctgatca ggcccctgaa gatttggaca tggaggataa cgatattatt     840
gaggctcacc gcgaacagat tggaggtatg gtgagcaagg gcgaggagct gttcaccggg     900
```

```
gtggtgccca tcctggtcga gctggacggc gacgtaaacg gccacaagtt cagcgtgtcc    960
ggcgagggcg agggcgatgc cacctacggc aagctgaccc tgaagttcat ctgcaccacc   1020
ggcaagctgc ccgtgccctg cccaccctc gtgaccaccc tgacctacgg cgtgcagtgc   1080
ttcagccgct accccgacca catgaagcag cacgacttct tcaagtccgc catgcccgaa   1140
ggctacgtcc aggagcgcac catcttcttc aaggacgacg gcaactacaa gacccgcgcc   1200
gaggtgaagt tcgagggcga caccctggtg aaccgcatcg agctgaaggg catcgacttc   1260
aaggaggacg gcaacatcct ggggcacaag ctggagtaca actacaacag ccacaacgtc   1320
tatatcatgg ccgacaagca gaagaacggc atcaaggtga acttcaagat ccgccacaac   1380
atcgaggacg gcagcgtgca gctcgccgac cactaccagc agaacacccc catcggcgac   1440
ggccccgtgc tgctgcccga caaccactac ctgagcaccc agtccgccct gagcaaagac   1500
cccaacgaga gcgcgatca catggtcctg ctggagttcg tgaccgccgc cgggatcact   1560
ctcggcatgg acgagctgta caagtaa                                        1587
```

<210> SEQ ID NO 27
<211> LENGTH: 63
<212> TYPE: PRT
<213> ORGANISM: Artificial Sequence
<220> FEATURE:
<223> OTHER INFORMATION: Synthetic Sequence

<400> SEQUENCE: 27

```
Met Gly Cys His His His His His His Gly Ser Asp Ser Glu Val Asn
  1               5                  10                  15

Gln Glu Ala Lys Pro Glu Val Lys Pro Glu Val Lys Pro Glu Thr His
             20                  25                  30

Ile Asn Leu Lys Val Ser Asp Gly Ser Ser Glu Ile Phe Phe Lys Ile
         35                  40                  45

Lys Lys Thr Thr Pro Leu Arg Arg Leu Met Glu Ala Phe Ala Lys
     50                  55                  60
```

<210> SEQ ID NO 28
<211> LENGTH: 192
<212> TYPE: DNA
<213> ORGANISM: Artificial Sequence
<220> FEATURE:
<223> OTHER INFORMATION: Synthetic Sequence

<400> SEQUENCE: 28

```
atgggttgcc atcaccatca tcatcacggg tcggactcag aagtcaatca agaagctaag    60
ccagaggtca agccagaagt caagcctgag actcacatca atttaaaggt gtccgatgga   120
tcttcagaga tcttcttcaa gatcaaaaag accactcctt taagaaggct gatggaagcg   180
ttcgctaaat ga                                                        192
```

<210> SEQ ID NO 29
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 29

```
Leu Val Pro Glu Leu Asn Glu Lys Asp Asp Asp Gln Val Gln Lys Ala
  1               5                  10                  15

Leu Ala Ser Arg Glu Asn Thr Gln Leu Met Asn Arg Asp Asn Ile Glu
             20                  25                  30
```

```
Ile Thr Val Arg Asp Phe Lys Thr Leu Ala Pro Arg Arg Trp Leu Asn
             35                  40                  45

Asp Thr Ile Ile Glu Phe Phe Met Lys Tyr Ile Glu Lys Ser Thr Pro
 50                  55                  60

Asn Thr Val Ala Phe Asn Ser Phe Phe Tyr Thr Asn Leu Ser Glu Arg
 65                  70                  75                  80

Gly Tyr Gln Gly Val Arg Arg Trp Met Lys Arg Lys Lys Thr Gln Ile
                 85                  90                  95

Asp Lys Leu Asp Lys Ile Phe Thr Pro Ile Asn Leu Asn Gln Ser His
            100                 105                 110

Trp Ala Leu Gly Ile Ile Asp Leu Lys Lys Thr Ile Gly Tyr Val
            115                 120                 125

Asp Ser Leu Ser Asn Gly Pro Asn Ala Met Ser Phe Ala Ile Leu Thr
130                 135                 140

Asp Leu Gln Lys Tyr Val Met Glu Ser Lys His Thr Ile Gly Glu
145                 150                 155                 160

Asp Phe Asp Leu Ile His Leu Asp Cys Pro Gln Gln Pro Asn Gly Tyr
                165                 170                 175

Asp Cys Gly Ile Tyr Val Cys Met Asn Thr Leu Tyr Gly Ser Ala Asp
            180                 185                 190

Ala Pro Leu Asp Phe Asp Tyr Lys Asp Ala Ile Arg Met Arg Arg Phe
        195                 200                 205

Ile Ala His Leu Ile Leu Thr Asp Ala Leu Lys
    210                 215

<210> SEQ ID NO 30
<211> LENGTH: 657
<212> TYPE: DNA
<213> ORGANISM: Artificial Sequence
<220> FEATURE:
<223> OTHER INFORMATION: Synthetic Sequence

<400> SEQUENCE: 30
cttgttcctg aattaaatga aaagacgat gaccaagtac aaaaagcttt ggcatctaga     60
gaaaatactc agttaatgaa tagagataat atagagataa cagtacgtga ttttaagacc    120
ttggcaccac gaagatggct aaatgacact atcattgagt ttttttatgaa atacattgaa   180 aaatctaccc ctaatacagt ggcgtttaat tcatttttct ataccaattt atcagaaagg    240
ggttatcaag cgtccggag gtggatgaag agaaagaaga cacaaattga taaacttgat     300
aaaatcttta caccaataaa tttgaaccaa tcccactggg cgttgggcat aattgattta    360
aaaaagaaaa ctataggtta cgtagattca ttatcgaatg gtccaaatgc tatgagtttc    420
gctatactga ctgacttgca aaaatatgtt atggaggaaa gtaagcatac aataggagaa    480
gactttgatt tgattcattt agattgtccg cagcaaccaa atggctacga ctgtggaata    540
tatgtttgta tgaatactct ctatggaagt gcagatgcgc cattggattt tgattataaa    600
gatgcgatta ggatgagaag atttattgcc catttgattt taaccgacgc tttaaaa      657

<210> SEQ ID NO 31
<211> LENGTH: 42
<212> TYPE: PRT
<213> ORGANISM: Artificial Sequence
<220> FEATURE:
<223> OTHER INFORMATION: Synthetic Sequence

<400> SEQUENCE: 31
```

```
Met Lys Glu Met Asp Ser Leu Arg Phe Leu Tyr Asp Gly Ile Arg Ile
 1               5                  10                  15

Gln Ala Asp Gln Ala Pro Glu Asp Leu Asp Met Glu Asp Asn Asp Ile
                20                  25                  30

Ile Glu Ala His Arg Glu Gln Ile Gly Gly
        35                  40
```

```
<210> SEQ ID NO 32
<211> LENGTH: 129
<212> TYPE: DNA
<213> ORGANISM: Artificial Sequence
<220> FEATURE:
<223> OTHER INFORMATION: Synthetic Sequence

<400> SEQUENCE: 32
atgaaggaaa tggactcctt aagattcttg tacgacggta ttagaattca agctgatcag      60 gccccctgaag atttggacat ggaggataac gatattattg aggctcacag agaacagatt    120
ggaggttga                                                             129

<210> SEQ ID NO 33
<211> LENGTH: 49
<212> TYPE: PRT
<213> ORGANISM: Artificial Sequence
<220> FEATURE:
<223> OTHER INFORMATION: Synthetic Sequence

<400> SEQUENCE: 33
```

```
Met Gly His His His His His His Lys Glu Met Asp Ser Leu Arg Phe
 1               5                  10                  15

Leu Tyr Asp Gly Ile Arg Ile Gln Ala Asp Gln Ala Pro Glu Asp Leu
                20                  25                  30

Asp Met Glu Asp Asn Asp Ile Ile Glu Ala His Arg Glu Gln Ile Gly
        35                  40                  45

Gly
```

```
<210> SEQ ID NO 34
<211> LENGTH: 150
<212> TYPE: DNA
<213> ORGANISM: Artificial Sequence
<220> FEATURE:
<223> OTHER INFORMATION: Synthetic Sequence

<400> SEQUENCE: 34
atgggtcatc accatcatca tcacaaggaa atggactcct taagattctt gtacgacggt      60
attagaattc aagctgatca ggccccctgaa gatttggaca tggaggataa cgatattatt    120
gaggctcaca gagaacagat tggaggttga                                      150

<210> SEQ ID NO 35
<211> LENGTH: 478
<212> TYPE: DNA
<213> ORGANISM: Artificial Sequence
<220> FEATURE:
<223> OTHER INFORMATION: Synthetic Sequence

<400> SEQUENCE: 35
agatctcgat cccgcgaaat taatacgact cactataggg gaattgtgag cggataacaa      60
ttcccctcta gaaataattt tgtttaactt taagaaggag atataccatg ggtcatcacc    120
atcatcatca cggtcggac tcagaagtca atcaagaagc taagcagag gtcaagccag      180 aagtcaagcc tgagactcac atcaatttaa aggtgtccga tggatcttca gagatcttct    240
```

```
tcaagatcaa aaagaccact cctttaagaa ggctgatgga agcgttcgct aaaagacagg      300
gtaaggaaat ggactcctta agattcttgt acgacggtat tagaattcaa gctgatcagg      360
cccctgaaga tttggacatg gaggataacg atattattga ggctcaccgc gaacagattg      420
gaggttgaga ccggatccga attcgagctc cgtcgacaag cttgcggccg cactcgag        478
```

<210> SEQ ID NO 36
<211> LENGTH: 319
<212> TYPE: DNA
<213> ORGANISM: Artificial Sequence
<220> FEATURE:
<223> OTHER INFORMATION: Synthetic Sequence

<400> SEQUENCE: 36

```
agatctcgat cccgcgaaat taatacgact cactataggg gaattgtgag cggataacaa       60
ttcccctcta gaaataattt tgtttaactt taagaaggag atataccatg ggtcatcacc      120
atcatcatca caaaagacag ggtaaggaaa tggactcctt aagattcttg tacgacggta      180
ttagaattca gctgatcag accctgaag atttggacat ggaggataac gatattattg      240
aggctcaccg cgaacagatt ggaggttgag accggatccg aattcgagct ccgtcgacaa      300
gcttgcggcc gcactcgag                                                    319
```

<210> SEQ ID NO 37
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 37

```
Met Leu Ile Lys Val Lys Thr Leu Thr Gly Lys Glu Ile Glu Ile Asp
 1               5                  10                  15

Ile Glu Pro Thr Asp Lys Val Glu Arg Ile Lys Glu Arg Val Glu Glu
             20                  25                  30
```

<210> SEQ ID NO 38
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 38

```
Lys Glu Gly Ile Pro Pro Gln Gln Gln Arg Leu Ile Tyr Ser Gly Lys
 1               5                  10                  15

Gln Met Asn Asp Glu Lys Thr Ala Ala Asp Tyr Lys Ile Leu Gly Gly
             20                  25                  30
```

<210> SEQ ID NO 39
<211> LENGTH: 39
<212> TYPE: PRT
<213> ORGANISM: Artificial Sequence
<220> FEATURE:
<223> OTHER INFORMATION: Synthetic Sequence

<400> SEQUENCE: 39

```
Met Leu Ile Lys Val Lys Thr Leu Thr Gly Lys Glu Ile Glu Ile Asp
 1               5                  10                  15

Ile Glu Pro Thr Asp Lys Val Glu Arg Ile Lys Glu Arg Val Glu Glu
             20                  25                  30
```

-continued

```
Lys Glu Gly Ile Pro Pro Gln
        35

<210> SEQ ID NO 40
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 40

Gln Gln Arg Leu Ile Tyr Ser Gly Lys Gln Met Asn Asp Glu Lys Thr
1               5                   10                  15

Ala Ala Asp Tyr Lys Ile Leu Gly Gly
            20                  25

<210> SEQ ID NO 41
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 41

Met Ile Glu Val Val Val Asn Asp Arg Leu Gly Lys Lys Val Arg Val
1               5                   10                  15

Lys Cys Leu Ala Glu Asp Ser Val Gly Asp Phe Lys Lys Val Leu Ser
            20                  25                  30

<210> SEQ ID NO 42
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 42

Leu Gln Ile Gly Thr Gln Pro Asn Lys Ile Val Leu Gln Lys Gly Gly
1               5                   10                  15

Ser Val Leu Lys Asp His Ile Ser Leu Glu Asp Tyr Glu Val His Asp
            20                  25                  30

Gln Thr Asn Leu Glu Leu Tyr Tyr
        35                  40

<210> SEQ ID NO 43
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 43

Met Ile Glu Val Val Val Asn Asp Arg Leu Gly Lys Lys Val Arg Val
1               5                   10                  15

Lys Cys Leu Ala Glu Asp Ser Val Gly Asp Phe Lys Lys Val Leu Ser
            20                  25                  30

Leu Gln Ile Gly Thr Gln Pro Asn
        35                  40

<210> SEQ ID NO 44
<211> LENGTH: 32
<212> TYPE: PRT
<213> ORGANISM: Artificial Sequence
<220> FEATURE:
```

-continued

<223> OTHER INFORMATION: Synthetic Sequence

<400> SEQUENCE: 44

Lys Ile Val Leu Gln Lys Gly Gly Ser Val Leu Lys Asp His Ile Ser
1               5                   10                  15

Leu Glu Asp Tyr Glu Val His Asp Gln Thr Asn Leu Glu Leu Tyr Tyr
            20                  25                  30

<210> SEQ ID NO 45
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 45

Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
            20                  25                  30

Thr Gln Asn Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly

<210> SEQ ID NO 46
<211> LENGTH: 44
<212> TYPE: PRT
<213> ORGANISM: Artificial Sequence
<220> FEATURE:
<223> OTHER INFORMATION: Synthetic Sequence

<400> SEQUENCE: 46

Leu Glu Gly Val Gln Asp Asp Leu Phe Trp Leu Thr Phe Glu Gly Lys
1               5                   10                  15

Pro Leu Glu Asp Gln Leu Pro Leu Gly Glu Tyr Gly Leu Lys Pro Leu
            20                  25                  30

Ser Thr Val Phe Met Asn Leu Arg Leu Arg Gly Gly
        35                  40

<210> SEQ ID NO 47
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 47

Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
            20                  25                  30

Thr Gln Asn Ile Gly Val His Ala Phe Gln Gln Arg Leu Ala Val His

-continued

```
                35                  40                  45
Pro Ser Gly Val Ala Leu Gln Asp Arg Val Pro Leu Ala Ser Gln Gly
        50                  55                  60

Leu Gly Pro Gly Ser Thr Val Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
                100                 105                 110

Gly Leu Glu Gly Val Gln Asp Asp
            115                 120

<210> SEQ ID NO 48
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 48

Leu Phe Trp Leu Thr Phe Glu Gly Lys Pro Leu Glu Asp Gln Leu Pro
1               5                   10                  15

Leu Gly Glu Tyr Gly Leu Lys Pro Leu Ser Thr Val Phe Met Asn Leu
                20                  25                  30

Arg Leu Arg Gly Gly
            35

<210> SEQ ID NO 49
<211> LENGTH: 137
<212> TYPE: PRT
<213> ORGANISM: Artificial Sequence
<220> FEATURE:
<223> OTHER INFORMATION: Synthetic Sequence

<400> SEQUENCE: 49

Met Ser Arg Ile Leu Glu Ser Glu Asn Glu Thr Glu Ser Asp Glu Ser
1               5                   10                  15

Ser Ile Ile Ser Thr Asn Asn Gly Thr Ala Met Glu Arg Ser Arg Asn
                20                  25                  30

Asn Gln Glu Leu Arg Ser Ser Pro His Thr Val Gln Asn Arg Leu Glu
            35                  40                  45

Leu Phe Ser Arg Arg Leu Ser Gln Leu Gly Leu Ala Ser Asp Ile Ser
        50                  55                  60

Val Asp Gln Gln Val Glu Asp Ser Ser Ser Gly Thr Tyr Glu Gln Glu
65                  70                  75                  80

Glu Thr Ile Lys Thr Asn Ala Gln Thr Ser Lys Gln Lys Ser His Lys
                85                  90                  95

Asp Glu Lys Asn Ile Gln Lys Ile Gln Ile Lys Phe Gln Pro Ile Gly
                100                 105                 110

Ser Ile Gly Gln Leu Lys Pro Ser Val Cys Lys Ile Ser Met Ser Gln
            115                 120                 125

Ser Phe Ala Met Val Ile Leu Phe Leu
        130                 135

<210> SEQ ID NO 50
<211> LENGTH: 49
<212> TYPE: PRT
<213> ORGANISM: Artificial Sequence
<220> FEATURE:
```

<223> OTHER INFORMATION: Synthetic Sequence

<400> SEQUENCE: 50

Lys Arg Arg Leu Lys Met Asp His Val Tyr Cys Tyr Ile Asn Asn Ser
1               5                   10                  15

Phe Ala Pro Ser Pro Gln Gln Asn Ile Gly Glu Leu Trp Met Gln Phe
                20                  25                  30

Lys Thr Asn Asp Glu Leu Ile Val Ser Tyr Cys Ala Ser Val Ala Phe
            35                  40                  45

Gly

<210> SEQ ID NO 51
<211> LENGTH: 145
<212> TYPE: PRT
<213> ORGANISM: Artificial Sequence
<220> FEATURE:
<223> OTHER INFORMATION: Synthetic Sequence

<400> SEQUENCE: 51

Met Ser Arg Ile Leu Glu Ser Glu Asn Glu Thr Glu Ser Asp Glu Ser
1               5                   10                  15

Ser Ile Ile Ser Thr Asn Asn Gly Thr Ala Met Glu Arg Ser Arg Asn
                20                  25                  30

Asn Gln Glu Leu Arg Ser Ser Pro His Thr Val Gln Asn Arg Leu Glu
            35                  40                  45

Leu Phe Ser Arg Arg Leu Ser Gln Leu Gly Leu Ala Ser Asp Ile Ser
        50                  55                  60

Val Asp Gln Gln Val Glu Asp Ser Ser Gly Thr Tyr Glu Gln Glu
65                  70                  75                  80

Glu Thr Ile Lys Thr Asn Ala Gln Thr Ser Lys Gln Lys Ser His Lys
                85                  90                  95

Asp Glu Lys Asn Ile Gln Lys Ile Gln Ile Lys Phe Gln Pro Ile Gly
            100                 105                 110

Ser Ile Gly Gln Leu Lys Pro Ser Val Cys Lys Ile Ser Met Ser Gln
        115                 120                 125

Ser Phe Ala Met Val Ile Leu Phe Leu Lys Arg Arg Leu Lys Met Asp
    130                 135                 140

His
145

<210> SEQ ID NO 52
<211> LENGTH: 41
<212> TYPE: PRT
<213> ORGANISM: Artificial Sequence
<220> FEATURE:
<223> OTHER INFORMATION: Synthetic Sequence

<400> SEQUENCE: 52

Val Tyr Cys Tyr Ile Asn Asn Ser Phe Ala Pro Ser Pro Gln Gln Asn
1               5                   10                  15

Ile Gly Glu Leu Trp Met Gln Phe Lys Thr Asn Asp Glu Leu Ile Val
                20                  25                  30

Ser Tyr Cys Ala Ser Val Ala Phe Gly
            35                  40

<210> SEQ ID NO 53
<211> LENGTH: 70
<212> TYPE: PRT
<213> ORGANISM: Artificial Sequence

```
<220> FEATURE:
<223> OTHER INFORMATION: Synthetic Sequence

<400> SEQUENCE: 53

Met Lys Ser Thr Phe Lys Ser Glu Tyr Pro Phe Glu Lys Arg Lys Ala
 1               5                  10                  15

Glu Ser Glu Arg Ile Ala Asp Arg Phe Lys Asn Arg Ile Pro Val Ile
            20                  25                  30

Cys Glu Lys Ala Glu Lys Ser Asp Ile Pro Glu Ile Asp Lys Arg Lys
        35                  40                  45

Tyr Leu Val Pro Ala Asp Leu Thr Val Gly Gln Phe Val Tyr Val Ile
    50                  55                  60

Arg Lys Arg Ile Met Leu
65                  70

<210> SEQ ID NO 54
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 54

Pro Pro Glu Lys Ala Ile Phe Ile Phe Val Asn Asp Thr Leu Pro Pro
 1               5                  10                  15

Thr Ala Ala Leu Met Ser Ala Ile Tyr Gln Glu His Lys Asp Lys Asp
            20                  25                  30

Gly Phe Leu Tyr Val Thr Tyr Ser Gly Glu Asn Thr Phe Gly
        35                  40                  45

<210> SEQ ID NO 55
<211> LENGTH: 76
<212> TYPE: PRT
<213> ORGANISM: Artificial Sequence
<220> FEATURE:
<223> OTHER INFORMATION: Synthetic Sequence

<400> SEQUENCE: 55

Met Lys Ser Thr Phe Lys Ser Glu Tyr Pro Phe Glu Lys Arg Lys Ala
 1               5                  10                  15

Glu Ser Glu Arg Ile Ala Asp Arg Phe Lys Asn Arg Ile Pro Val Ile
            20                  25                  30

Cys Glu Lys Ala Glu Lys Ser Asp Ile Pro Glu Ile Asp Lys Arg Lys
        35                  40                  45

Tyr Leu Val Pro Ala Asp Leu Thr Val Gly Gln Phe Val Tyr Val Ile
    50                  55                  60

Arg Lys Arg Ile Met Leu Pro Pro Glu Lys Ala Ile
65                  70                  75

<210> SEQ ID NO 56
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 56

Phe Ile Phe Val Asn Asp Thr Leu Pro Pro Thr Ala Ala Leu Met Ser
 1               5                  10                  15

Ala Ile Tyr Gln Glu His Lys Asp Lys Asp Gly Phe Leu Tyr Val Thr
            20                  25                  30
```

Tyr Ser Gly Glu Asn Thr Phe Gly
         35                  40

<210> SEQ ID NO 57
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 57

Met Ala Pro Asn Ala Ser Cys Leu Cys Val His Val Arg Ser Glu Glu
 1               5                  10                  15

Trp Asp Leu Met Thr Phe Asp Ala Asn Pro Tyr Asp Ser Val Lys Lys
                20                  25                  30

Ile Lys Glu His Val Arg Ser Lys Thr Lys Val Pro Val Gln Asp Gln
             35                  40                  45

Val Leu Leu Leu Gly Ser Lys Ile Leu Lys Pro Arg Arg Ser Leu Ser
 50                  55                  60

Ser Tyr Gly Ile Asp Lys Glu Lys Thr Ile His Leu Thr Leu Lys Val
 65                  70                  75                  80

Val Lys Pro Ser Asp Glu Glu Leu Pro Leu Phe Leu Val Glu Ser Gly
                 85                  90                  95

Asp Glu Ala Lys Arg His Leu Leu Gln Val Arg Arg Ser Ser Ser Val
                100                 105                 110

Ala Gln Val Lys Ala Met Ile
            115

<210> SEQ ID NO 58
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 58

Glu Thr Lys Thr Gly Ile Ile Pro Glu Thr Gln Ile Val Thr Cys Asn
 1               5                  10                  15

Gly Lys Arg Leu Glu Asp Gly Lys Met Met Ala Asp Tyr Gly Ile Arg
                20                  25                  30

Lys Gly Asn Leu Leu Phe Leu Ala Ser Tyr Cys Ile Gly Gly
             35                  40                  45

<210> SEQ ID NO 59
<211> LENGTH: 127
<212> TYPE: PRT
<213> ORGANISM: Artificial Sequence
<220> FEATURE:
<223> OTHER INFORMATION: Synthetic Sequence

<400> SEQUENCE: 59

Met Ala Pro Asn Ala Ser Cys Leu Cys Val His Val Arg Ser Glu Glu
 1               5                  10                  15

Trp Asp Leu Met Thr Phe Asp Ala Asn Pro Tyr Asp Ser Val Lys Lys
                20                  25                  30

Ile Lys Glu His Val Arg Ser Lys Thr Lys Val Pro Val Gln Asp Gln
             35                  40                  45

Val Leu Leu Leu Gly Ser Lys Ile Leu Lys Pro Arg Arg Ser Leu Ser
 50                  55                  60

-continued

```
Ser Tyr Gly Ile Asp Lys Glu Lys Thr Ile His Leu Thr Leu Lys Val
 65                  70                  75                  80

Val Lys Pro Ser Asp Glu Glu Leu Pro Leu Phe Leu Val Glu Ser Gly
                 85                  90                  95

Asp Glu Ala Lys Arg His Leu Leu Gln Val Arg Ser Ser Ser Val
            100                 105                 110

Ala Gln Val Lys Ala Met Ile Glu Thr Lys Thr Gly Ile Ile Pro
        115                 120                 125
```

<210> SEQ ID NO 60
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 60

```
Glu Thr Gln Ile Val Thr Cys Asn Gly Lys Arg Leu Glu Asp Gly Lys
  1               5                  10                  15

Met Met Ala Asp Tyr Gly Ile Arg Lys Gly Asn Leu Leu Phe Leu Ala
             20                  25                  30

Ser Tyr Cys Ile Gly Gly
         35
```

<210> SEQ ID NO 61
<211> LENGTH: 56
<212> TYPE: PRT
<213> ORGANISM: Artificial Sequence
<220> FEATURE:
<223> OTHER INFORMATION: Synthetic Sequence

<400> SEQUENCE: 61

```
Met Val Asn Val Lys Val Glu Phe Leu Gly Gly Leu Asp Ala Ile Phe
  1               5                  10                  15

Gly Lys Gln Arg Val His Lys Ile Lys Met Asp Lys Glu Asp Pro Val
             20                  25                  30

Thr Val Gly Asp Leu Ile Asp His Ile Val Ser Thr Met Ile Asn Asn
         35                  40                  45

Pro Asn Asp Val Ser Ile Phe Ile
     50                  55
```

<210> SEQ ID NO 62
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 62

```
Glu Asp Asp Ser Ile Arg Pro Gly Ile Ile Thr Leu Ile Asn Asp Thr
  1               5                  10                  15

Asp Trp Glu Leu Glu Gly Glu Lys Asp Tyr Ile Leu Glu Asp Gly Asp
             20                  25                  30

Ile Ile Ser Phe Thr Ser Thr Leu His Gly Gly
         35                  40
```

<210> SEQ ID NO 63
<211> LENGTH: 61
<212> TYPE: PRT
<213> ORGANISM: Artificial Sequence
<220> FEATURE:
<223> OTHER INFORMATION: Synthetic Sequence

```
<400> SEQUENCE: 63

Met Val Asn Val Lys Val Glu Phe Leu Gly Gly Leu Asp Ala Ile Phe
1               5                   10                  15

Gly Lys Gln Arg Val His Lys Ile Lys Met Asp Lys Glu Asp Pro Val
                20                  25                  30

Thr Val Gly Asp Leu Ile Asp His Ile Val Ser Thr Met Ile Asn Asn
            35                  40                  45

Pro Asn Asp Val Ser Ile Phe Ile Glu Asp Ser Ile
        50                  55                  60

<210> SEQ ID NO 64
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 64

Arg Pro Gly Ile Ile Thr Leu Ile Asn Asp Thr Asp Trp Glu Leu Glu
1               5                   10                  15

Gly Glu Lys Asp Tyr Ile Leu Glu Asp Gly Asp Ile Ile Ser Phe Thr
                20                  25                  30

Ser Thr Leu His Gly Gly
            35

<210> SEQ ID NO 65
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 65

Met Gln Leu Phe Val Arg Ala Gln Glu Leu His Thr Leu Glu Val Thr
1               5                   10                  15

Gly Gln Glu Thr Val Ala Gln Ile Lys Asp His Val Ala
                20                  25

<210> SEQ ID NO 66
<211> LENGTH: 45
<212> TYPE: PRT
<213> ORGANISM: Artificial Sequence
<220> FEATURE:
<223> OTHER INFORMATION: Synthetic Sequence

<400> SEQUENCE: 66

Ser Leu Glu Gly Ile Ala Pro Glu Asp Gln Val Val Leu Leu Ala Gly
1               5                   10                  15

Ser Pro Leu Glu Asp Glu Ala Thr Leu Gly Gln Cys Gly Val Glu Ala
                20                  25                  30

Leu Thr Thr Leu Glu Val Ala Gly Arg Met Leu Gly Gly
            35                  40                  45

<210> SEQ ID NO 67
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 67
```

Met Gln Leu Phe Val Arg Ala Gln Glu Leu His Thr Leu Glu Val Thr
1               5                   10                  15

Gly Gln Glu Thr Val Ala Gln Ile Lys Asp His Val Ala Ser Leu Glu
            20                  25                  30

Gly Ile Ala Pro Glu
        35

<210> SEQ ID NO 68
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 68

Asp Gln Val Val Leu Leu Ala Gly Ser Pro Leu Glu Asp Glu Ala Thr
1               5                   10                  15

Leu Gly Gln Cys Gly Val Glu Ala Leu Thr Thr Leu Glu Val Ala Gly
            20                  25                  30

Arg Met Leu Gly Gly
        35

<210> SEQ ID NO 69
<211> LENGTH: 50
<212> TYPE: DNA
<213> ORGANISM: Artificial Sequence
<220> FEATURE:
<223> OTHER INFORMATION: Primer

<400> SEQUENCE: 69
ccatgggtca tcaccatcat catcacgggt cggactcaga agtcaatcaa            50

<210> SEQ ID NO 70
<211> LENGTH: 36
<212> TYPE: DNA
<213> ORGANISM: Artificial Sequence
<220> FEATURE:
<223> OTHER INFORMATION: Primer

<400> SEQUENCE: 70
ggatccggtc tcaacctcca atctgttcgc ggtgag                           36

<210> SEQ ID NO 71
<211> LENGTH: 33
<212> TYPE: DNA
<213> ORGANISM: Artificial Sequence
<220> FEATURE:
<223> OTHER INFORMATION: Primer

<400> SEQUENCE: 71
ggtctcaagg tatggtgagc aagggcgagg agc                              33

<210> SEQ ID NO 72
<211> LENGTH: 31
<212> TYPE: DNA
<213> ORGANISM: Artificial Sequence
<220> FEATURE:
<223> OTHER INFORMATION: Primer

<400> SEQUENCE: 72
aagcttatta cttgtacagc tcgtccatgc c                                31

<210> SEQ ID NO 73
<211> LENGTH: 33

<212> TYPE: DNA
<213> ORGANISM: Artificial Sequence
<220> FEATURE:
<223> OTHER INFORMATION: Primer

<400> SEQUENCE: 73
ggtctcaagg tcccgtgagc aagggcgagg agc                              33

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74 tttttaagc ttgcggccgc actcg                                        25

<210> SEQ ID NO 75
<211> LENGTH: 32
<212> TYPE: DNA
<213> ORGANISM: Artificial Sequence
<220> FEATURE:
<223> OTHER INFORMATION: Primer

<400> SEQUENCE: 75 tttttaagc ttatttagcg aacgcttcca tc                                32

<210> SEQ ID NO 76
<211> LENGTH: 27
<212> TYPE: DNA
<213> ORGANISM: Artificial Sequence
<220> FEATURE:
<223> OTHER INFORMATION: Primer

<400> SEQUENCE: 76
gatataccat gggttgccat caccatc                                     27

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
gatggcaacc catggtatat ctcc                                        24

<210> SEQ ID NO 78
<211> LENGTH: 44
<212> TYPE: DNA
<213> ORGANISM: Artificial Sequence
<220> FEATURE:
<223> OTHER INFORMATION: Primer

<400> SEQUENCE: 78
ttttttggtc tcgtcatcat cacaaaagac agggtaagga aatg                  44

<210> SEQ ID NO 79
<211> LENGTH: 33
<212> TYPE: DNA
<213> ORGANISM: Artificial Sequence
<220> FEATURE:
<223> OTHER INFORMATION: Primer

<400> SEQUENCE: 79

-continued tttttggtc tcgatgatgg tgatgaccca tgg					33

<210> SEQ ID NO 80
<211> LENGTH: 44
<212> TYPE: DNA
<213> ORGANISM: Artificial Sequence
<220> FEATURE:
<223> OTHER INFORMATION: Primer

<400> SEQUENCE: 80 tttttggtc tcgtcatcat cacgaaagac agggtaagga aatg					44

<210> SEQ ID NO 81
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 81
catggaaacc gctgctgcta aattcgaacg ccagca					36

<210> SEQ ID NO 82
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 82
catgtgctgg cgttcgaatt tagcagcagc ggtttc					36

<210> SEQ ID NO 83
<211> LENGTH: 38
<212> TYPE: DNA
<213> ORGANISM: Artificial Sequence
<220> FEATURE:
<223> OTHER INFORMATION: Primer

<400> SEQUENCE: 83 tttttcgtc tcccatgtcc cctatactag gttaattg					38

<210> SEQ ID NO 84
<211> LENGTH: 31
<212> TYPE: DNA
<213> ORGANISM: Artificial Sequence
<220> FEATURE:
<223> OTHER INFORMATION: Primer

<400> SEQUENCE: 84 ttttttcca tggcaccttg aaaataaaga t					31

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85 ttttttcca tgggacttgt tcctgaatta aatgaa					36

<210> SEQ ID NO 86
<211> LENGTH: 36
<212> TYPE: DNA
<213> ORGANISM: Artificial Sequence

```
<220> FEATURE:
<223> OTHER INFORMATION: Primer

<400> SEQUENCE: 86 tttttctcg agttttaaag cgtcggttaa aatcaa                              36

<210> SEQ ID NO 87
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 87

Lys Ile Lys Lys Thr Thr Pro Leu
 1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 88

Glu Asp Leu Asp Met Glu
 1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 89

Asp Asn Asp Ile Ile Glu Ala His
 1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 90

Ile Asn Leu Lys Val Ser Asp
 1               5

<210> SEQ ID NO 91
<211> LENGTH: 54
<212> TYPE: PRT
<213> ORGANISM: Artificial Sequence
<220> FEATURE:
<223> OTHER INFORMATION: Synthetic Sequence

<400> SEQUENCE: 91

Met Ser Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
            35                  40                  45

Met Glu Ala Phe Ala Lys
            50
```

<210> SEQ ID NO 92
<211> LENGTH: 162
<212> TYPE: DNA
<213> ORGANISM: Artificial Sequence
<220> FEATURE:
<223> OTHER INFORMATION: Synthetic Sequence

<400> SEQUENCE: 92

```
atgtcggact cagaagtcaa tcaagaagct aagccagagg tcaagccaga agtcaagcct      60
gagactcaca tcaatttaaa ggtgtccgat ggatcttcag agatcttctt caagatcaaa    120
aagaccactc ctttaagaag gctgatggaa gcgttcgcta aa                        162
```

<210> SEQ ID NO 93
<211> LENGTH: 80
<212> TYPE: PRT
<213> ORGANISM: Artificial Sequence
<220> FEATURE:
<223> OTHER INFORMATION: Synthetic Sequence

<400> SEQUENCE: 93

```
Met Gly His His His His His His Gly Ser Asp Ser Glu Val Asn Gln
 1               5                  10                  15
Glu Ala Lys Pro Glu Val Lys Pro Glu Val Lys Pro Glu Thr His Ile
            20                  25                  30
Asn Leu Lys Val Ser Asp Gly Ser Ser Glu Ile Phe Phe Lys Ile Lys
        35                  40                  45
Lys Thr Thr Pro Leu Arg Arg Leu Met Glu Ala Phe Ala Lys Arg Gln
    50                  55                  60
Gly Lys Glu Lys Leu Ala Ala Ala Leu Glu His His His His His His
65                  70                  75                  80
```

<210> SEQ ID NO 94
<211> LENGTH: 243
<212> TYPE: DNA
<213> ORGANISM: Artificial Sequence
<220> FEATURE:
<223> OTHER INFORMATION: Synthetic Sequence

<400> SEQUENCE: 94

```
atgggtcatc accatcatca tcacgggtcg gactcagaag tcaatcaaga agctaagcca      60
gaggtcaagc cagaagtcaa gcctgagact cacatcaatt taaaggtgtc cgatggatct    120
tcagagatct tcttcaagat caaaaagacc actcctttaa gaaggctgat ggaagcgttc    180
gctaaaagac agggtaagga aaagcttgcg ccgcactcg agcaccacca ccaccaccac    240
tga                                                                  243
```

<210> SEQ ID NO 95
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 95

```
Met Gln Ile Phe Val Lys Thr Leu Thr Gly Lys Thr Ile Thr Leu Glu
 1               5                  10                  15
Val Glu Pro Ser Asp Thr Ile Glu Asn Val Lys Ala Lys Ile Gln
            20                  25                  30
```

<210> SEQ ID NO 96
<211> LENGTH: 45
<212> TYPE: PRT
<213> ORGANISM: Artificial Sequence
<220> FEATURE:
<223> OTHER INFORMATION: Synthetic Sequence

<400> SEQUENCE: 96

Asp Lys Glu Gly Ile Pro Pro Asp Gln Gln Arg Leu Ile Phe Ala Gly
 1               5                  10                  15

Lys Gln Leu Glu Asp Gly Arg Thr Leu Ser Asp Tyr Asn Ile Gln Lys
            20                  25                  30

Glu Ser Thr Leu His Leu Val Leu Arg Leu Arg Gly Gly
        35                  40                  45

<210> SEQ ID NO 97
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 97

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro
        35

<210> SEQ ID NO 98
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 98

Asp Gln Gln Arg Leu Ile Phe Ala Gly Lys Gln Leu Glu Asp Gly Arg
 1               5                  10                  15

Thr Leu Ser Asp Tyr Asn Ile Gln Lys Glu Ser Thr Leu His Leu Val
            20                  25                  30

Leu Arg Leu Arg Gly Gly
        35

<210> SEQ ID NO 99
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)...(6)
<223> OTHER INFORMATION: n = A, C, T, or G

<400> SEQUENCE: 99
nnnnnngaga gg                                                         12

<210> SEQ ID NO 100
<211> LENGTH: 12
<212> TYPE: DNA
<213> ORGANISM: Artificial Sequence
<220> FEATURE:

```
<223> OTHER INFORMATION: Synthetic Sequence
<220> FEATURE:
<221> NAME/KEY: misc_feature
<222> LOCATION: (1)...(6)
<223> OTHER INFORMATION: n = A, C, T, or G

<400> SEQUENCE: 100
nnnnnnctct gc                                                              12

<210> SEQ ID NO 101
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)...(12)
<223> OTHER INFORMATION: n = A, C, T, or G

<400> SEQUENCE: 101
ggtctcnnnn nn                                                              12

<210> SEQ ID NO 102
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)...(12)
<223> OTHER INFORMATION: n = A, C, G, or T

<400> SEQUENCE: 102
ccagagnnnn nn                                                              12

<210> SEQ ID NO 103
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 103
aagcttgaga cc                                                              12

<210> SEQ ID NO 104
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 104
ttcgaactct gg                                                              12

<210> SEQ ID NO 105
<211> LENGTH: 76
<212> TYPE: PRT
<213> ORGANISM: Artificial Sequence
<220> FEATURE:
<223> OTHER INFORMATION: Synthetic Sequence

<400> SEQUENCE: 105

Met Ile Val Phe Val Arg Phe Asn Ser Ser His Gly Phe Pro Val Glu
1               5                   10                  15
```

```
Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys
65                  70                  75

<210> SEQ ID NO 106
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 106

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg

<210> SEQ ID NO 107
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 107

Gln Gly Val Pro Ala Asp Gln Leu Arg Val Ile Phe Ala Gly Lys Glu
1               5                   10                  15

Leu Arg Asn Asp Trp Thr Val Gln Asn Cys Asp Leu Asp Gln Gln Ser
            20                  25                  30

Ile Val His Ile Val Gln Arg Pro Trp Arg Lys
        35                  40

<210> SEQ ID NO 108
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 108

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln
        35                  40

<210> SEQ ID NO 109
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 109

Leu Arg Val Ile Phe Ala Gly Lys Glu Leu Arg Asn Asp Trp Thr Val
```

```
                1               5                  10                  15
Gln Asn Cys Asp Leu Asp Gln Gln Ser Ile Val His Ile Val Gln Arg
            20                  25                  30

Pro Trp Arg Lys
        35

<210> SEQ ID NO 110
<211> LENGTH: 88
<212> TYPE: PRT
<213> ORGANISM: Artificial Sequence
<220> FEATURE:
<223> OTHER INFORMATION: Synthetic Sequence

<400> SEQUENCE: 110

Met Thr Leu Arg Trp Lys Arg Met Ile Asn Val Leu Phe Phe Ala Gln
1               5                   10                  15

Val Arg Glu Leu Val Gly Thr Asp Ala Thr Glu Val Ala Ala Asp Phe
            20                  25                  30

Pro Thr Val Glu Ala Leu Arg Gln His Leu Ala Ala Gln Ser Asp Arg
        35                  40                  45

Trp Ala Leu Ala Leu Glu Asp Gly Lys Leu Leu Ala Ala Val Asn Gln
    50                  55                  60

Thr Leu Val Ser Phe Asp His Ser Leu Thr Asp Gly Asp Glu Val Ala
65                  70                  75                  80

Phe Phe Pro Pro Val Thr Gly Gly
                85

<210> SEQ ID NO 111
<211> LENGTH: 53
<212> TYPE: PRT
<213> ORGANISM: Artificial Sequence
<220> FEATURE:
<223> OTHER INFORMATION: Synthetic Sequence

<400> SEQUENCE: 111

Met Thr Leu Arg Trp Lys Arg Met Ile Asn Val Leu Phe Phe Ala Gln
1               5                   10                  15

Val Arg Glu Leu Val Gly Thr Asp Ala Thr Glu Val Ala Ala Asp Phe
            20                  25                  30

Pro Thr Val Glu Ala Leu Arg Gln His Leu Ala Ala Gln Ser Asp Arg
        35                  40                  45

Trp Ala Leu Ala Leu
    50

<210> SEQ ID NO 112
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 112

Glu Asp Gly Lys Leu Leu Ala Ala Val Asn Gln Thr Leu Val Ser Phe
1               5                   10                  15

Asp His Ser Leu Thr Asp Gly Asp Glu Val Ala Phe Phe Pro Pro Val
            20                  25                  30

Thr Gly Gly
        35

<210> SEQ ID NO 113
```

```
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 113

Met Thr Leu Arg Trp Lys Arg Met Ile Asn Val Leu Phe Phe Ala Gln
1               5                   10                  15

Val Arg Glu Leu Val Gly Thr Asp Ala Thr Glu Val Ala Ala Asp Phe
            20                  25                  30

Pro Thr Val Glu Ala Leu Arg Gln His Leu Ala Ala Gln Ser Asp Arg
        35                  40                  45

Trp Ala Leu Ala Leu Glu Asp Gly Lys Leu
    50                  55

<210> SEQ ID NO 114
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 114

Leu Ala Ala Val Asn Gln Thr Leu Val Ser Phe Asp His Ser Leu Thr
1               5                   10                  15

Asp Gly Asp Glu Val Ala Phe Phe Pro Pro Val Thr Gly Gly
            20                  25                  30

<210> SEQ ID NO 115
<211> LENGTH: 85
<212> TYPE: PRT
<213> ORGANISM: Artificial Sequence
<220> FEATURE:
<223> OTHER INFORMATION: Synthetic Sequence

<400> SEQUENCE: 115

Gly Ala Met Gly Ser Ser Thr Ser Gly Leu Lys Thr Thr Lys Ile Lys
1               5                   10                  15

Phe Tyr Tyr Lys Asp Asp Ile Phe Ala Leu Met Leu Lys Gly Asp Thr
            20                  25                  30

Thr Tyr Lys Glu Leu Arg Ser Lys Ile Ala Pro Arg Ile Asp Thr Asp
        35                  40                  45

Asn Phe Lys Leu Gln Thr Lys Leu Phe Asp Gly Ser Gly Glu Glu Ile
    50                  55                  60

Lys Thr Asp Ser Gln Val Ser Asn Ile Ile Gln Ala Lys Leu Lys Ile
65                  70                  75                  80

Ser Val His Asp Ile
            85

<210> SEQ ID NO 116
<211> LENGTH: 41
<212> TYPE: PRT
<213> ORGANISM: Artificial Sequence
<220> FEATURE:
<223> OTHER INFORMATION: Synthetic Sequence

<400> SEQUENCE: 116

Gly Ala Met Gly Ser Ser Thr Ser Gly Leu Lys Thr Thr Lys Ile Lys
1               5                   10                  15

Phe Tyr Tyr Lys Asp Asp Ile Phe Ala Leu Met Leu Lys Gly Asp Thr
            20                  25                  30
```

```
Thr Tyr Lys Glu Leu Arg Ser Lys Ile
        35                  40
```

<210> SEQ ID NO 117
<211> LENGTH: 44
<212> TYPE: PRT
<213> ORGANISM: Artificial Sequence
<220> FEATURE:
<223> OTHER INFORMATION: Synthetic Sequence

<400> SEQUENCE: 117

```
Ala Pro Arg Ile Asp Thr Asp Asn Phe Lys Leu Gln Thr Lys Leu Phe
 1               5                  10                  15

Asp Gly Ser Gly Glu Glu Ile Lys Thr Asp Ser Gln Val Ser Asn Ile
            20                  25                  30

Ile Gln Ala Lys Leu Lys Ile Ser Val His Asp Ile
        35                  40
```

<210> SEQ ID NO 118
<211> LENGTH: 48
<212> TYPE: PRT
<213> ORGANISM: Artificial Sequence
<220> FEATURE:
<223> OTHER INFORMATION: Synthetic Sequence

<400> SEQUENCE: 118

```
Gly Ala Met Gly Ser Ser Thr Ser Gly Leu Lys Thr Thr Lys Ile Lys
 1               5                  10                  15

Phe Tyr Tyr Lys Asp Asp Ile Phe Ala Leu Met Leu Lys Gly Asp Thr
            20                  25                  30

Thr Tyr Lys Glu Leu Arg Ser Lys Ile Ala Pro Arg Ile Asp Thr Asp
        35                  40                  45
```

<210> SEQ ID NO 119
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 119

```
Asn Phe Lys Leu Gln Thr Lys Leu Phe Asp Gly Ser Gly Glu Glu Ile
 1               5                  10                  15

Lys Thr Asp Ser Gln Val Ser Asn Ile Ile Gln Ala Lys Leu Lys Ile
            20                  25                  30

Ser Val His Asp Ile
        35
```

<210> SEQ ID NO 120
<211> LENGTH: 80
<212> TYPE: PRT
<213> ORGANISM: Artificial Sequence
<220> FEATURE:
<223> OTHER INFORMATION: Synthetic Sequence

<400> SEQUENCE: 120

```
Met Leu Gln Lys Pro Lys Ser Val Lys Leu Arg Ala Leu Arg Ser Pro
 1               5                  10                  15

Arg Lys Phe Gly Val Ala Gly Arg Ser Cys Gln Glu Val Leu Arg Lys
            20                  25                  30

Gly Cys Leu Arg Phe Gln Leu Pro Glu Arg Gly Ser Arg Leu Cys Leu
        35                  40                  45
```

Tyr Glu Asp Gly Thr Glu Leu Thr Glu Asp Tyr Phe Pro Ser Val Pro
            50                  55                  60

Asp Asn Ala Glu Leu Val Leu Leu Thr Leu Gly Gln Ala Trp Gln Gly
 65                  70                  75                  80

<210> SEQ ID NO 121
<211> LENGTH: 36
<212> TYPE: PRT
<213> ORGANISM: Artificial Sequence
<220> FEATURE:
<223> OTHER INFORMATION: Synthetic Sequence

<400> SEQUENCE: 121

Met Leu Gln Lys Pro Lys Ser Val Lys Leu Arg Ala Leu Arg Ser Pro
  1               5                  10                  15

Arg Lys Phe Gly Val Ala Gly Arg Ser Cys Gln Glu Val Leu Arg Lys
                 20                  25                  30

Gly Cys Leu Arg
            35

<210> SEQ ID NO 122
<211> LENGTH: 44
<212> TYPE: PRT
<213> ORGANISM: Artificial Sequence
<220> FEATURE:
<223> OTHER INFORMATION: Synthetic Sequence

<400> SEQUENCE: 122

Phe Gln Leu Pro Glu Arg Gly Ser Arg Leu Cys Leu Tyr Glu Asp Gly
  1               5                  10                  15

Thr Glu Leu Thr Glu Asp Tyr Phe Pro Ser Val Pro Asp Asn Ala Glu
                 20                  25                  30

Leu Val Leu Leu Thr Leu Gly Gln Ala Trp Gln Gly
            35                  40

<210> SEQ ID NO 123
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 123

Met Leu Gln Lys Pro Lys Ser Val Lys Leu Arg Ala Leu Arg Ser Pro
  1               5                  10                  15

Arg Lys Phe Gly Val Ala Gly Arg Ser Cys Gln Glu Val Leu Arg Lys
                 20                  25                  30

Gly Cys Leu Arg Phe Gln Leu Pro Glu Arg Gly
            35                  40

<210> SEQ ID NO 124
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 124

Ser Arg Leu Cys Leu Tyr Glu Asp Gly Thr Glu Leu Thr Glu Asp Tyr
  1               5                  10                  15

Phe Pro Ser Val Pro Asp Asn Ala Glu Leu Val Leu Leu Thr Leu Gly
                 20                  25                  30

Gln Ala Trp Gln Gly
        35

<210> SEQ ID NO 125
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 125

Lys Glu Ile Lys Val Pro Val Asn Val Trp Asp Lys Ser Lys Gln Gln
1               5                   10                  15

Pro Pro Met Phe Ile Thr Val Asn Lys Pro Lys Val Thr Ala Gln Glu
            20                  25                  30

Val Asp Ile Lys Val Arg Lys Leu Leu Ile Lys Lys Tyr Asp Ile Tyr
        35                  40                  45

Asn Asn Arg Glu Gln Lys Tyr Ser Lys Gly Thr Val Thr Leu Asp Leu
    50                  55                  60

Asn Ser Gly Lys Asp Ile Val Phe Asp Leu Tyr Tyr Phe Gly Asn Gly
65                  70                  75                  80

Asp Phe Asn Ser Met Leu Lys Ile Tyr Ser Asn Asn Glu Arg Ile Asp
                85                  90                  95

Ser Thr Gln Phe His Val Asp Val Ser Ile Ser
            100                 105

<210> SEQ ID NO 126
<211> LENGTH: 44
<212> TYPE: PRT
<213> ORGANISM: Artificial Sequence
<220> FEATURE:
<223> OTHER INFORMATION: Synthetic Sequence

<400> SEQUENCE: 126

Lys Glu Ile Lys Val Pro Val Asn Val Trp Asp Lys Ser Lys Gln Gln
1               5                   10                  15

Pro Pro Met Phe Ile Thr Val Asn Lys Pro Lys Val Thr Ala Gln Glu
            20                  25                  30

Val Asp Ile Lys Val Arg Lys Leu Leu Ile Lys Lys
        35                  40

<210> SEQ ID NO 127
<211> LENGTH: 63
<212> TYPE: PRT
<213> ORGANISM: Artificial Sequence
<220> FEATURE:
<223> OTHER INFORMATION: Synthetic Sequence

<400> SEQUENCE: 127

Tyr Asp Ile Tyr Asn Asn Arg Glu Gln Lys Tyr Ser Lys Gly Thr Val
1               5                   10                  15

Thr Leu Asp Leu Asn Ser Gly Lys Asp Ile Val Phe Asp Leu Tyr Tyr
            20                  25                  30

Phe Gly Asn Gly Asp Phe Asn Ser Met Leu Lys Ile Tyr Ser Asn Asn
        35                  40                  45

Glu Arg Ile Asp Ser Thr Gln Phe His Val Asp Val Ser Ile Ser
    50                  55                  60

<210> SEQ ID NO 128
<211> LENGTH: 56

```
<212> TYPE: PRT
<213> ORGANISM: Artificial Sequence
<220> FEATURE:
<223> OTHER INFORMATION: Synthetic Sequence

<400> SEQUENCE: 128

Lys Glu Ile Lys Val Pro Val Asn Val Trp Asp Lys Ser Lys Gln Gln
1               5                   10                  15

Pro Pro Met Phe Ile Thr Val Asn Lys Pro Lys Val Thr Ala Gln Glu
            20                  25                  30

Val Asp Ile Lys Val Arg Lys Leu Leu Ile Lys Lys Tyr Asp Ile Tyr
        35                  40                  45

Asn Asn Arg Glu Gln Lys Tyr Ser
    50                  55

<210> SEQ ID NO 129
<211> LENGTH: 51
<212> TYPE: PRT
<213> ORGANISM: Artificial Sequence
<220> FEATURE:
<223> OTHER INFORMATION: Synthetic Sequence

<400> SEQUENCE: 129

Lys Gly Thr Val Thr Leu Asp Leu Asn Ser Gly Lys Asp Ile Val Phe
1               5                   10                  15

Asp Leu Tyr Tyr Phe Gly Asn Gly Asp Phe Asn Ser Met Leu Lys Ile
            20                  25                  30

Tyr Ser Asn Asn Glu Arg Ile Asp Ser Thr Gln Phe His Val Asp Val
        35                  40                  45

Ser Ile Ser
    50

<210> SEQ ID NO 130
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 130

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly Val Trp
        35                  40                  45

Thr Tyr Asp Asp Ala Thr Lys Thr Phe Thr Val Thr Glu
    50                  55                  60

<210> SEQ ID NO 131
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 131

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30
```

```
Lys Ala Phe Lys Gln Tyr Ala Asn Asp Asn Gly
        35                  40
```

<210> SEQ ID NO 132
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 132

```
Val Asp Gly Val Trp Thr Tyr Asp Asp Ala Thr Lys Thr Phe Thr Val
 1               5                  10                  15

Thr Glu
```

<210> SEQ ID NO 133
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 133

```
Met Thr Pro Ala Val Thr Thr Tyr Lys Leu Val Ile Asn Gly Lys Thr
 1               5                  10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly
        35                  40                  45
```

<210> SEQ ID NO 134
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 134

```
Val Trp Thr Tyr Asp Asp Ala Thr Lys Thr Phe Thr Val Thr Glu
 1               5                  10                  15
```

<210> SEQ ID NO 135
<211> LENGTH: 62
<212> TYPE: PRT
<213> ORGANISM: Artificial Sequence
<220> FEATURE:
<223> OTHER INFORMATION: Synthetic Sequence

<400> SEQUENCE: 135

```
Met Ser Lys Asp Phe Ile Ile Asn Glu Gln Ile Arg Ala Arg Glu Val
 1               5                  10                  15

Arg Leu Ile Asp Gln Asn Gly Asp Gln Leu Gly Ile Lys Ser Lys Gln
            20                  25                  30

Glu Ala Leu Glu Ile Ala Ala Arg Arg Asn Leu Asp Leu Val Leu Val
        35                  40                  45

Ala Pro Asn Ala Lys Pro Pro Val Cys Arg Ile Met Asp Tyr
    50                  55                  60
```

<210> SEQ ID NO 136
<211> LENGTH: 39
<212> TYPE: PRT
<213> ORGANISM: Artificial Sequence
<220> FEATURE:
<223> OTHER INFORMATION: Synthetic Sequence

```
<400> SEQUENCE: 136

Met Ser Lys Asp Phe Ile Ile Asn Glu Gln Ile Arg Ala Arg Glu Val
1               5                   10                  15

Arg Leu Ile Asp Gln Asn Gly Asp Gln Leu Gly Ile Lys Ser Lys Gln
            20                  25                  30

Glu Ala Leu Glu Ile Ala Ala
        35

<210> SEQ ID NO 137
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 137

Arg Arg Asn Leu Asp Leu Val Leu Val Ala Pro Asn Ala Lys Pro Pro
1               5                   10                  15

Val Cys Arg Ile Met Asp Tyr
            20

<210> SEQ ID NO 138
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 138

Met Ser Lys Asp Phe Ile Ile Asn Glu Gln Ile Arg Ala Arg Glu Val
1               5                   10                  15

Arg Leu Ile Asp Gln Asn Gly Asp Gln Leu Gly Ile Lys Ser Lys Gln
            20                  25                  30

Glu Ala Leu Glu Ile Ala Ala Arg Arg Asn Leu
        35                  40

<210> SEQ ID NO 139
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 139

Asp Leu Val Leu Val Ala Pro Asn Ala Lys Pro Pro Val Cys Arg Ile
1               5                   10                  15

Met Asp Tyr

<210> SEQ ID NO 140
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 140

Asp Tyr Lys Asp Asp Asp Asp Lys
1               5
```

METHODS AND COMPOSITIONS FOR ENHANCED PROTEIN EXPRESSION AND PURIFICATION

This application is a 371 application of PCT/US04/20778, filed Jun. 28, 2004, which in turn claims priority to U.S. Provisional Application 60/482,817, filed Jun. 26, 2003. The entire disclosure of each of the above identified applications is incorporated by reference herein.

FIELD OF THE INVENTION

The present invention relates to the field of recombinant gene expression and purification of expressed proteins. More specifically, the invention provides materials and methods which facilitate purification of heterologous proteins from a variety of different host species.

BACKGROUND OF THE INVENTION

Several publications and patent documents are cited throughout the specification in order to describe the state of the art to which this invention pertains. Full citations of these references can be found throughout the specification. Each of these citations is incorporated herein as though set forth in full.

Functional genomic studies have been hampered by the inability to uniformly express and purify biologically active proteins in heterologous expression systems (1). Despite the use of identical transcriptional and translational signals in a given expression vector, expressed protein levels have been observed to vary dramatically (2). For this reason, several strategies have been developed to express heterologous proteins in bacteria, yeast, mammalian and insect cells as gene-fusions (3-6).

The expression of heterologous genes in bacteria is by far the simplest and most inexpensive means available for research or commercial purposes. However, some heterologous gene products fail to attain their correct three-dimensional conformation in E. coli while others become sequestered in large insoluble aggregates or "inclusion bodies" when overproduced (7,8). Major denaturant-induced solubilization methods followed by removal of the denaturant under conditions that favor refolding are often required to produce a reasonable yield of the recombinant protein. Selection of ORFs for structural genomics projects has also shown that only about 20% of the genes expressed in E. coli render proteins that are soluble or correctly folded (9). These numbers are startlingly disappointing especially given that most scientists rely on E. coli for initial attempts to express gene products. Several gene fusion systems such as NUS A, maltose binding protein (MUP), glutathione S transferase (GST), and thioredoxin (TRX) have been developed (7). All of these systems have certain drawbacks, ranging from inefficient expression to inconsistent cleavage from desired structure.

Ubiquitin (Ub) and ubiquitin like proteins (Ubls) have been described in the literature (10-12). The SUMO system has also been characterized (13). SUMO (small-ubiquitin related modifier) is also known as Sentrin, SMT3, PIC1, GMP1 and UBL1. SUMO and the SUMO pathway are present throughout the eukaryotic kingdom and the proteins are highly conserved from yeast to humans (14). Yeast has only a single SUMO gene, which has also been termed SMT3. The yeast Smt3 gene is essential for viability (13). In contrast to yeast, three members of SUMO have been described in vertebrates: SUMO-1 and close homologues SUMO-2 and SUMO-3. Human SUMO-1, a 101 amino-acid polypeptide, shares 50% sequence identity with human SUMO-2/SUMO-3 (15). Yeast SUMO (SMT3) shares 47% sequence identity with mammalian SUMO-1. Although overall sequence homology between ubiquitin and SUMO is only 18%, structure determination by nuclear magnetic resonance (NMR) reveals that the two proteins possess a common three dimensional structure characterized by a tightly packed globular fold with β-sheets wrapped around one α-helix (16-17). Examination of the chaperoning properties of SUMO reveals that attachment of a tightly packed globular structure to the N-terminus of a protein can act as a nucleus for folding and protect the labile protein. All SUMO genes encode precursor proteins with a short C-terminal sequence that extends from the conserved C-terminal Gly-Gly motif (13). The extension sequence, 2-12 amino acids in length, is different in all cases. Cells contain potent SUMO proteases (known also as hydrolases) that remove the C-terminal extensions (18). The C-terminus of SUMO is conjugated to ε-amino groups of lysine residues of target proteins. The similarity sumoylation pathway enzymes to ubiquitin pathway enzymes is remarkable, given the different effects of these two protein modification pathways (19). Sumoylation of cellular proteins has been proposed to regulate nuclear transport, signal transduction, stress response, and cell cycle progression (20). It is very likely that SUMO chaperones translocation of proteins among various cell compartments, however, the precise mechanistic details of this function of SUMO are not known.

Other fusions promote solubility of partner proteins presumably due to their large size (e.g., NusA)(21). Fusion of proteins with glutathione S-transferase (GST)(22) or maltose binding protein (MBP)(23) has been proposed to enhance expression and yield of fusion partners. However, enhanced expression is not always observed when GST is used as GST forms dimers and can retard protein solubility. Another problem with GST or other fusion systems is that the desired protein may have to be removed from the fusion. To circumvent this problem, protease sites, such as Factor Xa, thrombin, enterokinase or Tev protease sites are often engineered downstream of the fusion partner. Often in these cases, however, incomplete cleavage and inappropriate cleavage within the fusion protein is often observed (7). The present invention circumvents these problems.

SUMMARY OF THE INVENTION

In accordance with the present invention, compositions and methods for enhancing expression levels of a protein of interest are provided. An exemplary method comprises i) generating a construct encoding a fusion protein by operably linking a nucleic acid sequence encoding a carboxy-terminal domain of a Ubl molecule selected from the group consisting of SUMO, Ub, RUB, HUB, APG8, APG12, URM1, Ubi-L, FAT10 and ISG15 to a nucleic acid sequence encoding the protein of interest, and ii) introducing the nucleic acid encoding the fusion protein into a host cell. To purify the protein of interest, the method may further comprises: iii) lysing the cells expressing the fusion protein, iv) contacting the cellular lysate with an amino-terminal domain of the same said Ubl immobilized on a solid phase, optionally by a purification tag attached to the amino-terminal domain, thereby reconstituting the Ubl, and v) contacting the reconstituted, and now cleavable, Ubl with the appropriate Ubl protease to release the protein of interest from the fusion protein. According to another aspect of the invention, the reconstituted Ubl from step iv) is eluted from the column and is then contacted with the appropriate protease in solution to release the protein of interest from the fusion protein. According to another aspect of the invention, the reconstituted Ubl is formed in solution and then purified over the solid support. According to yet another aspect of the instant invention, Ubl protease inhibitors are included while the Ubl is being reconstituted and then removed prior to the addition of the Ubl protease.

In accordance with another aspect of the invention, compositions and methods for purifying a protein of interest are provided. An exemplary method comprises i) generating a construct encoding a fusion protein by operably linking a nucleic acid sequence encoding a carboxy-terminal domain of a Ubl molecule selected from the group consisting of SUMO, Ub, RUB, HUB, APG8, APG12, URM1, Ubi-L, FAT10 and ISG15 to a nucleic acid sequence encoding the protein of interest and to a nucleic acid encoding at least one purification tag, whereby the purification tag is added to the amino terminus of the carboxy-terminal domain which is attached to the amino-terminus of the protein of interest, ii) introducing the nucleic acid encoding the fusion protein into a host cell, iii) lysing the cells expressing the fusion protein, iv) optionally purifying the fusion protein by contacting the fusion protein with a solid support capable of binding at least one purification tag; v) contacting fusion protein containing solution with an amino-terminal domain of the same said Ubl immobilized on a solid phase, optionally by a purification tag attached to the amino-terminal domain, thereby reconstituting the Ubl, and vi) contacting the reconstituted, and now cleavable, Ubl with the appropriate Ubl protease to release the protein of interest from the fusion protein. According to another aspect of the invention, the reconstituted Ubl from step iv) is eluted from the column and is then contacted with the appropriate protease in solution to release the protein of interest from the fusion protein. According to another aspect of the invention, the reconstituted Ubl is formed in solution and then purified over the solid support. According to yet another aspect of the instant invention, Ubl protease inhibitors are included while the Ubl is being reconstituted and then removed prior to the addition of the Ubl protease. In yet another aspect of the invention, the Ubl may also comprise a purification tag to ensure its removal during the purification scheme.

In yet another embodiment of the invention, the molecule used to generate a fusion construct with the protein of interest is the carboxy-terminal part of SUMO (CTHS) encoded by a nucleic acid comprising the sequence of SEQ ID NO: 10. The molecule used for purification and cleavage of the fusion protein is the amino-terminal part of SUMO (NTHS) encoded by the nucleic acid comprising the sequence of SEQ ID NO: 6. The specific hydrolase (i.e. protease) used to cleave the reconstituted Ubl thereby releasing the protein of interest is a SUMO hydrolase encoded by a nucleic acid comprising the sequence of SEQ ID NO: 30.

In yet another embodiment of the invention, an exemplary method for generating a protein of interest having an altered amino terminus is provided. Such a method comprises altering the amino terminus of the protein of interest and performing the purification methods exemplified herein. In accordance with another aspect of the invention, the protein of interest with an altered amino-terminus may be produced in vivo by a method comprising: i) generating a construct encoding a fusion protein by operably linking a nucleic acid sequence encoding a carboxy-terminal domain of a Ubl molecule selected from the group consisting of SUMO, Ub, RUB, HUB, APG8, APG12, URM1, Ubi-L, FAT10 and ISG15 to a nucleic acid sequence encoding the protein of interest with an altered amino-terminus, ii) introducing the nucleic acid encoding the fusion protein into a host cell, iii) introducing a nucleic acid encoding an amino-terminal domain of the Ubl molecule into the host cell at a desired time, and iv) optionally introducing a nucleic acid encoding a Ubl specific protease into the host cell if cleavage of the reconstituted Ubl is insufficient.

In yet another embodiment of the invention, methods are provided for increasing the affinity between a carboxy-terminal domain of a ubiquitin-like (Ubl) molecule and a amino-terminal domain of a ubiquitin-like (Ubl) molecule. An exemplary method comprises operably linking a moiety to the carboxy-terminal domain and amino-terminal domain, wherein the attached moiety comprises an anti-parallel β-sheet structure, an anti-parallel a-helix structure, or negatively and positively charged amino acids. In accordance with another aspect of the invention, a method of increasing the affinity between a carboxy-terminal domain of a ubiquitin-like (Ubl) molecule and an amino-terminal domain of a ubiquitin-like (Ubl) molecule is provided comprising inserting mutations into the carboxy-terminal domain and amino-terminal domain wherein the mutations increase the hydrophobicity between the two domains or the mutations introduce charged amino acids.

In yet another embodiment of the invention, kits are provided for performing the methods described herein. Such kits comprise a recombinant vector containing a nucleic acid sequence encoding a carboxy-terminal portion of a Ubl molecule selected from the group of SUMO, Ub, RUB, HUB, APG8, APG12, URM1, Ubi-L, FAT10 and ISG15 operably linked to a promoter suitable for expression in the desired host cell and a multiple cloning site suitable for cloning a nucleic acid encoding the protein of interest. The recombinant vector may also contain a nucleic acid sequence encoding for at least one purification tag. The kits may further comprise a preparation of a protease capable of cleaving a reconstituted Ubl molecule from the fusion protein optionally comprising a purification tag, a preparation of an amino-terminal portion of a Ubl molecule optionally comprising at least one purification tag, a recombinant vector containing a nucleic acid sequence encoding an amino-terminal portion of a Ubl molecule optionally comprising at least one purification tag, at least one solid phase capable of binding at least one purification tag, appropriate buffers including wash and cleavage buffers, instruction material, and frozen stocks of host cells.

BRIEF DESCRIPTION OF THE DRAWINGS

FIGS. 3A and 3B differ only in that they are different views of the same protein. The backbone of the molecule is shown in stick formation with highly ordered structures shown as thick arrows (β-sheets) or coiled arrows (α-helices). The lower two panels show the structures of NTHS (left panel) wherein only the backbone of CTHS is shown and CTHS (right panel) wherein only the backbone of NTHS is shown. Exact sequences for NTHS and CTHS are depicted in FIGS. 14 and 15.

FIG. 12 is the amino acid (SEQ ID NO: 1) and nucleotide (SEQ ID NO: 2) sequence of SUMO.

FIG. 13A is the amino acid (SEQ ID NO: 3) and nucleotide (SEQ ID NO: 4) sequences of 6×His-SUMO as it appears in the pET-6×His-SUMO plasmid. FIG. 13C shows the regions (SEQ ID NO: 35) that flank the sequences of 6×His-SUMO (SEQ ID NO: 3).

FIG. 14A shows the amino acid (SEQ ID NO: 5) and nucleotide (SEQ ID NO: 6) sequences of NTHS. FIG. 14B shows the amino acid sequence (SEQ ID NO: 7), nucleotide sequence (SEQ ID NO: 8) of 6×His tagged NTHS as it appears in the pET-6×His-NTHS plasmid.

FIG. 15A shows the amino acid (SEQ ID NO: 9) and nucleotide (SEQ ID NO: 10) sequences of CTHS. FIG. 15B shows the amino acid (SEQ ID NO: 11) and nucleotide (SEQ ID NO: 12) sequence of 6×His-CTHS as it appears in the pET-6×His-CTHS plasmid. FIG. 15D shows the regions (SEQ ID NO: 36) that flank the sequences of 6×His-CTHS (SEQ ID NO: 11).

FIG. 16 is the amino acid (SEQ ID NO: 13) and nucleotide (SEQ ID NO: 14) sequences of GFP (enhanced Green Fluorescent Protein).

FIG. 17 is the amino acid (SEQ ID NO: 15) and nucleotide (SEQ ID NO: 16) sequences of the 6×His-GFP fusion protein as it appears in pET-6×His-GFP, Yep and pFastBac plasmids.

FIG. 18 is the amino acid (SEQ ID NO: 17) and nucleotide (SEQ ID NO: 18) sequences of the 6×His-SUMO-GFP fusion protein as it appears in pET-6×His-SUMO-GFP, Yep and pFastBac plasmids.

FIG. 19 is the amino acid (SEQ ID NO: 19) and nucleotide (SEQ ID NO: 20) sequences of the 6×His-CTHS-GFP fusion protein as it appears in pET-6×His-CTHS-GFP, Yep and pFastBac plasmids.

FIG. 20 is the amino acid (SEQ ID NO: 21) and nucleotide (SEQ ID NO: 22) sequences of GST protein (glutathione transferase) followed by the recognition site for Tev protease.

FIG. 21 is the amino acid (SEQ ID NO: 23) and nucleotide (SEQ ID NO: 24) sequences of GST-6×His-SUMO-GFP fusion as it appears in pET-GST-6×His-SUMO-GFP, Yep and pFastBac plasmids.

FIG. 22 is the amino acid (SEQ ID NO: 25) and nucleotide (SEQ ID NO: 26) sequences of GST-6×His-CTHS-GFP fusion as it appears in pET-GST-6×His-CTHS-GFP, Yep and pFastBac plasmids.

FIG. 23 is the amino acid sequence (SEQ ID NO: 27) and nucleotide sequence (SEQ ID NO: 28) of the Cys-6×His-NTHS protein as it is encoded in pET-Cys-6×His-NTHS.

FIG. 24 is the amino acid (SEQ ID NO: 29) and nucleotide (SEQ ID NO: 30) sequences of catalytic domain of Ulp1 SUMO protease (hydrolase).

FIG. 25 shows the amino acid (SEQ ID NO: 31) and nucleotide (SEQ ID NO: 32) sequences of CTHS-1; the amino acid (SEQ ID NO: 33) and nucleotide (SEQ ID NO: 34) sequence of 6×His-CTHS-1 as it appears in the pET-6×His-CTHS-1 plasmid; the amino acid (SEQ ID NO: 91) and nucleotide (SEQ ID NO: 92) sequences of NTHS-1; and the amino acid (SEQ ID NO: 93) and nucleotide (SEQ ID NO: 94) sequence of 6×His-NTHS-1 as it appears in the pET-6×His-NTHS-1 plasmid.

FIGS. 26A-C show the sequences of the carboxy and amino terminal portions of various Ubls. Two versions of each domain are given. The sequences of domains are extrapolated from the results obtained with SUMO protein and described in the examples.

FIGS. 27A-C show the sequences of the carboxy and amino terminal portions of various Ufds (ubiquitin folding domains). Two versions of each domain are given. The sequences of domains are deduced from solved 3D structures as described in Example VIII.

DETAILED DESCRIPTION OF THE INVENTION

Figure 1:
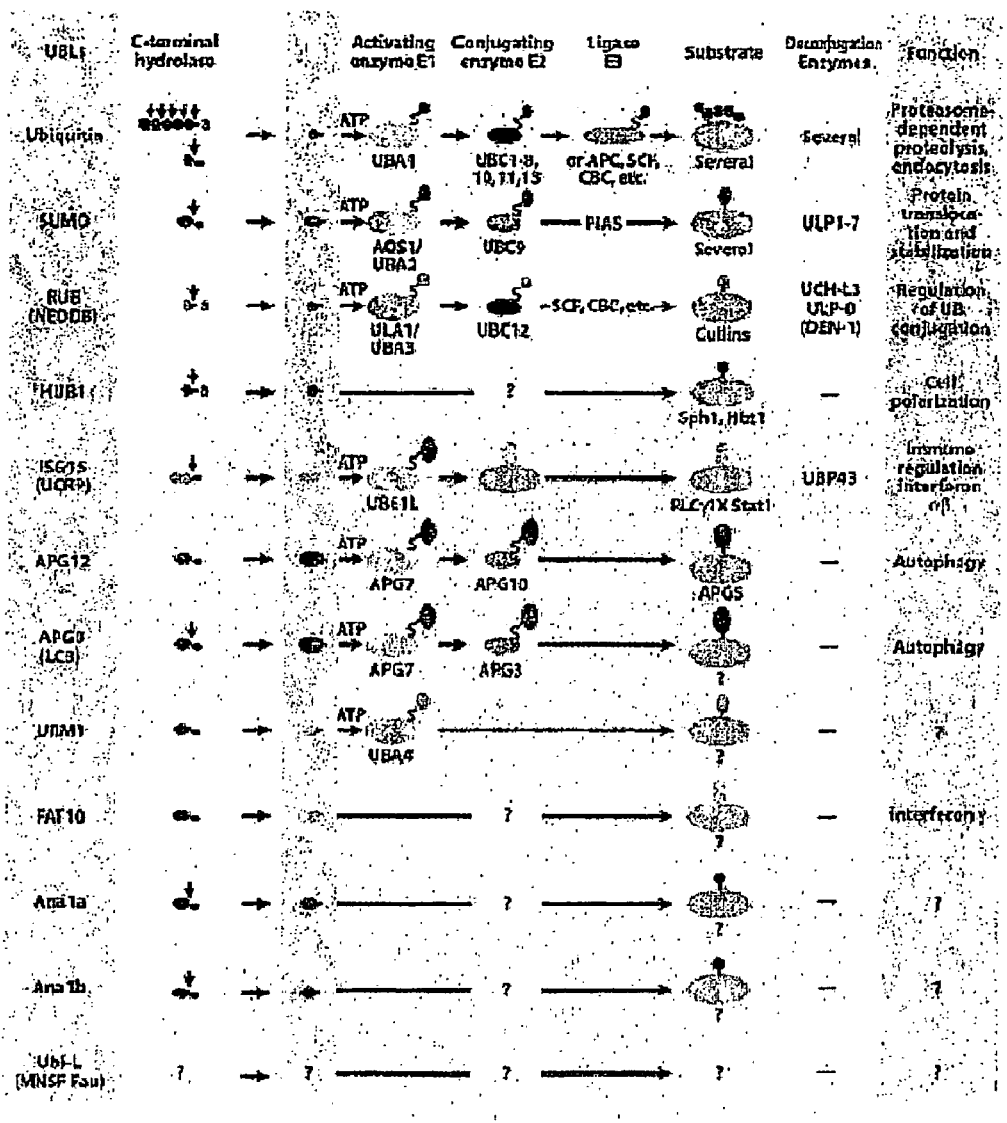
FIG. 1 is a schematic drawing illustrating the conjugation pathways for ubiquitin and ubiquitin-like proteins (Ubls). An arrow in the "C-terminal hydrolase" column indicates the cleavage of the precursor proteins. Only enzymes previously described are provided. The failure to list a particular enzyme in a particular pathway does not preclude the existence of that enzyme.
Figure 2:
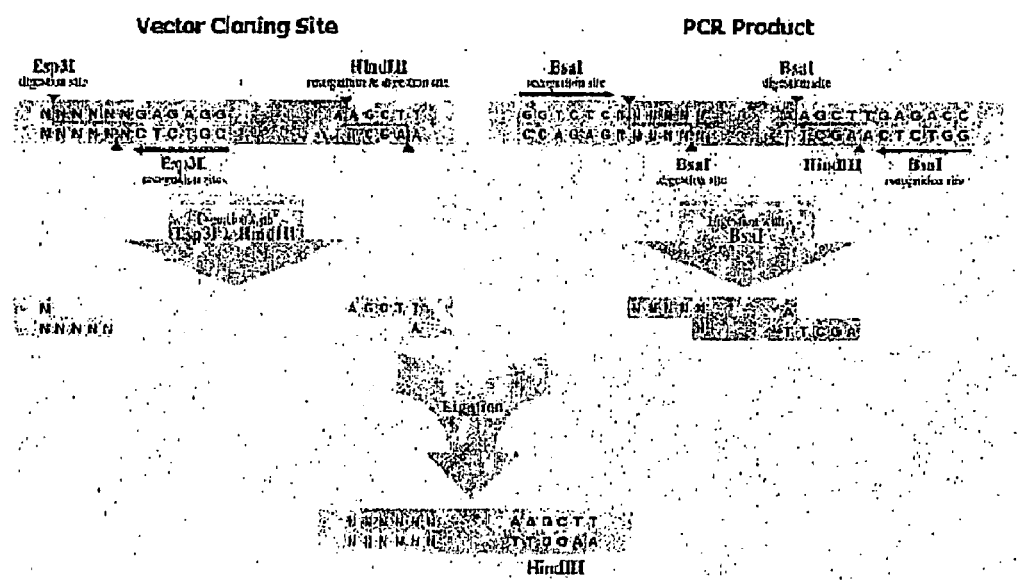
FIG. 2 is a schematic representation of a cloning strategy used to generate CTHS fusion proteins. The sequence identifiers present in this figure include SEQ ID NO: 99 at Esp31 digestion site top, SEQ ID NO: 100 at Esp31 digestion site bottom, SEQ ID NO: 101 at BsaI PCR Product top left, SEQ ID NO: 102 at BsaI PCR Product bottom left, SEQ ID NO: 103 at BsaI PCR Product top right, and SEQ ID NO: 104 at BsaI PCR Product bottom right. In this cloning strategy, the nucleic acid sequence encoding the protein to be expressed as a fusion with CTHS is amplified by PCR with primers that introduce a Bsa I site at the 5' end and HindIII and BsaI sites at the 3' end. The vector encoding for the CTHS contains, in this example, a HindIII site and an Esp31 site at the 3' end of the CTHS encoding region. The PCR product is cleaved by Bsa I and the vector is cleaved by HindIII and an appropriate restriction enzyme (represented here by Esp31) allowing for insertion of the cleaved PCR product into the vector.

There are a number of reasons for the lack of efficient recombinant protein expression in a host, including, for example, short half-life, improper folding, compartmentalization and codon bias. While the Human Genome project has successfully created a DNA "map" of the human genome, the development of protein expression technologies that function uniformly in different expression platforms and for all the protein motifs has not yet been achieved.

In accordance with the present invention, a method for improving the expression of a protein, particularly an unexpressed or poorly expressed protein, in both eukaryotes and prokaryotes is provided. The method comprises attaching a carboxy-terminal portion of a Ubl to the amino-terminus of the protein to be expressed (i.e. protein of interest). The Ubl family of proteins includes, but is not limited to, SUMO, Ub, Rub1, Hub1, ISG15, Ubi-L (MNSF), FAT10, Apg12, Apg8 and Urm1 (12) (see Table 1). A hallmark of all of these proteins, with the exception of APG12, and URM1, is that they are synthesized as precursors and processed by a hydrolase (or protease) at the very carboxy-terminus, usually a di-glycine motif, to generate a mature sequence. Notably, all of the Ubls share a common structure (24,25).

Methods employing fusion proteins comprised of full-length SUMO and other Ubls to obtain expression and purification has been previously described (U.S. application Ser. Nos. 10/338,411 and 10/389,640). Fusion proteins comprising full-length SUMO and a protein of interest remained intact only in *E. coli*. However, in yeast or insect cells the fusion proteins were immediately cleaved, except when proline was the amino-terminal residue of the protein of interest.

Provided herein are methods which allow for the expression of fusion proteins in both eukaryotes and prokaryotes as uncleaved entities. Importantly, this allows for any optionally attached affinity tag (i.e. purification tag) or any other protein or peptide that may be used for purification, detection or any other purpose to remain attached to the expressed protein of interest. Cleavage is only obtained when the Ubl is reconstituted by contacting the protein of interest-carboxy-terminal portion (domain) of the Ubl fusion protein with the amino-terminal portion of the Ubl and subsequently contacted with a specific hydrolase.

The present invention may also be utilized to generate proteins with novel N-termini in eukaryotic cells. The identity of the N-terminus of a protein has been proposed to control its half-life (the N-end Rule) (35). Many important biopharmaceuticals such as growth factors, chemokines, and other cellular proteins, require desired N-termini for therapeutic activity. It has not been possible to generate desired N-termini, as nature initiates translation from methionine. Furthermore, one or more amino acids may be removed from the N-terminus, other amino acids may be added and various covalent modifications may be introduced to the exposed N-termini (26). These modification systems are complex, present in both prokaryotes and eukaryotes and vary to some degree in specificity and performance (27). This means that each recombinantly produced protein that did not undergo in vitro processing by a protease of known specificity may have unexpected and/or heterogeneous N-termini. The full-length SUMO system, as described in U.S. application Ser. Nos. 10/338,411 and 10/389,640, offers a novel way to circumvent this problem for prokaryotic expression systems. According to the instant invention, any amino acid can be incorporated as the N-terminal residue of a protein of interest by altering the appropriate codon in the nucleic acid encoding for the protein of interest. The altered protein of interest is then attached to the carboxy-terminal portion of a Ubl, expressed in a desired cell, and purified as described herein through the reconstitution of the Ubl by contact with the amino-terminal portion of the Ubl and then cleaving the reconstituted Ubl with a specific protease. Alternatively, the amino-terminal domain of the Ubl may be expressed in vivo along with the fusion protein to produce the protein of interest so long as there is specific protease activity in the cell (i.e. native or provided exogenously). Every amino acid except for proline may be employed as the amino-terminal residue by these methods. To employ proline as the amino-terminal residue of the protein of interest, a fusion protein in which the cleavage site of the Ubl protease is followed by the amino acid sequence Met-Pro. Following reconstitution and cleavage with the appropriate protease, the Met-Pro amino-terminus of the protein of interest is further treated with a methionine aminopeptidase (e.g. from *Pyrococcus furiosis*; (28)) to remove methionine and leave proline as the amino-terminus.

Figure 3A:
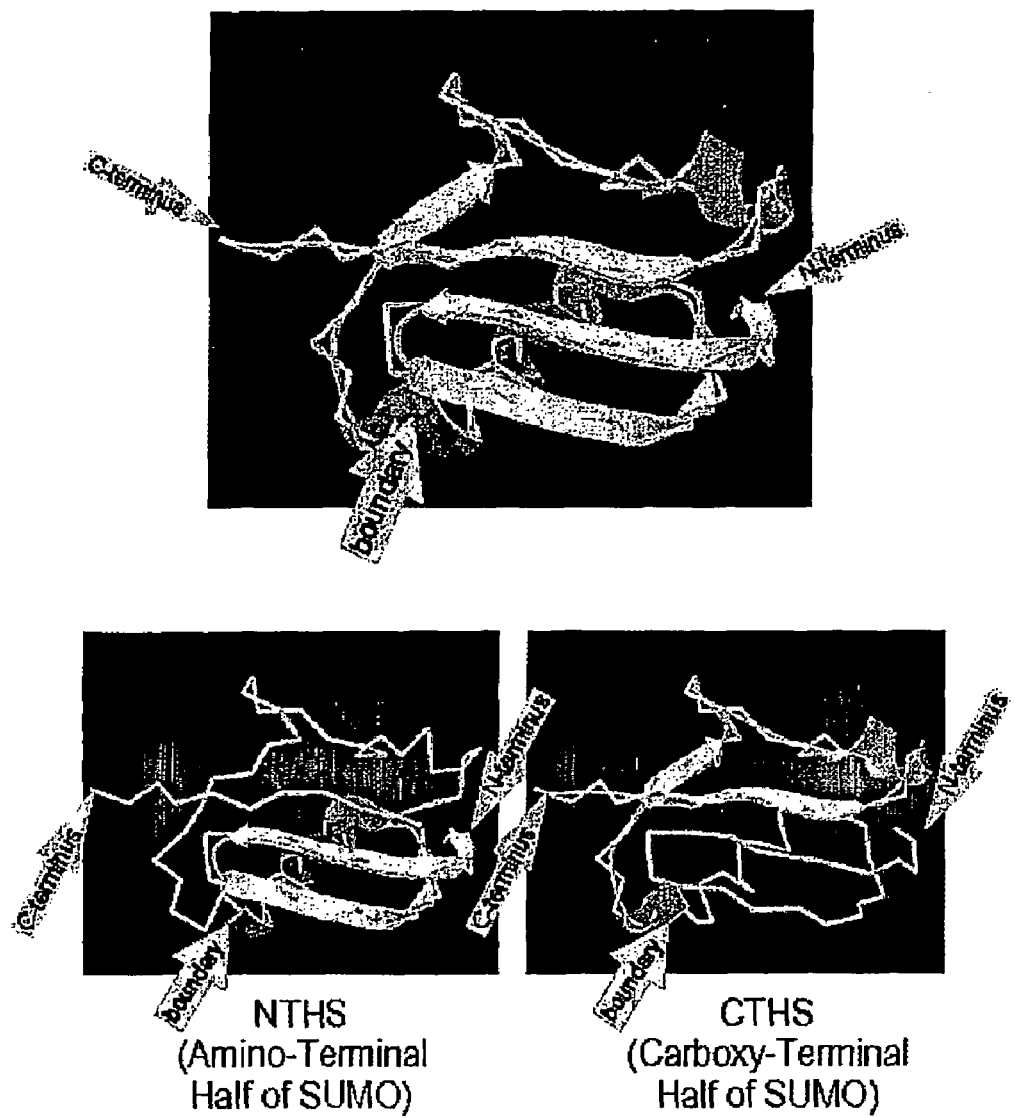
FIGS. 3A and 3B show three-dimensional structures of the SUMO (Smt3) protein (16,17) with the amino and carboxy termini and the boundary between the NTHS and CTHS indicated by arrows.
Figure 3B:
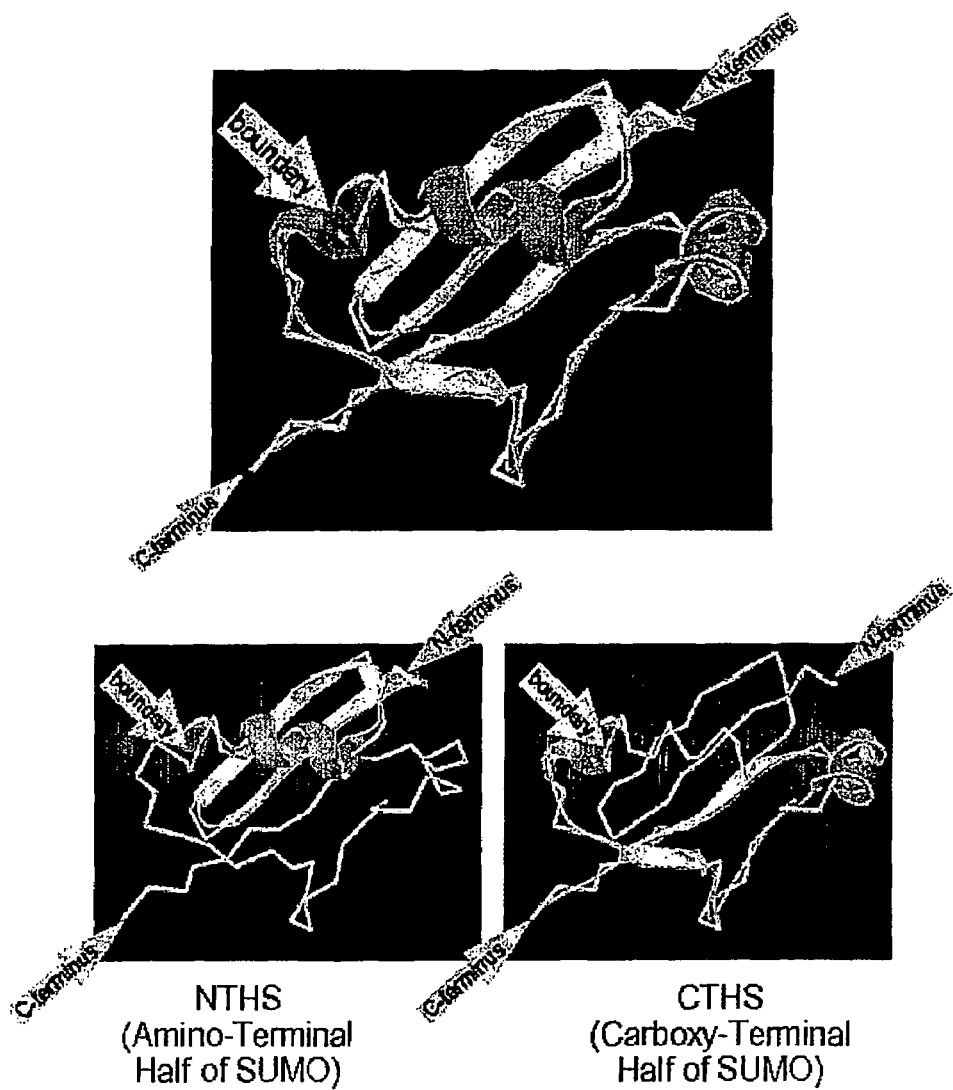

Additionally, methods are provided herein which allow for the high-efficiency affinity purification of the fusion proteins through the exploitation of natural affinity between the partial sequences representing the carboxy-terminal (CTHS) and amino-terminal (NTHS) halves (domains) of SUMO. Importantly, the boundaries of CTHS and NTHS are flexible. Significantly, the instant invention provides two unique and functional forms of the carboxy-terminal domain of SUMO: CTHS (SEQ ID NO: 9) and CTHS-1 SEQ ID NO: 31). Therefore, the instant invention encompasses CTHS and CTHS-1, allelic and species variants, and any other modified CTHSs through either the lengthening of or shortening of the sequence by about 2, 4, 6, 8, 10, 15, and 20 amino acids (or the corresponding changes in nucleotides). Preferably, the modified CTHSs retain at least one of the activities of CTHS (SEQ ID NO: 9) (e.g., increased expression, binding of NTHS (SEQ ID NO: 5)) or a modified NTHS, and/or formation of a cleavable complex with NTHS or modified NTHS). Preferably, the modified CTHS contains the 2β-sheets, as depicted in FIG. 3, in their entirety or a significant portion thereof.

Similarly, modifications in the length of NTHS are encompassed in the present invention. Two unique and functional forms of the amino-terminal domain of SUMO are also provided: NTHS (SEQ ID NO: 5) and NTHS-1 (SEQ ID NO: 91). The instant invention encompasses NTHS and NTHS-1, allelic and species variants, and any other modified NTHSs through either the lengthening of or shortening of the sequence by about 2, 4, 6, 8, 10, 15, and 20 amino acids (or the corresponding changes in nucleotides). Preferably, the modified NTHSs retain at least one of the activities of NTHS (SEQ ID NO: 5) (e.g. the ability to bind CTHS (SEQ ID NO: 9) or a modified CTHS and/or formation of a cleavable complex with CTHS or modified CTHS). Preferably, the modified NTHS contains the 2β-sheets and α-helix, as depicted in FIG. 3, in their entirety or a significant portion thereof.

While any of the Ubls (i.e. their partial sequences, see FIG. 26) set forth in Table 1 may be utilized in the compositions and methods of the invention to 1) enhance expression of heterologous fusion proteins of interest, 2) allow affinity purification of the fusion protein, and 3) reconstitution of the Ubl for cleavage, SUMO is exemplified in the gene fusion system provided herein. While any of the specific hydrolases (i.e. proteases) set forth in Table 2 may be utilized in the compositions and methods of the invention to remove CTHS (or other partial sequence of SUMO protein or other Ubl) from the proteins of interest, Ulp1 is exemplified in the gene fusion system provided herein.

TABLE 1

Properties of Ubiquitin-like Proteins (Ubls)

| Ubls | Function | Knockout phenotype | Substrate | % UB Identity | KDa | Hydro-lase | COOH Residues |
|---|---|---|---|---|---|---|---|
| Ub | Translocation to proteasome | not viable | many | 100 | 8.5 | Numerous | LRLR GG |
| SUMO (SMT3) | Translocation to nucleus | not viable | RanGap, many others | 18 | 11.6 | Ulp1/ Ulp2 | GG |
| RUB1 (NEDD8) | Regulation of mitosis. | viable; non-essential. | Mostly cullins | 60 | 8.7 | Den1/ Ulp8 | GG |
| HUB1 | Cell polarization. | viable; deficient in mating. | Sph1, Hbt1, cell polarity factors | 22 | 8.2 | not known | YY |
| ISG15 (UCRP) | Interferon αβ responses, immune regulation | IFN, LPS hypersensitivity; death | PLCγ1, Stat1, many others | ~30;28 two domains | 15.0 | UBP43 (USP18) | LRLR GG |
| APG12 | Autophagy | viable, defective in autophagy | Apg5 | 18 | 21.1 | not cleaved | FG |
| URM1 | Unknown | ts growth; non-essential. | unknown | 20 | 11.0 | not known | GG |
| APG8 (LC3) | Autophagy | viable; no autophagocytosis or sporulation | phospatidyl-ethanol-amine | 18 | 13.6 | Apg4/ Aut2 | FG |
| FAT10 | Interferon γ responses | unknown | unknown | ~41;30 two domains | 15 | not known | GG |
| Ubi-L (Fau) | immune regulation | unknown | unknown | 35 | 8.3 | not known | GG |

TABLE 2

SUMO Hydrolases/Proteases

| Enzyme | Properties | Reference |
| --- | --- | --- |
| UB1-specific Protease ULP1 | 72 KDa. 621 residues Cleaves linear fusion and SUMO isopeptides bonds. | Li and Hochstrasser, 1999 (29) |
| ULP2 (Yeast) | 117 KDa, 1034 residues Cleaves linear fusions and SUMO isopeptide structures. | Li and Hochstrasser, 2000 (30) |
| SUMO-1 C-Terminal | 30Kda Cleaves linear fusions and SUMO isopeptide structures | Suzuki, et al, 1999 (31) |
| SUMO-1 specific Protease SUSP I (Human) | 126 KDa 1112 residues Specific for SUMO-1 fusion but not Smt3 fusion. Does not cleave isopeptide bond. | Kim, et al, 2000 (18) |
| Sentrin specific Proteases (SENP) SENP1, SENP2 SENP3, SENP4 SENP5, SENP6 SENP7 | All of the SENP enzymes have conserved C-terminal region with core catalytic cysteine. The smallest SENP7 is 238 residues and the largest SENP6 is 1112 residues. | Yeh, et al, 2000 (11) Gong et al, 2000 (32) |

The split SUMO fusion system of the present invention has been successfully applied to express the green fluorescent protein (GFP) in *E. coli* and eukaryotic cells and to purify the final product from all systems. More specifically, the system allows for the: (1) enhancement of the expression of underexpressed proteins; (2) increasing of the solubility of proteins that are insoluble; (3) protecting proteins of interest from degradation by intracellular proteases by fusing partial Ubl sequences to their N-termini; (4) purification of the fusion proteins using immobilized complementing N-terminal part of the respective Ubl; (5) purification of the fusion proteins using immobilized specific antibodies against the Ubl or its part; (6) cleaving the fusion protein in vitro to efficiently generate authentic proteins; (7) generation of proteins with novel N-termini; and (8) cleavage of all fusion proteins with remarkable efficiency irrespective of the N-terminal sequence of the fused protein, using Ubl hydrolases such as SUMO hydrolase Ulp1.

Importantly, Ubl proteases are structure specific enzymes that recognize the entire structure of respective Ubl and not just several amino acid residues (16, 29, 30). On the contrary, most other known proteases, including the ones that are commonly used in recombinant protein processing, recognize small (4-8) and degenerate stretches of amino acid sequence and, as a consequence, often cleave within the protein of interest. The combination of properties of the Ubls (as noted hereinabove) with the specificity and robustness of the respective proteases creates a superior system for recombinant protein expression, purification and processing.

The ultimate fate of ubiquitinated or sumoylated proteins within a cell varies. A protein can be monoubiquitinated or polyubiquitinated. Monoubiquitination of proteins mainly regulates protein internalization (33). Ubiquitination primarily targets proteins to 26S proteasome for degradation (34). On the other hand, sumoylation of target proteins does not lead to degradation, but, rather, leads directly or indirectly to altered localization of proteins (10). There are about 50 deubiquitinating enzymes in human and 17 in yeast genomes, respectively. These enzymes cleave conjugated ubiquitin from target proteins as well as ubiquitin-ubiquitin and ubiquitin artificial-fusion proteins (35, 36). Yeast has two proteases, called Ulp1 and Ulp2, that remove SUMO from ε-amino groups of lysine as well from the linear SUMO-fusions (29, 30).

As compared to deubiquitinating enzymes, which are notoriously unstable (36, 37), Ulp1 is known to produce remarkable yields and to be highly stable and robust in its digestion properties. This dramatic difference between UBP and Ulp enzyme classes is not surprising since there is essentially no similarities between the two on the level of amino acid sequence or tertiary structure (16, 38). Since CTHS fusion can both enhance recombinant protein yield, provide means of protein purifications, and generate new N-termini, this technology provides an important tool for post-genomic biotechnology analyses.

The present invention also encompasses kits for use in effecting enhanced expression, secretion, purification, localization, and alteration of the amino terminus of a protein of interest. Such kits comprise a recombinant vector containing a nucleic acid sequence encoding a carboxy-terminal portion of a UBL molecule selected from the group of SUMO, Ub, RUB, HUB, APG8, APG12, URM1, Ubi-L, FAT10 and ISG15 operably linked to a promoter suitable for expression in the desired host cell and a multiple cloning site suitable for cloning a nucleic acid encoding the protein of interest in-frame with the nucleic acid sequence encoding the carboxy-terminal portion of the UBL molecule. The promoter is preferably a strong promoter and may be constitutive or regulated. Such promoters are well known in the art and include, but are not limited to, the promoters provided hereinbelow such as the ADH1, T7, and CUP-1 promoters.

The recombinant vector may also contain a nucleic acid sequence encoding at least one purification tag in-frame with the sequence encoding the carboxy-terminal portion of the Ubl molecule. Purification tags are well known in the art (see Sambrook et al., 2001, Molecular Cloning, Cold Spring Harbor Laboratory) and include, but are not limited to: polyhistidine tags, polyarginine tags, glutathione-S-transferase (GST), maltose binding protein (MBP), S-tag, influenza virus HA tag, thioredoxin, staphylococcal protein A tag, the FLAG™ epitope (DYKDDDDK; SEQ ID NO: 140), AviTag epitope (for subsequent biotinylation), and the c-myc epitope. Materials and methods for the purification of fusion proteins via purification tags are also well known in the art (see Sambrook et al., Novagen catalog, 2002, examples hereinbelow). Reagents including, but not limited to, at least one solid support capable of binding the purification tag, lysis buffers, wash buffers, and elution buffers may also be included in the kits.

The kit may further comprise a composition comprising a preparation of an amino-terminal portion of the Ubl molecule. The kit may also include a recombinant vector containing a nucleic acid sequence encoding an amino-terminal portion of the Ubl molecule optionally operably linked to at least one purification tag. The kits may also further comprise a composition comprising at least one protease capable of cleaving the UBL molecule from the fusion protein, cleavage buffers, frozen stocks of host cells, and instruction manuals. The kits may also further comprise reagents for altering the nucleic acid encoding a protein of interest to generate amino termini which are different from those native to the wild-type protein. Methods for altering the nucleic acid are well known in the art and include, but are not limited to, site-directed mutagenesis and oligonucleotide-based site-directed mutagenesis (see BD Biosciences Catalog, 2001; Qiagen Catalog, 2001; Ausubel et al., eds., 1995, Current Protocols in Molecular Biology, John Wiley and Sons, Inc.).

As used herein, an "instructional material" includes a publication, a recording, a diagram, or any other medium of expression which can be used to communicate the usefulness of the composition of the invention for performing a method of the invention. The instructional material of the kit of the invention can, for example, be affixed to a container which contains a kit of the invention to be shipped together with a container which contains the kit. Alternatively, the instructional material can be shipped separately from the container with the intention that the instructional material and kit be used cooperatively by the recipient.

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary-sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$Tm=81.5°\ C.+16.6\ \text{Log}\ [Na+]+0.41(\%\ G+C)-0.63(\%\ \text{formamide})-600/\#bp\ \text{in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. For example, hybridizations may be performed, according to the method of Sambrook et al., (supra) using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence. The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be lo attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

The phrase "operably linked," as used herein, may refer to a nucleic acid sequence placed into a functional relationship with another nucleic acid sequence. Examples of nucleic acid sequences that may be operably linked include, without limitation, promoters, cleavage sites, purification tags, transcription terminators, enhancers or activators and heterologous genes which when transcribed and, if appropriate to, translated will produce a functional product such as a protein, ribozyme or RNA molecule. The phrase "operably linked" may also, for example, refer to a nucleic acid sequence encoding a protein of interest placed in functional relationship with a nucleic acid encoding the carboxy-terminal domain of a Ubl such that the catalytic cleavage activity of the carboxy-terminal domain of a Ubl in proteinaceous form leads to the release of the protein of interest.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

The phrases "affinity tag," "purification tag," and "epitope tag" may all refer to tags that can be used to effect the purification of a protein of interest. Purification/affinity/epitope tags are well known in the art (see Sambrook et al., 2001, Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag epitope (for subsequent biotinylation), dihydrofolate reductase (DHFR), an antibody epitope (e.g., a sequence of amino acids recognized and bound by an antibody), and the c-myc epitope.

The materials and methods set forth below are provided to facilitate the practice of the present invention.

Design and Construction of *E. coli* Expression Vectors

Figure 13B:
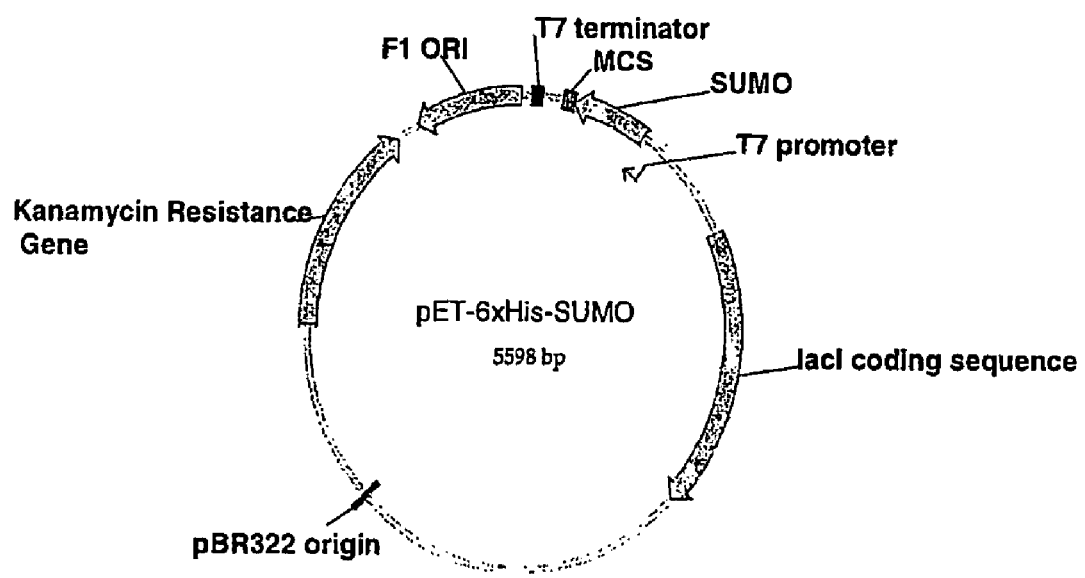
FIG. 13B is a map of the pET-6×His-SUMO plasmid.
Figure 15C:
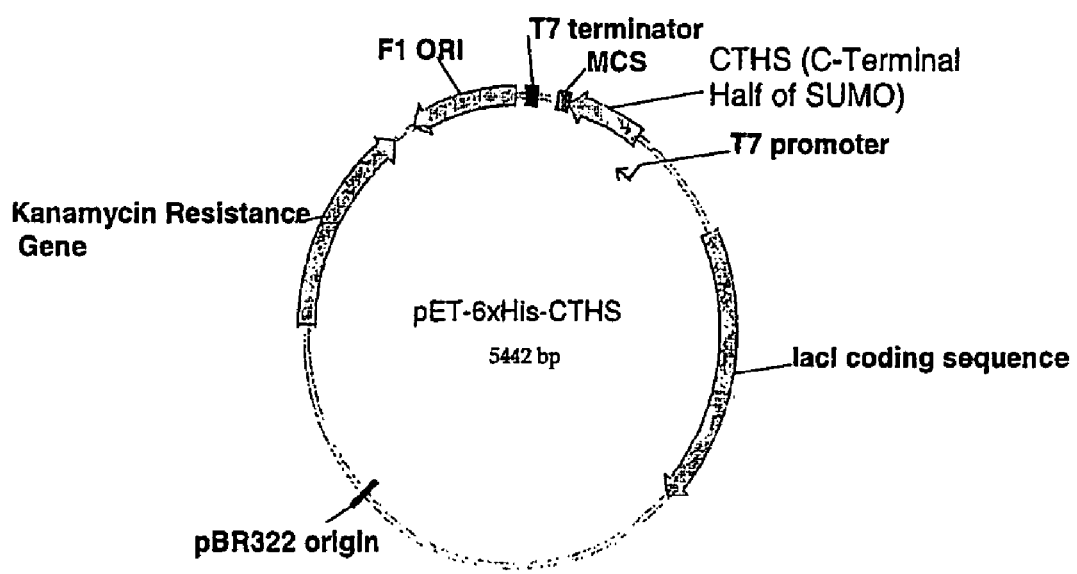
FIG. 15C is a map of the pET-6× His-CTHS plasmid.

The original vector backbone was developed using pET 24d vector from Novagen (see FIGS. 13B and 15C). pET24d uses a T7 promoter system that is inducible with IPTG. The vector has a kanamycin selection marker and does not contain any translation terminator. Similar vectors using pET22 backbone, which carries a gene for ampicillin resistance, was also produced.

Construction of 6×His-SUMO-GFP Cleavable and Uncleavable Fusions

An amino-terminal 6×His-tagged SUMO fusion vector was constructed as follows. A PCR product was generated with the primers 5'CCATGGGTCATCACCATCATCAT-CACGGGTCGGACTCAGAAGTCAATC AA-3' (SEQ ID NO: 69) and 5'-GGATCCGGTCTCAACCTCCAATC TGT-TCGCGGTGAG-3' (SEQ ID NO: 70) using a modified SUMO (Smt3) gene as a template ((39) kind gift of Erica Johnson). Specifically, the SUMO (SEQ ID NO: 2) used throughout the examples provided herein contains an adenine nucleotide at position 229 in place of a guanine nucleotide reported in the reported SUMO sequence (GenBank accession number U27233). This alteration produces an alanine instead of a threonine in the encoded amino acid sequence (compare SEQ ID NO: 1 with GenBank Accession No. Q12306). Although the following examples employ the altered version of SUMO, the instant invention includes the utilization of the "wild-type" SUMO as provided in the above listed GenBank Accession Nos.

The PCR fragment was double digested with Nco I and Bam HI, and then ligated into pET24d, which had been similarly digested. The eGFP sequence was amplified with the primers 5'-GGTCTCAAGGTATGGTGAGCAAGGGC-GAGGAGC-3' (SEQ ID NO: 71) and 5'-AAGCTTATTACT-TGTACAGCTCGT CCATGCC-3'(SEQ ID NO: 72). To generate an uncleavable variant of SUMO-GFP fusion, a primer with proline codon in place of methionine (all shown in bold) was used for PCR amplification: 5'-GGTCTCAAGGTC-CCGTGAGCAAGGGCGAGGAGC-3' (SEQ ID NO: 73). The PCR products were purified and double digested with Bsa I and Hind III, these were then ligated into the pET24d-6×His-SUMO vector which had been similarly digested. Plasmids were sequenced to confirm the presence of correct sequence in each.

Construction of pET-6×His-NTHS and pET-Cys-6×His-NTHS Plasmids

The pET-×His-NTHS plasmid (FIG. 14) was constructed by inverse PCR using pET-6×His-SUMO-GFP plasmid (FIG. 18). The primers 5'-TTTTTTAAGCTTGCGGCCG-CACTCG-3' (SEQ ID NO: 74) and 5'-TTITTTAAGCT-TATTTAGCGAACGCTTCCATC-3'(SEQ ID NO: 75) were used to amplify the plasmid and to delete the C-terminal half of SUMO gene and the GFP gene. The amplified product was digested with Hind III restriction endonuclease and self-ligated. To introduce the cysteine residue close to the N-terminus of NTHS (FIG. 23, SEQ ID: 27) so that the covalent coupling to solid support (e.g. Sulfo-link resin, Pierce; and supports possessing thiopropyl, iodopropyl, and other thiol reactive groups) can be achieved, primers of the following sequences 5'-GATATACCATGGGTTGCCATCACCATC-3' (SEQ ID NO: 76) and 5'-GATGGCAACCCATGG-TATATCTCC-3'(SEQ ID NO: 77) were used for inverse PCR. The template was pET-6×His-NTHS (FIG. 14). After completion of PCR, the product was purified, digested with Nco I and self ligated.

Construction of pET-6×His-CTHS-GFP, pET-6×His-E-CTHS-GFP and pET-S-6×His-CTHS-GFP Plasmids The pET-6×His-CTHS-GFP plasmid was constructed by inverse PCR using pET-6×His-SUMO-GFP plasmid. The primers 5'-TTTTTTGGTTCTCGTCATCATCACAAAA-GACAGGGTAAGGAAATG-3'(SEQ ID NO: 78) and 5'-TTTTTTGGTCTCGATGATGGTGATGACCCATGG-3' (SEQ ID NO: 79) were used to amplify the plasmid and to delete the N-terminal part of SUMO gene. The amplified product was digested with Bsa I restriction endonuclease and self-ligated.

To replace lysine with the glutamic acid residue (E in single letter code, hence the name of the plasmid) after 6×His-tag, so that the 6×His-tag can be protected from clipping by endopeptidases the PCR and cloning was performed as above except that primer of the following sequence 5'-TTTTTTG-GTCTCGTCATCATCACGAAAGACAGGG-TAAGGAAATG-3' (SEQ ID NO: 80) was used instead of (SEQ ID NO: 78).

To introduce the part of S-tag sequence (40) so that the 6×His-tag can be protected from clipping by exopeptidases the following two oligonucleotides were designed in such a way that upon annealing they form two Nco I compatible overhangs:

```
                                                    (SEQ ID NO: 81)
5'-CATGGAAACCGCTGCTGCTAAATTCGAACGCCAGCA-3'
and
                                                    (SEQ ID NO: 82)
5'-CATGTGCTGGCGTTCGAATTTAGCAGCAGCGGTTTC-3'.
```

These were phosphorylated by a T4 DNA kinase annealed and cloned into Nco I digested pET-6×His-CTHS-GFP.

Construction of pET-GST-6×His-SUMO-GFP and pET-GST-6×His-CTHS GFP Plasmids

The pET-GST-6×His-SUMO-GFP plasmid (FIG. 21, SEQ ID: 24) was constructed by inserting a PCR amplified GST sequence (FIG. 20, SEQ ID: 22) into Nco I site of pET-6× His-SUMO-GFP plasmid. GST sequence was amplified from pET-GST plasmid using the primers 5'-TTTTTTCGTCTC-CCATGTCCCTATACTAGGTTAATTG-3' (SEQ ID: 83) and 5'-TTTTTTTCCATGGCACCTTGAAAATAAAGAT-3' (SEQ ID: 84) and the PCR product was digested with Esp3 I and Nco I. pET-GST-6×His-CTHS-GFP (FIG. 22, SEQ ID: 26) was produced by inverse PCR using pET-GST-6×His-SUMO-GFP plasmid as a template. The primers 5'-TTTTTTGTCTCGTCATCATCACAAAAGA-CAGGGTAAGGAAATG-3' (SEQ ID NO: 78) and 5'-TTTTTTGGTCTCGATGATGGTGATGACCCATGG-3' (SEQ ID NO: 79) were used to amplify the plasmid and to delete the N-terminal part of SUMO gene. The amplified product was digested with Bsa I restriction endonuclease and self-ligated.

Ulp1 Plasmid, Expression and Purification of SUMO Protease

The catalytic domain of SUMO hydrolase/protease Ulp (403-621)p (16, 29) was PCR amplified from yeast genomic DNA using the primers 5'-TTTTTTTCCATGGGACTTGT-TCCTGAATTAAATGAA-3' (SEQ ID: 85) and 5'-TTTTTTCTCGAGTTTTAAAGCGTCGGT-TAAAATCAA-3' (SEQ ID: 86). PCR product was digested with Nco I and Xho I and cloned into pET24d vector digested with Nco I and Xho I. The resulting clone carried a catalytic domain of Ulp1 in frame with C-terminal His-tag. The enzyme was expressed in Rosetta(DE3) pLysS (Novagen). The recombinant protein was purified using Ni-NTA agarose (Qiagen) and extensively dialyzed against 20 mM Tris-HCl pH 8.0, 150 mM NaCl and 5 mM β-mercaptoethanol. Prior to storage at −80° C. the enzyme preparations were adjusted to 50% glycerol.

Design and Construction of Yeast Vectors

*Saccharomyces cerevisiae* has been used as a model for experiments involving yeast. All of the expression vectors for these studies were designed on pYep that is a multicopy yeast vector with tryptophan as a selectable marker, 2µ as an origin of replication and a copper induced promoter that drives expression of cloned genes of interest (41). Fusion constructs (Nco I-Xho I fragments excised from *E. coli* vectors) were directly recloned into pYep digested with Nco I and Xho I.

Design and Construction of Recombinant Baculovirus and Expression of Fusions in Insect Cells To demonstrate that CTHS-GFP fusion is produced as uncleaved protein which can be subsequently cleaved in vitro by contacting with NTHS and Ulp1 we used pFastBac I vector (Invitrogen). Fusion construct (Nco I-Xho I fragments excised from *E. coli* vectors pET-GST-6×His-CTHS-GFP, FIG. 22, SEQ ID: 26) was directly recloned into pFastBac I digested with Nco I and Xho I.

Analysis of Proteins from Insect Cell Compartments: Preparation of Baculovirus Stocks and Cell Growth Transfer vector constructs based on the pFastbac 1 shuttle plasmid (Invitrogen, Inc.) were transposed in DH10Bac *E. coli* competent cells to transfer the GST-6×His-CTHS-GFP sequence into recombinant virus DNA by site-specific integration. After alkaline lysis of transformed (white colonies) of *E. coli* cells, which contain recombinant virus (bacmid) DNA, and extraction of the recombinant bacmid DNA, the bacmid DNA was used to transfect *Spodoptera frugiperda* (Sf9) insect cells, in which virus replication occurs. The virus was then amplified to produce passage 2 (for long-term storage) and passage 3 virus (for working) stocks by infection of fresh Sf9 cell cultures and used directly to infect cells for fusion protein expression. Virus infectivity (pfu/ml) was determined by titration in Sf9 cells using the BacPAK™ Rapid Titer Kit (BD Sciences Clontech, Inc.). A 50 ml culture of Hi-Five cells at concentration of $1 \times 10^6$ cells/ml, was infected with recombinant virus at MOI=5 in Express Five media (serum free media). The cells were grown in 100 ml spinner flask at 27° C. Every 24 hours, cell viability was determined by trypan blue and cell counting 0.5 ml of the suspension The presence of recombinant protein in cells and media was ascertained by SDS-PAGE and Western blotting of supernatant and cell pellets.

*S. cerevisiae* Growth and Protein Expression

Yeast cultures were grown in rich medium. Standard yeast and *E. coli* media were prepared as described (42). The yeast strain BJ 1991 was used as a host. Yeast transformation was performed according to published procedures (43). Yeast transformants with autonomously replicating plasmids were maintained in yeast selective media. The 6×His-CTHS-GFP (cleavable or uncleavable variants) as well as S-6×His-CTHS-GFP and 6×His-E-CTHS-GFP fusions were expressed under the regulation of copper metallothioneine (CUP1) promoter in 2 µm multicopy plasmids with the TRP selective marker.

Yeast cells were transformed with appropriate expression vectors, and single colonies were grown in synthetic media minus the selectable marker. For each protein, at least two single colonies were independently analyzed for protein expression. Cells were grown in 5 ml culture overnight and, in the morning, the culture was diluted to an $OD_{600}$=0.5 with fresh medium. Culture was allowed to grow until $OD_{600}$=2.0 and copper sulfate was added to 100 µM. The culture was induced for three hours. Cells were pelleted at 2000×g for 5 minutes, washed with 10 mM Tris-EDTA buffer pH 7.5. Cell pellet was suspended in SDS-PAGE buffer and boiled for 5 min and briefly sonicated to shear the DNA. The suspension was centrifuged, and 10-20 µl aliquots were run on 12% SDS-PAGE.

*E. coli* Growth and Protein Expression

Protein expression studies were carried out in the Rosetta bacterial strain (Novagen). This strain is derived from the lambda DE3 lysogen strain and carries a chromosomal copy of the IPTG inducible T7 RNA polymerase along with tRNAs on a pACYC based plasmid. Cultures were grown in L3 as well as minimal media and at growth temperatures of 37° C. with 100 µg/mL Kanamycin and 30 µg/mL chloramphenicol. The culture was diluted 50 fold and grown to mid log (OD at 600 nm=0.5-0.7), at which time the temperature was reduced to 26° C. and the culture was induced with 1 mM IPTG. Induction was allowed to proceed for 2-5 hrs. To analyze protein induction in total cells, SDS-PAGE buffer was added and the protein was analyzed following SDS-PAGE and staining with Coomassie blue.

Separation of Soluble and Insoluble Fractions

E. coli were harvested by mild centrifugation and washed once with PBS buffer. Cells were resuspended in 4 ml of PBS and ruptured by several pulses of sonication. Unbroken cells were removed by mild centrifugation (5 min at 1500×g) and supernatants were sonicated again to ensure complete cell lysis. An aliquot (5 µl) was mixed with 2% SDS to ensure that no viscosity is detected owing to lysis of unbroken cells. After ensuring that no unbroken cells remained in the lysate, insoluble material consisting of cell walls, inclusion bodies and membrane fragments was sedimented by centrifugation (18,000×g for 10 min). The supernatant was considered the "soluble fraction".

The pellets were washed from any remaining soluble proteins, lipids and peptidoglycan as follows. Pellets were resuspended in 600 µl of PBS and to the suspensions 600 µl of solution containing 3 M urea and 1% Triton X100 was added. The suspension was briefly vortexed and insoluble material was collected by centrifugation as above. The PBS/Urea/Triton wash was repeated two more times to ensure complete removal of soluble proteins. The washed pellets, designated as "insoluble fraction," consisted primarily of inclusion bodies formed by over expressed proteins. Approximately 10 µg of protein from each fraction was resolved on 12% SDS-PAGE minigels and stained with Coomassie Brilliant Blue.

Fluorescence (GFP Activity) Assessment

GFP fluorescence (9) was measured in soluble fractions (approx. 0.1 mg of soluble protein in a final volume of 40 µl) using Fluoroscan Accent FL fluorimeter (LabSystems; Helsinki, Finland) with Excitation 485 nm/ Emission 510 nm filter set is with the exposure set to 0.4 sec. The data are presented in Arbitrary Units (AU).

Western Blotting

Twenty µg of total yeast protein per lane were resolved on 12% SDS-PAGE minigel and electro-blotted onto nitrocellulose membranes by standard methods. Prior to blocking and incubation with the antibodies the membranes were stained with Ponceau S solution (Sigma) to ensure equal protein amount in the samples. Membranes were blocked with 5% milk in TTBS buffer and incubated with rabbit anti-GFP antibodies (Clontech, cat no. 8367) at 1:500 dilution overnight at 4° C. Secondary HRP-conjugated antibodies were from Amersham.

Protein Purification and In Vitro Cleavage with Ulp1.

The recombinant proteins from soluble fractions of the lysates were purified using Ni-NTA agarose (Qiagen) using procedures recommended by the manufacturer and further detailed in EXAMPLE VI. Cleavage of the protein was performed as detailed in EXAMPLE VI.

The following examples are provided to illustrate various embodiments of the present invention. SUMO is exemplified in the following examples, however the other Ubls may be employed instead. The examples are illustrative and are not intended to limit the invention in any way.

EXAMPLE I

Figure 5A:
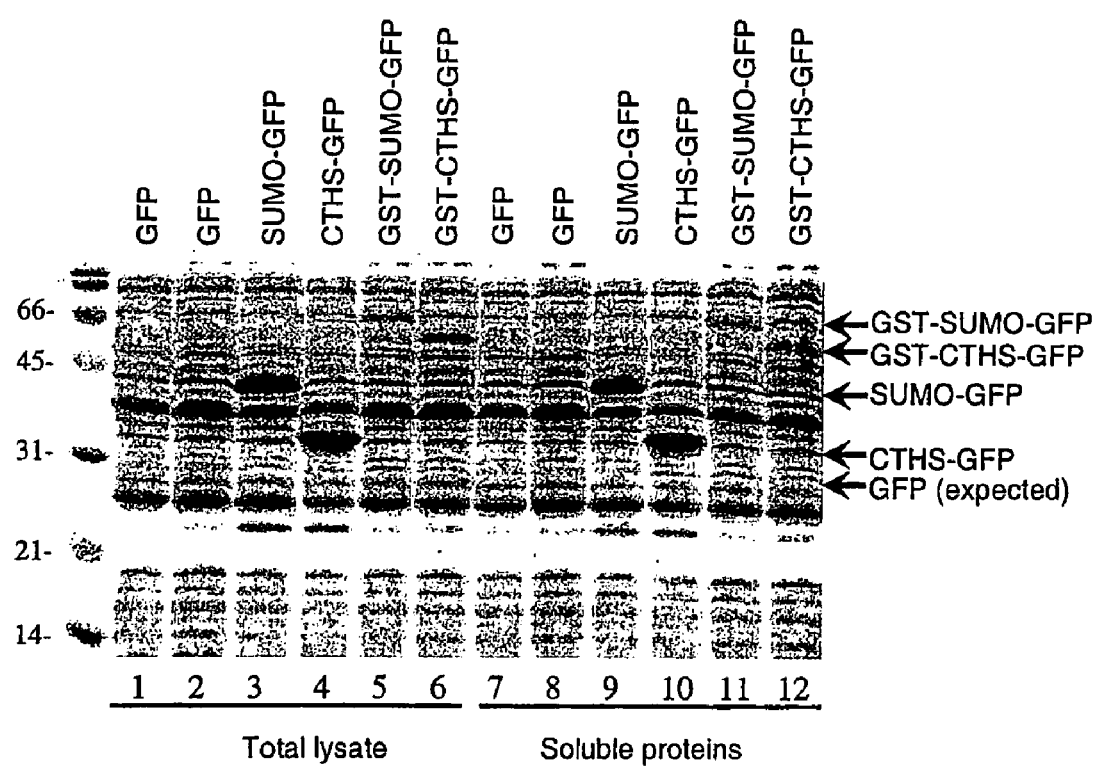
FIG. 5A shows a Coomassie stained gel that demonstrates that the attachment of the CTHS to the amino-terminus of target proteins increases the expression and/or enhances the solubility of the protein in E. coli.
Figure 5B:
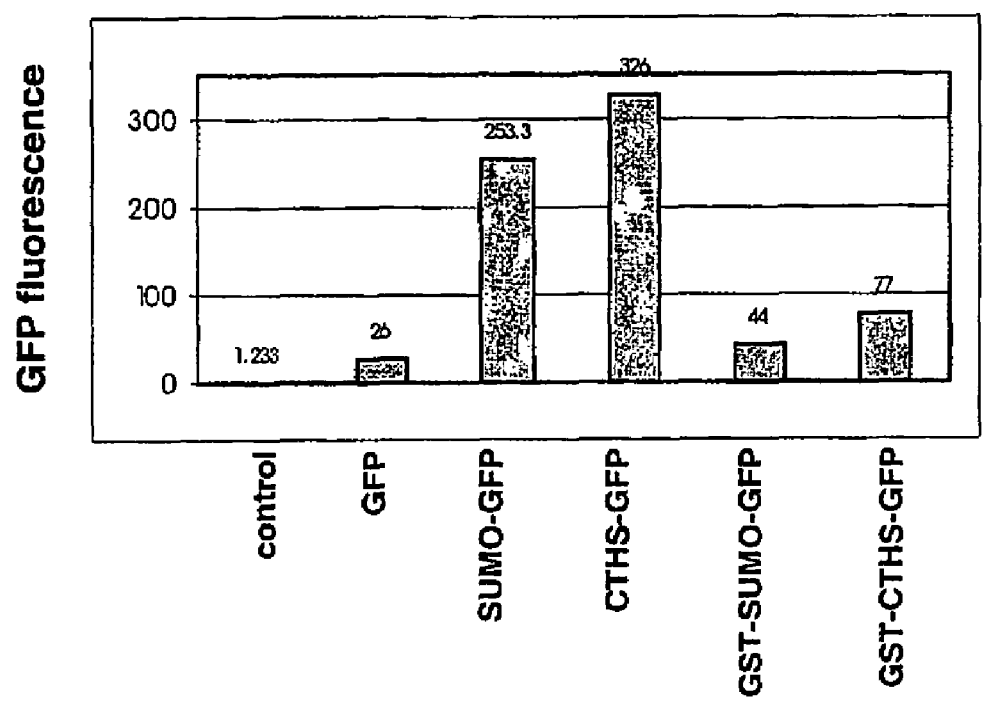
FIG. 5B is a graph of the intensity of fluorescence (in Arbitrary Units (AU) as measured in a Fluorscan Ascent FL fluorometer, LabSystems) in soluble fractions obtained from the cells expressing the various constructs. Green fluorescence protein (6×His-GFP), 6×His-CTHS-GFP, 6×His-SUMO-GFP, GST-6×His-CTHS-GFP, and GST-6×His-SUMO-GFP fusions encoded in pET24d E. coli expression vectors were expressed in the E. coli Rosetta pLysS strain (Novagen). Expression was induced at 26° C. with 1 mM IPTG for two hours in LB medium. Lanes 1-6 represent total cellular protein and lanes 7-12 represent soluble proteins. The first lane of the gel contains molecular weight markers of the size indicated by the numbers to the left of the gel. Arrows indicate the migration position of the fusion proteins.

Attachment of Carboxy-Terminal Half of SUMO (CTHS) to N-Terminus of GFP Enhances the Expression of the Protein in E. coli The design and construction of all the pET vectors expressing GFP has been described above. The DNA sequences, accession numbers of the SUMO, CTHS, GST, GFP, the fusion constructs, plasmid maps, and translation frames are shown in FIGS. 12-24. FIG. 5 shows the expression pattern of 6×His-GFP, 6×His-SUMO-GFP, 6×His-CTHS-GFP, GST-6× His-SUMO-GFP, and GST-6×His-CTHS-GFP. Induced E. coli cells were ruptured by sonication and soluble proteins were analyzed on SDS-polyacrylamide gels. The stained gel shows (FIG. 5A) that the fusions were soluble. Un-fused GFP is generally poorly expressed in E. coli. The data show that SUMO and CTHS with and without attachment of GST enhance the expression level of GFP to varying degrees. FIG. 5B shows GFP fluorescence in approximately 0.1 mg of soluble protein in a final volume of 40 µl using Fluoroscan Accent FL fluorometer (LabSystems). The data are presented in Arbitrary Units (AU) and show that SUMO, CTHS and their fusions with GST produced GFP protein that was able to fluoresce and, thus, folded correctly (9). Notably, CTHS fusion proteins consistently and reproducibly produced more GFP than the fusions with full-length SUMO. In addition to data presented here we constructed a shorter version of CTHS (CTHS-1, FIG. 25, SEQ IDs: 31-34). Analysis of the expressed CTHS-1-GFP fusion demonstrated that expression levels similar to CTHS are obtained indicating that the boundary between CTES and NTHS is relatively flexible and may be varied according to specific application.

Overall, these results show that in bacteria, fusion of CTHS to GFP increases the level of expression 10-40 fold (based on protein band appearance on the SDS-PAGE) or 3-12 fold (based on fluorescence comparison). The difference in these estimates is explained by effective quenching of GFP fluorescence in solutions with high concentration of proteins such as cell lysates.

EXAMPLE II

Attachment of Carboxy-Terminal Half of SUMO (CTHS) to the N-Terminus of GFP Enhances the Expression of the Protein in Yeast Without Cleavage The design and construction of all the Yep-based plasmids expressing various fusions of GFP and the methods for protein expression analysis have been described in detail above. Briefly, the constructs initially made in the pET24 vector were excised and recloned into the YEp vector. The transformants were selected on medium lacking tryptophan. Expression was induced for three hours and the proteins were analyzed by western blot with anti-GFP antibodies.

Figure 6A:
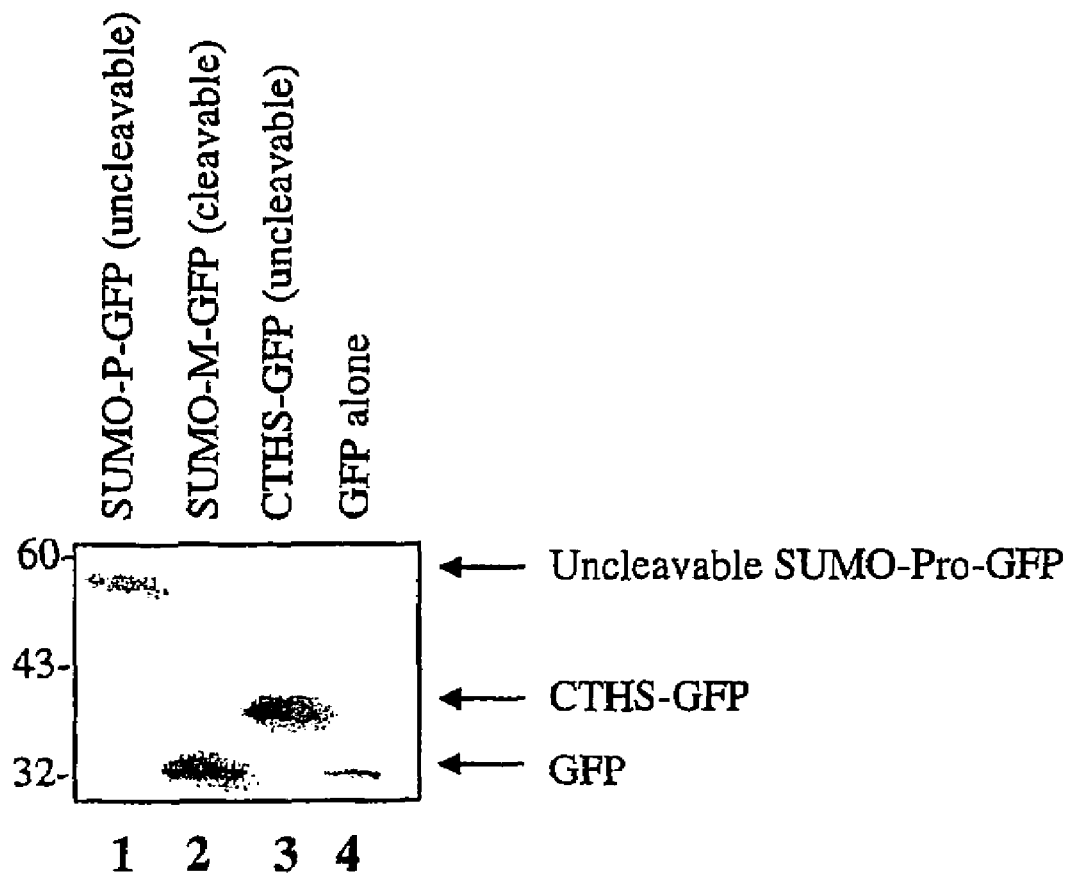
FIG. 6A is a Western blot of 6×His-CTHS-GFP fusion proteins expressed in yeast cells demonstrating that the attachment of the CTHS to the amino-terminus of target protein increases expression of the protein and CTHS-GFP fusions are not cleaved in yeast. Yeast strain BJ1991 was transformed with one of the following plasmids: 6×His-CTHS-GFP, 6×His-SUMO-Met-GFP (cleavable), 6×His-SUMO-Pro-GFP (uncleavable), or 6×His-GFP. The plasmids express the fusion proteins under the control of a copper sulfate regulated promoter. Total cell extracts were prepared by boiling the cells in SDS-PAGE buffer and briefly sonicating the sample to reduce viscosity. 20 μg of the total yeast proteins were resolved on 15% SDS-PAGE minigel and analyzed by Western blot with a rabbit polyclonal antibody against GFP and a secondary HRP-conjugated antibody.
Figure 6B:
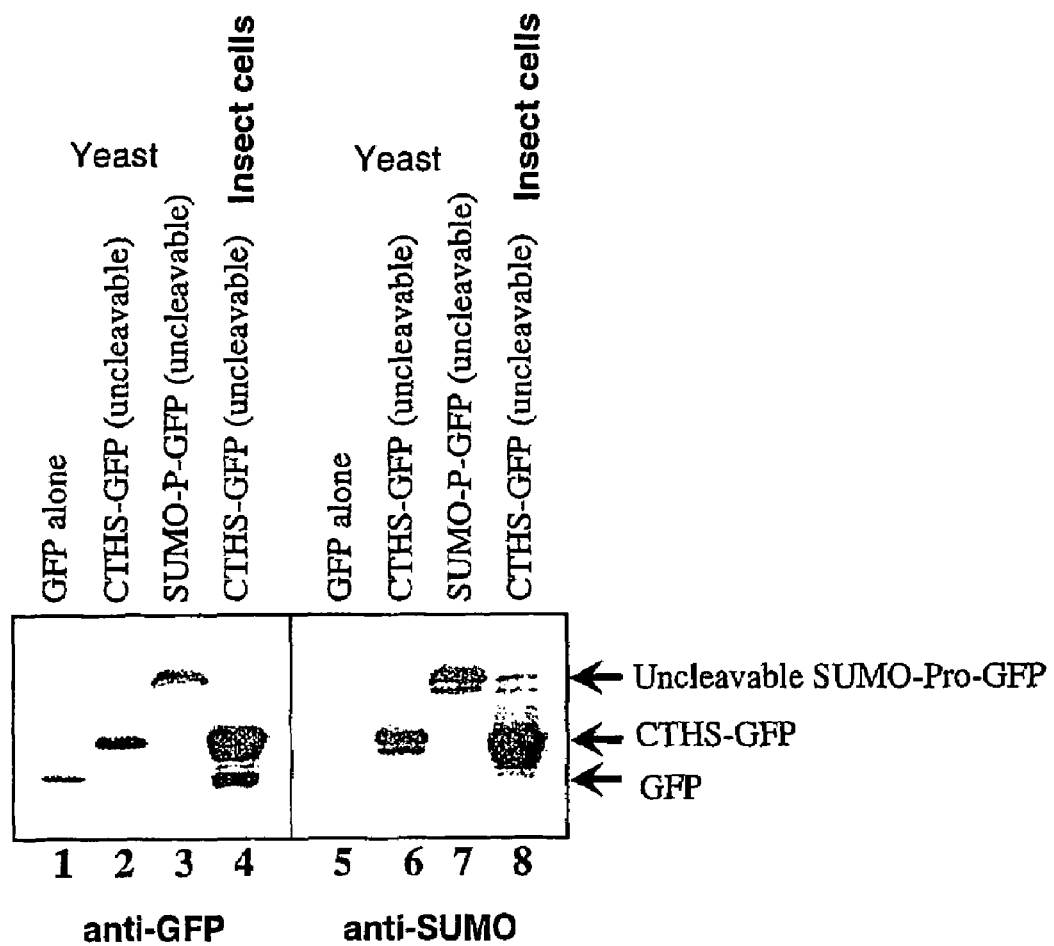
FIG. 6B is a Western blot of 6×His-CTHS-GFP fusion proteins expressed in insect cells demonstrating that CTHS-GFP fusions are not cleaved in insect cells (lanes 4 and 8). High Five cells infected with baculovirus carrying CHS-GFP were harvested 72 hours post-infection. Total cell extracts were prepared by boiling the cells in SDS-PAGE buffer and briefly sonicating the sample to reduce viscosity. 20 μg of the total proteins were resolved on 15% SDS-PAGE minigel. Extracts from yeast cells (lanes 1-3 and 5-7, same as in FIG. 6A) were used as standards. Western blot was performed with anti-GFP (lanes 1-4) or anti-SUMO antibodies and a secondary HRP-conjugated antibody. GFP alone (lanes 1 and 4), CTHS-GFP (lanes 2, 4, 6 and 8), and SUMO-proline-GFP (3 and 7) were loaded. Migration positions for each protein are indicated.

FIG. 6 shows a representative blot of GFP-fusions produced by yeast when expression is performed in YPD nutrient rich medium. There was a 10-20 fold increase in expression of GFP following fusion with CTHS. However, a nearly 50-fold increase in GFP production has been observed when cells were induced with 100 µM copper sulfate in synthetic medium. This variation in fold-increase is likely due to chelation of Cu ions by various compounds present in rich medium and decreased $Cu^{2+}$ availability for CUP promoter induction.

The data in FIG. 6 demonstrate unambiguously that SUMO-Pro-GFP and CTHS-GFP fusions were not cleaved whereas SUMO-Met-GFP was efficiently cleaved in yeast. The proteins migrate at expected rate on SDS-PAGE and, noticeably, no partial cleavage is detected.

Thus, the foregoing example provides evidence showing that: (a) CTHS can enhance the expression of GFP, and (b) CTHS-GFP can be produced as an uncleaved fusion in yeast. Production of the fusions in eukaryotes as uncleaved entities offers tremendous advantages such as: (1) an attached affinity or epitope tag would remain attached to the expressed protein of interest, (2) such tags can be removed by a SUMO protease (see EXAMPLE III), and (3) certain proteins produced in *E. coli* are not active owing to absence of posttranslational modifications that can only be introduced in eukaryotes, and not bacteria.

EXAMPLE III

Reconstitution of Cleavable Structure on the CTHS-fusion in Vitro and Cleavage by Ulp1

The molecular basis underlying the reconstitution of cleavable structure is outlined in FIGS. 3 and 4. A protein purified as a fusion with CTHS when mixed with NTHS can assemble into SUMO-like structure. In the next step this SUMO-like structure is recognized by a specific hydrolase which cleaves and releases the protein of interest, optionally with a new amino-terminus as described hereinabove. The following characteristics, among others, demonstrate the superiority of the instant invention:

1) Unlike fusions with full-length SUMO or other full-length Ubls, CTHS-fusion proteins are not cleaved in either prokaryotic or eukaryotic cells (demonstrated in EXAMPLE II).

2) CTHS-fusion and NTHS can assemble in vitro into a structure that is recognized and cleaved by specific hydrolase (see experiments below and FIGS. 7-9).

3) SUMO hydrolases are highly specific and extremely durable enzymes that are exceptionally well suited for in vitro bioprocessing applications.

Figure 7A:
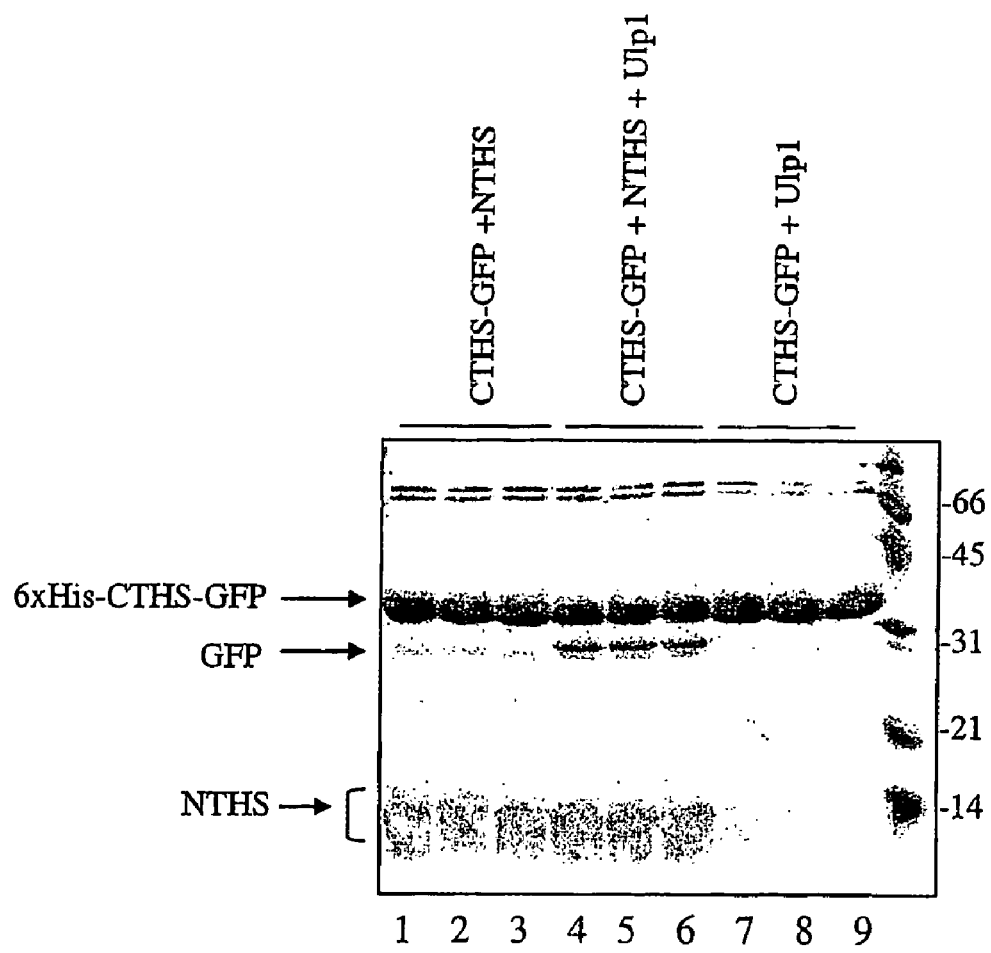
FIG. 7A is a Coomassie stained gel of 6×His-CTHS-GFP fusion protein purified from E. coli that was incubated with purified 6×His-NTHS (lanes 1-3), purified 6×His-NTHS and SUMO hydrolase Ulp1(lanes 4-6), or SUMO hydrolase Ulp1 (lanes 7-9). Reaction products were resolved on SDS-PAGE and stained with Coomassie. Molecular mass standards are shown on the right. Notably, release of free GFP can be observed only when all the components are present in the reaction mix.
Figure 7B:
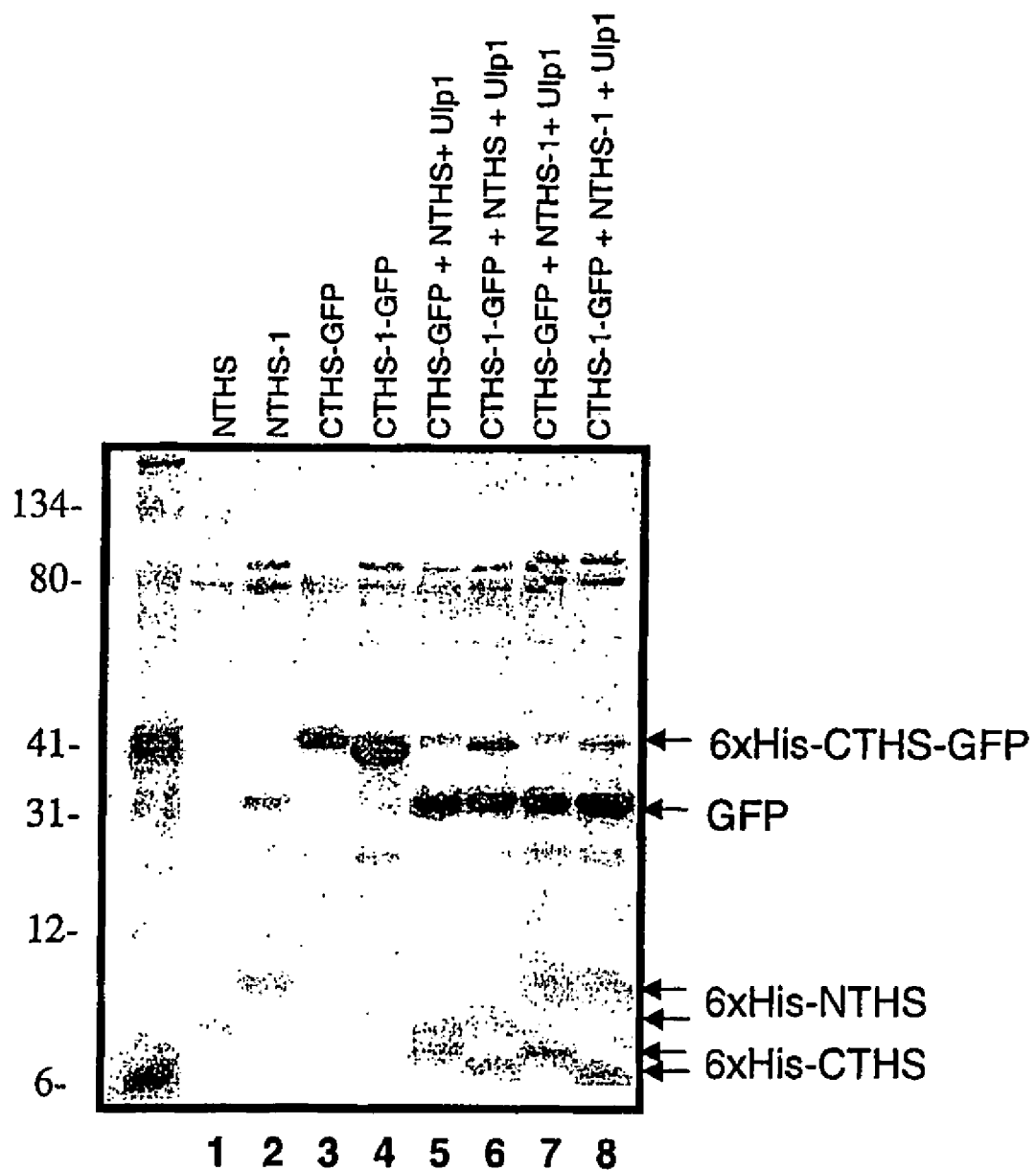
FIG. 7B is a Coomassie stained gel of 6×His-CTHS-GFP (lanes 3, 5, 7) and 6×His-CTHS-1-GFP (lanes 4, 6, 8) fusion proteins purified from E. coli that were incubated with SUMO hydrolase Ulp1 (lanes 5-8) and purified 6×His-NTHS (lanes 5-6) or 6×His-NTHS-1 (lanes 7-8). Reaction products were resolved on SDS-PAGE and stained with Coomassie. Lanes 1 and 2 are controls of purified 6×HisNTHS and 6×His-NTHS-1. Molecular mass standards are shown on the left. Notably, release of free GFP can be observed when any combination of CTHS and NTHS is used. Identification of the protein bands is at the right of the gel.

FIG. 7A depicts the experimental results obtained when combining NTHS and CTHS-GFP in solution, resulting in assembly and formation of a cleavable complex. 6×His-CTHS-GFP fusion protein purified from *E. coli* was incubated with SUMO hydrolase Ulp1 and 6×His-NTHS (lanes 4-6), with 6×His-NTHS (lanes 1-3) or Ulp1 (lanes 7-9). Release of free GFP can be observed only when all the components are present in the reaction mix. FIG. 7B demonstrates that the boundaries of NTHS and CTHS are not fixed and the functional elements of the system (e.g. CTHS and NTHS) may be changed without detectable effect on cleavage performance. Furthermore, purification tags such as, but not limited to 6×His, GST, MBP, a sequence facilitating covalent coupling to solid support such as Cys residue, may be attached to either the amino- and/or carboxy-termini of NTHS.

Figure 8:
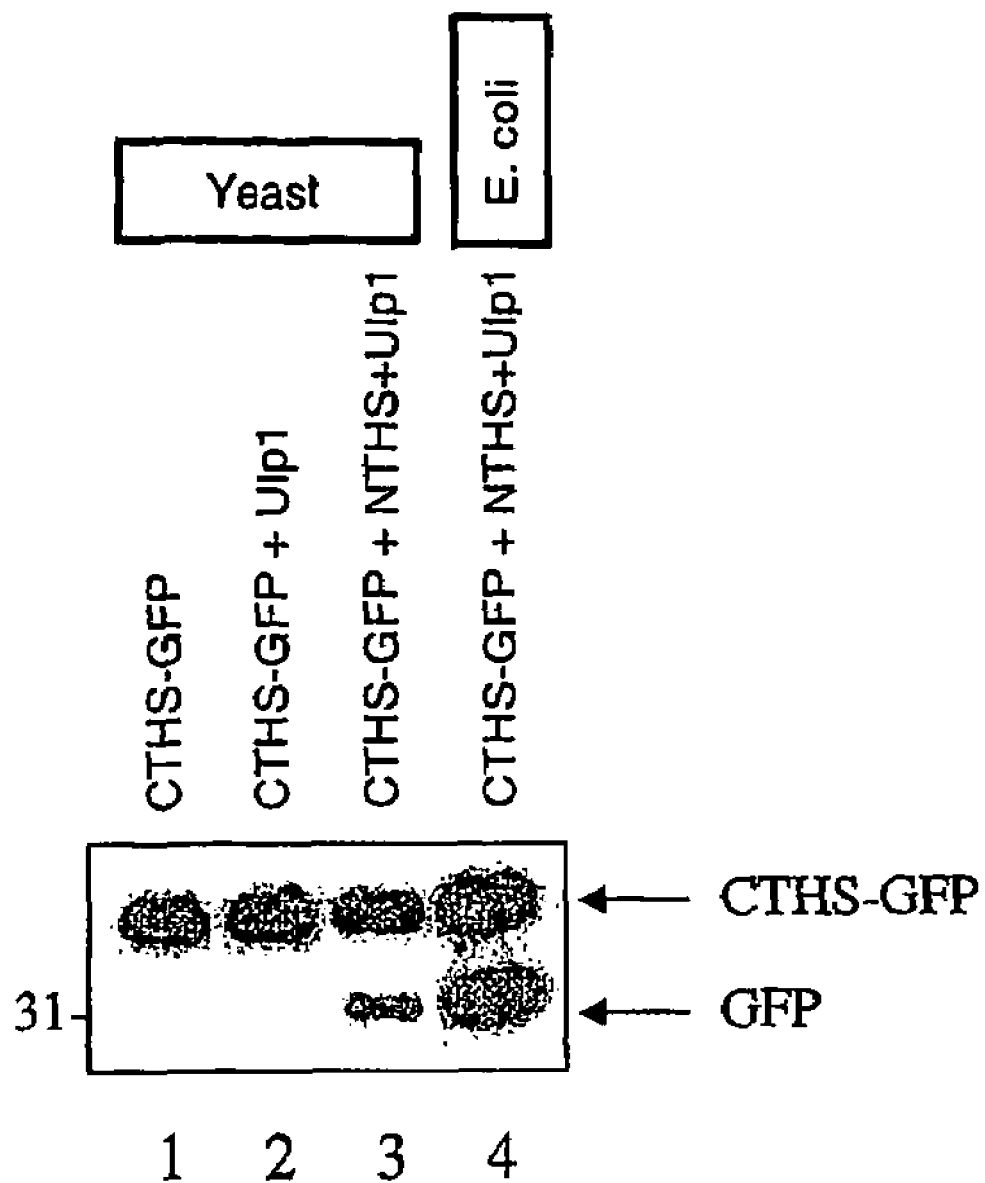
FIG. 8 depicts a Western blot of 6×His-CTHS-GFP fusion protein that was partially purified from yeast cells and incubated alone (lane 1), with Ulp1 (lane 2), or with Ulp1 in the presence of NTHS (lane 3). Reaction products were resolved on SDS-PAGE transferred onto nitrocellulose and probed with anti-GFP antibodies. Lane 4 depicts the results from a reaction similar to lane 3 wherein the 6×His-CTHS-GFP was purified from E. coli.

The experiment depicted in FIG. 8 demonstrates that the fusion proteins are not cleaved in yeast. 6×His-CTHS-GFP fusion was partially purified from yeast cells transformed with YEp-6×His-CTHS-GFP (same as FIG. 6, lane 3). The protein was incubated with Ulp1 alone or with Ulp1 in the presence of NTHS. Once again the release of free GFP can be observed only when all the components are present in the reaction mix.

Figure 9:
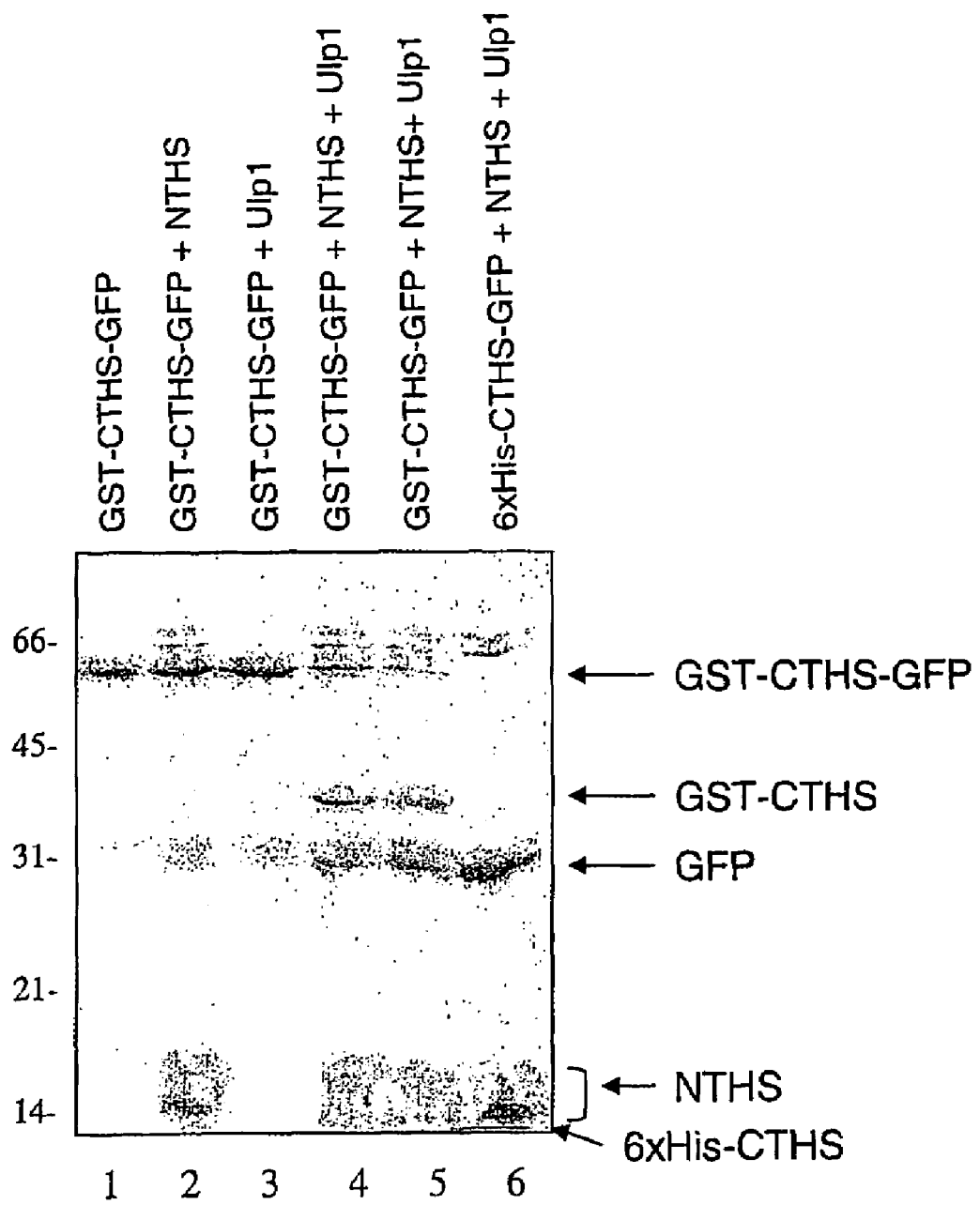
FIG. 9 is a Coomassie stained gel of purified GST-CTHS-GFP fusion proteins incubated alone (lane 1), with purified 6×His-NTHS (lane 2), with Ulp1 (lane 3), or with purified 6×His-NTHS and SUMO hydrolase Ulp1 (lanes 4 and 5). Lane 6 shows similar reaction as in lanes 4 and 5, but with purified 6×His-CTHS-GFP. Reaction products were resolved on SDS-PAGE and stained with Coomassie. Positions of molecular mass standards are indicated on the left. Identification of the protein bands is at the right of the gel.

The experiment in FIG. 9 demonstrates that the technology is adaptable to other fusions. Namely, CTHS-GFP can carry a large affinity tag such as GST (glutathione transferase) to be used for the production and purification of the fusion proteins. Purified GST-CTHS-GFP fusion protein was incubated with purified NTHS and SUMO hydrolase Ulp1 (lanes 4 and 5) or in the absence of one of the components (lanes 2 and 3). When all the components are present in the reaction mix free GFP can be efficiently released. Thus, there is no hindrance (e.g., steric hindrance) to the reconstitution of SUMO or cleavage by Ulp1 when a large tag, such as GST, is employed.

Thus the instant invention allows for the expression of a protein of interest in a eukaryotic cell and the subsequent purification of the protein of interest. Notably, certain proteins produced in *E. coli* are not active owing to absence of posttranslational modifications which only occur in eukaryotes.

EXAMPLE IV

Purification of CTHS-fusion Proteins by Affinity Chromatography on Immobilized NTHS C2

In addition to employing affinity tags such as, but not limited to 6×His, GST, MBP, FLAG™ and HA epitopes, fused to the amino-terminus of CTHS, the current invention provides yet another method of purifying CTHS. Specifically, CTHS can be purified by exploiting the natural affinity between CTHS and NTHS. Similarly, N-terminal domains of Ubls are expected to possess an affinity for the C-terminal domains of respective Ubls. NTHS (or N-terminal domains of other ub-like proteins) can be attached (covalently or noncovalently) to a solid support such as a chromatographic support. Additionally, a sequence facilitating covalent coupling to a solid support, such as a Cys residue or purification tag, may be attached to either the amino- or carboxy-terminus of NTHS. Bringing a solution (e.g., cell lysate) that contains a CTHS-protein of interest (also referred to as a passenger protein) fusion protein in contact with a solid support containing immobilized NTHS will allow affinity purification of the CTHS-protein of interest fusion protein. Following purification, the protein of interest is efficiently and faithfully cleaved from the junction by specific proteases.

Figure 10:
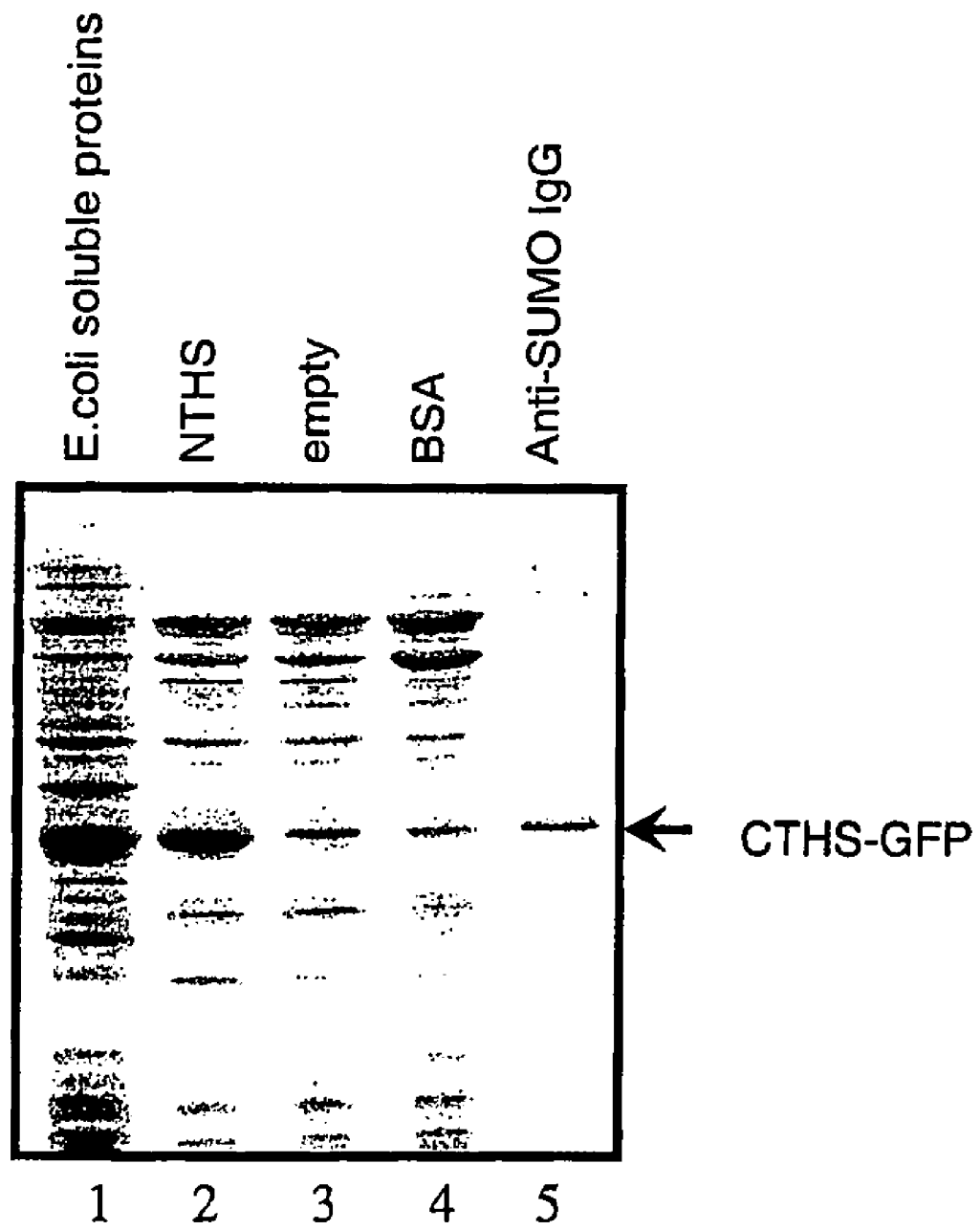
FIG. 10 is a Coomasssie stained gel depicting the purification of CTHS-GFP on immobilized NTHS or anti-SUMO IgGs. Total soluble proteins (1 mg) from E. coli expressing 6×His-CTHS-GFP fusion were incubated with 15 μl (bed volume) of resins onto which specific proteins were covalently coupled. Samples were washed and resolved on 12% SDS-PAGE and stained with Coomassie. Molecular mass standards are shown on the right. The location of CTHS-GFP is indicated at the right.
Figure 11:
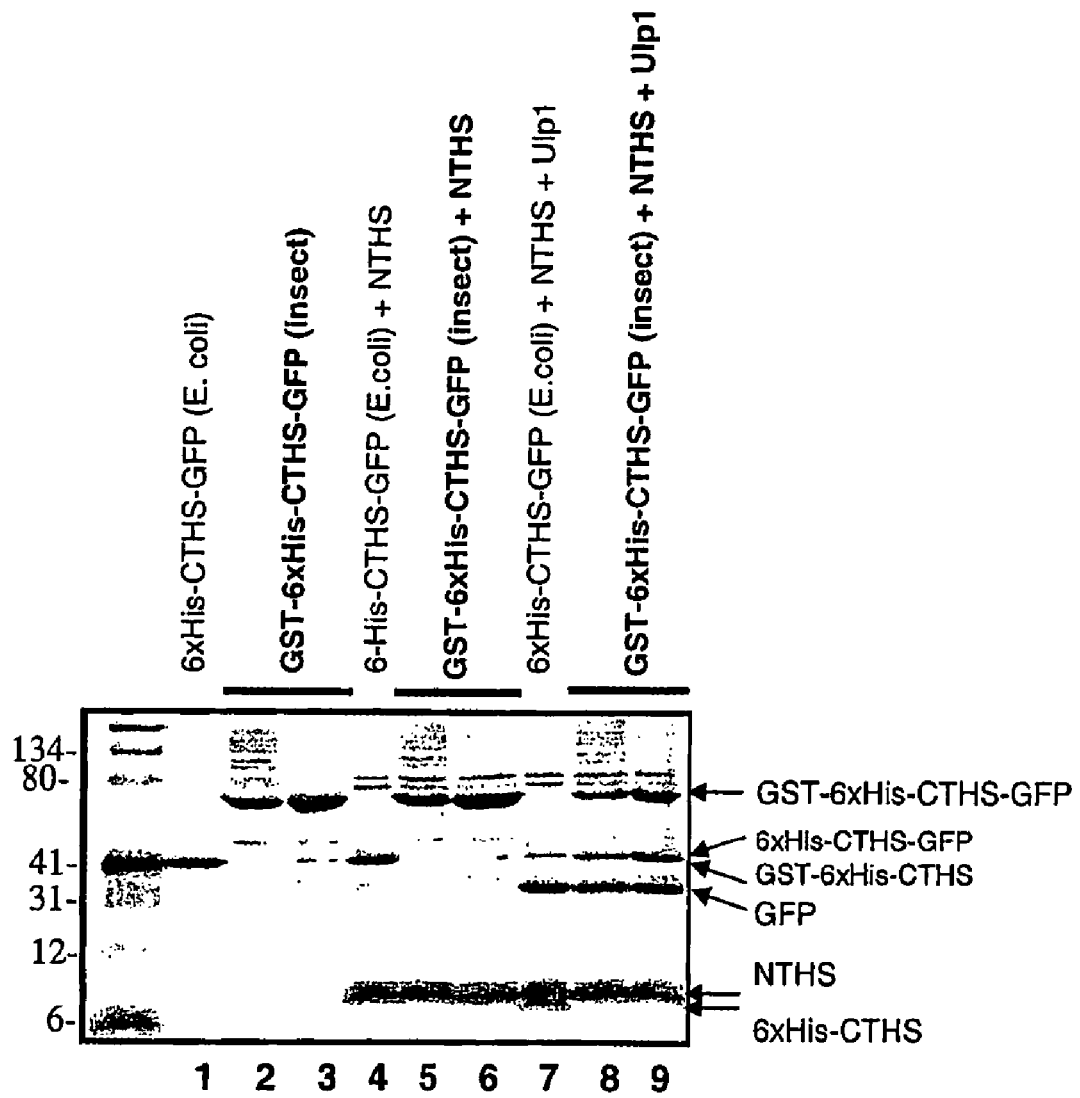
FIG. 11 is a Coomassie stained gel of GST-6×His-CTHS-GFP fusion protein purified from insect cells that was incubated alone (lanes 2-3), with purified 6×His-NTHS (lanes 5-6), or purified 6×His-NTHS and SUMO hydrolase Ulp1 (lanes 8-9). Reaction products were resolved on SDS-PAGE and stained with Coomassie. Molecular mass standards are shown on the left. Notably, release of free GFP can be observed only when all the components are present in the reaction mix. Control reactions with CTHS-GFP purified from E. coli are present in lanes 4 and 7. Identification of the protein bands is at the right of the gel.

The data presented in FIG. 10 provides experimental evidence for the feasibility of affinity purification of CTHS fusions on immobilized NTHS. Total soluble proteins (1 mg) from *E. coli* expressing the 6×His-CTHS-GFP fusion protein were incubated with 15 µl (bed volume) of resins onto which specific proteins were covalently coupled. The resins were generated as follows. NTHS was cloned with an engineered cysteine residue at the N-terminus (Cys-6×His-NTHS). Cys-6×His-NTHS was expressed, purified, and coupled to Sulfolink resin (Pierce; Rockford, Ill.). Similarly treated and blocked resin (empty resin) was obtained by omitting the Cys-6×His-NTHS from the coupling reaction. Reduced BSA (lane 4) was coupled in the same manner as Cys-6×His-NTHS. The IgG-immobilized resin was generated as follows. The total rabbit IgG fraction was purified from the sera of rabbits immunized with SUMO (Rockland immunochemicals; Gilbertsville, Pa.). IgGs were then coupled to Glyoxal-activated beads (Active Motif; Carlsbad, Calif.).

After a 1 hour incubation of the proteins with resin with constant mixing at room temperature, the resins were sedimented by mild centrifugation and washed 4 times with increasing concentrations of PBS. Washed resins were mixed with 30 µl of SDS-PAGE sample buffer and boiled for 2 minutes. 10 µl of each sample were resolved by 12% SDS-PAGE and stained with Coomassie. The significant presence of CTHS-GFP on the resin to which NTHS was immobilized, suggests a specific interaction between CTHS and NTHS and an approach for purification of CTHS fusions.

Importantly, the purification of CTHS-fusion proteins on immobilized NTHS will yield reconstituted cleavable SUMO structure. Such structures, however, can be reliably protected from cleavage by SUMO proteases naturally present in eukaryotic cells by addition of low concentrations (~2 mM) of inexpensive inhibitors. Examples of such inhibitors include, without limitation, salts of zinc, cobalt and other metals. After purification of CTHS fusion proteins, these inhibitors are efficiently chelated by EDTA to allow the cleavage to proceed.

FIG. 10 also demonstrates that IgGs produced against SUMO can also be used as an affinity matrix when coupled to a solid support. CTHS fusions purified in this manner may be contacted with NTHS to generate reconstituted SUMO for cleavage and release of the protein of interest.

EXAMPLE V

Modification of Amino Acid Sequences of NTHS and CTHS for Increased Affinity and Enhanced Purification Efficiency The affinity between NTHS and CTHS can further be enhanced by introducing mutations into the sequences of NTHS, CTHS or both. A variety of mutations can be contemplated through a rational approach as the detailed 3D structures of SUMO, Ub, Rub1 and other Ubls are available. Directed mutagenesis may enhance the interactions between CTHS and NTHS due, for example, to the introduction of amino acids with higher hydrophobicity. For example, $Lys^{41}$ (located in $KIKK^{41}TTPL$ (SEQ ID NO: 87) context of NTHS), which appears to be in close vicinity of $Leu^{81}$ (located in $EDL^{81}DME$ (SEQ IS NO: 88) context of CTHS) may be replaced with a hydrophobic amino acid such as methionine. Such a substitution most likely will not affect the other properties of NTHS, such as the ability to serve as a substrate for Ulp1 when a part of reconstitutes SUMO, because the same positions in human SUMO-1 is occupied by methionine.

Alternatively, charged residues may be introduced in CTHS and NTHS. For example, $Ile^{88}$ (located in $DNDI^{88}EAH$ (SEQ ID NO: 89) context of CTHS), which appears to be in a close vicinity of $Lys^{27}$ (located in $INLK^{27}VSD$ (SEQ ID NO: 90) context of NTHS) may be replaced with a negatively charged amino acid such as $Glu^{88}$.

In addition to directed mutagenesis, random mutagenesis of CTHS or NTHS can be performed and the mutant molecules can be screened for binding affinities and those that show stronger affinities can be selected and used for expression and affinity purification.

Another method to increase the affinity between NTHS and CTHS consists of the addition of new amino acids at the C-terminus of NTHS and at the N-terminus of CTHS (indicated as the "boundary" in FIG. 3). For example, the addition of several positively charged amino acid residues (e.g. Lys or Arg) to the C-terminus of NTHS and the simultaneous addition of several negatively charged amino acid residues (e.g. Glu or Asp) to the N-terminus of CTHS, will result in the formation of multiple salt bridges between the oppositely charged amino acid residues and will stabilize the interaction between CTHS and NTHS. Other structures, peptides, or proteins known to interact strongly such as, but not limited to, anti-parallel β-sheets, anti-parallel α-helices (e.g. leucine zippers or coiled coils), and proteins that from dimers may also be used as an alternative to charged amino acids.

Another aspect of the instant invention involves the use of CTHS as an affinity tag to identify a small molecule that tightly binds the exposed surface on CTHS that normally interacts with NTHS (NTHS interacting CTHS surface). Identification of such a molecule may be conducted through computer based screening of atomic coordinates of library of chemical compounds versus the predicted atomic coordinates of NTHS interacting CTHS surface (in silico). Alternatively, CTHS and SUMO may be screened against the libraries of compounds immobilized on chromatographic supports (peptidomimetic approach). Identification of the candidate small molecules that selectively bind CTHS and not SUMO will indicate an interaction of the compound with NTHS interacting CTHS surface. Identified compounds may then be used to selectively purify CTHS fusion proteins but not SUMOylated proteins and free SUMO that are naturally present in eukaryotes. Chemicals identified by either in silico or conventional approaches may further be modified to provide new structures suitable for use as affinity ligand for chromatographic separations.

EXAMPLE VI

Figure 4A:
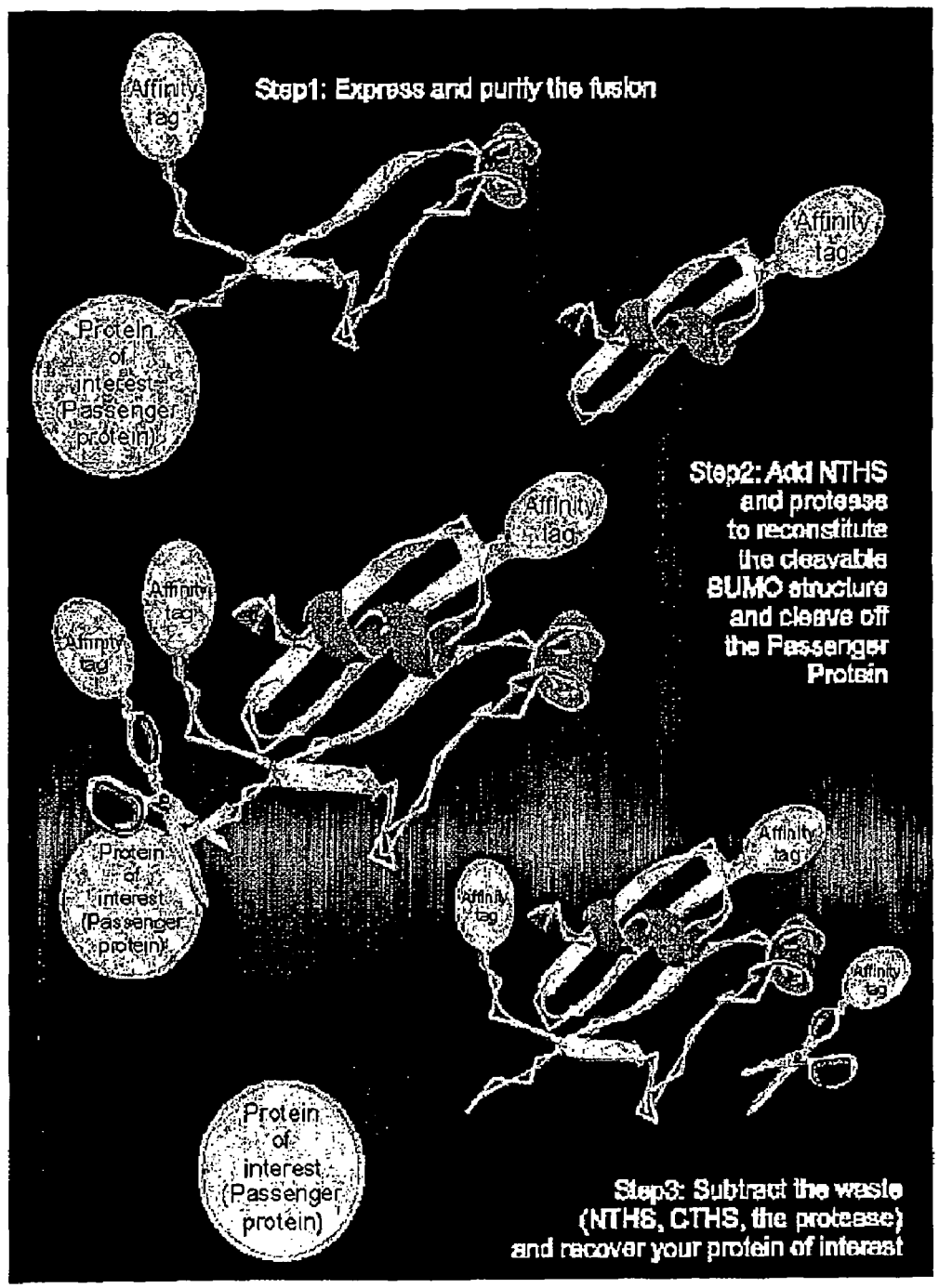
FIG. 4A is a schematic representation of the steps involved in a particular purification scheme using conventional affinity tags and matrices.
Figure 4B:
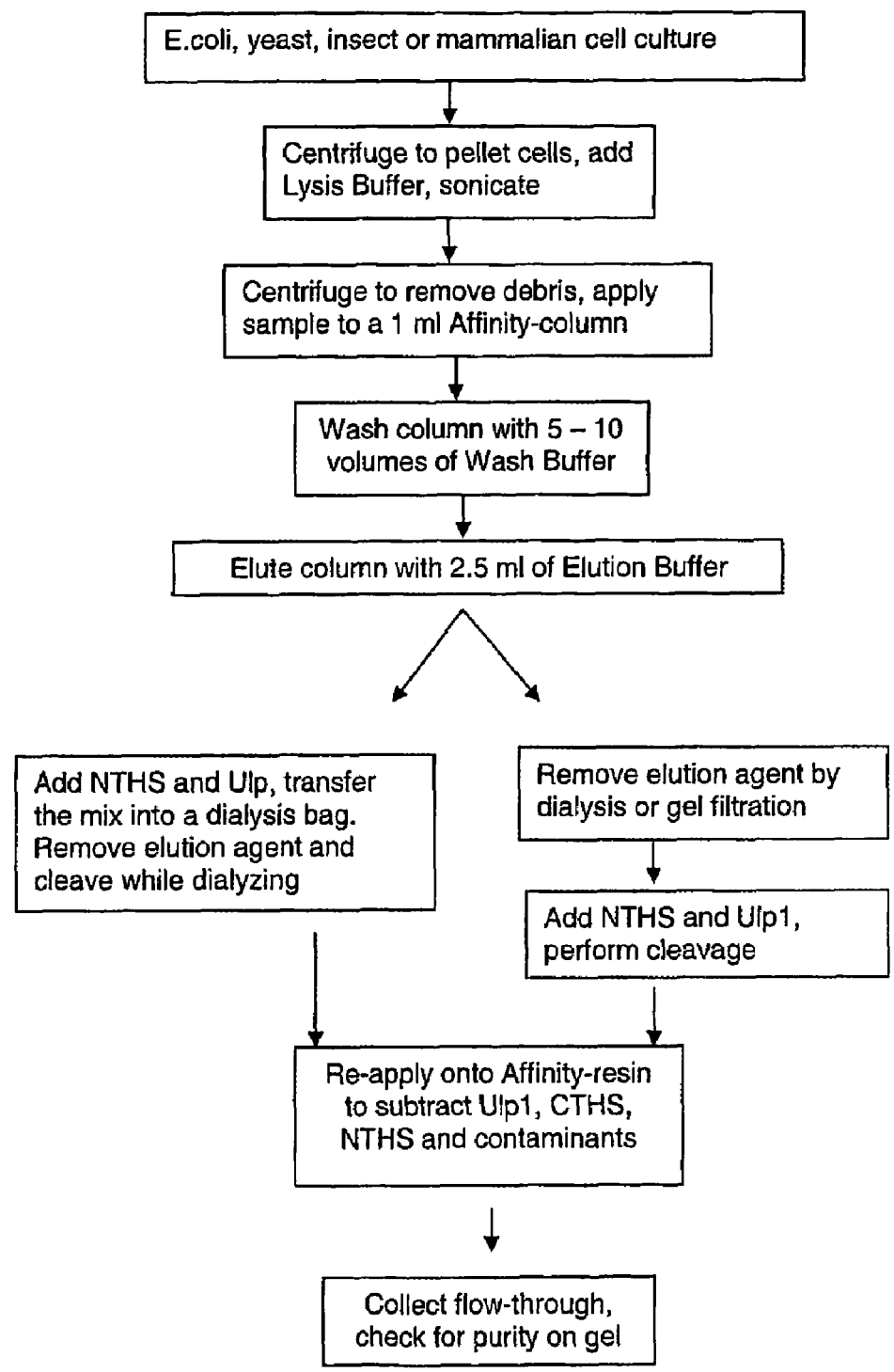
FIG. 4B is a flow chart of the purification scheme. Briefly, the cleavable SUMO structure is reconstituted by complementing the purified CTHS fusion protein with purified NTHS. Upon reconstitution, the NTHS-CTHS structure becomes cleavable by Ulp1 protease and the protein of interest is released. Removal of the CTHS, NTHS and the protease is accomplished by chromatography on the appropriate affinity matrix. Examples of affinity tags include, without limitation, GST, 6×His, MBP and HA epitope. See Example VI for a more detailed explanation of the presented purification schemes.

Conventional Affinity Purification of CTHS Fusion Proteins and Cleavage with SUMO Hydrolase FIGS. 4A and 4B present a diagram and flow chart that depict certain embodiments of the purification and cleavage of CTHS fusion proteins. This example explains these embodiments in more detail. The following tables list the solutions that can be used for the affinity purification of CTHS fusions that carry various affinity tags and their subsequent cleavage.

TABLE 3

| Solution | Components |
| --- | --- |
| Solutions for purification of 6xHis-CTHS fusions | |
| Lysis buffer | 25 mM Tris pH 8.0; 50 mM NaCl |
| Column loading buffer, Dialysis or Gel filtration buffers | 25 mM Tris pH 8.0; 250 mM NaCl; 10 mM imidazole |
| Wash Buffer | 25 mM imidazole; 50 mM Tris pH 8.0; 250 mM NaCl; (optional) 5-10 mM β-mercaptoethanol (protein dependent) |
| Elution Buffer | 300 mM imidazole; 50 mM Tris pH 8.0; 250 mM NaCl; (optional) 5-10 mM β-mercaptoethanol (protein dependent) |
| Solutions for purification of GST-CTHS fusions | |
| Lysis buffer | 25 mM Tris pH 8.0; 50 mM NaCl |
| Column loading buffer Dialysis or Gel filtration buffers | 25 mM Tris pH 8.0; 250 mM NaCl; |
| Wash Buffer | 50 mM Tris pH 8.0; 250 mM NaCl; (optional) 5-10 mM β-mercaptoethanol (protein dependent) |
| Elution Buffer | 50 mM glutathion (reduced); 50 mM Tris pH 8.0; 250 mM NaCl; (optional) 5-10 mM β-mercaptoethanol (protein dependent) |

From typical 250 ml cultures, the samples are pelleted by centrifugation, and supernatants are removed by decanting. Generally, from 250 ml of culture, 1.0-1.5 grams of wet cells are produced. Pelleted cells are then resuspended in 5-10 ml of lysis buffer. Samples are kept on ice throughout the sonication procedure. Using an appropriate tip, the samples are sonicated 3-5 times (10 second pulses) at 50% duty cycle. Sonicated samples may be adjusted to 1% Triton X-100 and incubated at 4° C. for 30 minutes to allow better recovery of CTHS fusion. Lysed samples (in lysis solution) are loaded onto 1-ml columns. The columns are washed with 5 to 10 volumes of wash buffer. Columns are developed with 2.5 ml of elution buffer.

A typical yield from a 1 ml column is 5 mg of fusion protein. Two examples of methods by which SUMO hydrolase cleavage may be performed are: 1) performing cleavage in a dialysis bag with 5 mg of NTHS (equimolar concentration to the expected yield of protein) and 500 units of SUMO protease added, and incubating overnight at 4° C.; and 2) removing the elution agent by dialysis or desalting (gel filtration), and subsequently adding 5 mg of NTHS and 500 units of SUMO protease to the sample, and incubating at room temperature for 2 hr or at 4° C. overnight. Cleavage may be monitored by gel electrophoresis. The reaction products from the above cleavage methods are loaded onto a column packed with an appropriate affinity resin. The protein of interest is recovered in the flow through, free of NTHS, CTHS and Ulp1. As described hereinabove, the cleavage reaction may also be performed directly on the column. A unit of SUMO protease (Ulp1) is defined as the amount of enzyme that cleaves 15 μg of pure SUMO-Met-GFP (up to 95%) in 50 mM Tris-HCl pH 8.0, 0.5 mM DTT, 150 mM NaCl at room temperature in 60 minutes.

After cleavage, protein of interest can be stored, directly used in intended applications, or subjected to additional purification steps. Removal of elution agent (by dialysis or desalting) and passing the sample through the resin that initially was used for purification of the CTHS fusion will trap most of the contaminating proteins resulting in 95% purity of the protein of interest.

The methods described here and shown in FIG. 4 primarily intend the use of identical affinity tags on all three protein components (e.g. tag-NTHS, tag-CTHS-PassengerProtein, tag-Ulp1). However, depending on the application, the tags may not necessarily be identical and all three components need not have a tag. Furthermore, two or more tags may be combined on the same protein (see for example, GST-6xHis-CTHS-GFP, presented in FIG. 9). Use of two tags may be beneficial in accelerated purification protocols in the following way: (1) After purification of GST-6xHis-CTHS-GFP on GSH resin and elution with GSH; (2) the fusion is brought in contact with 6xHis-NTHS and 6xHis-Ulp1 and incubated to allow cleavage; (3) the mix is directly applied onto Ni-resin column to subtract GST-6xHis, 6xHis-NHTS and 6xHis-Ulp1; and (4) GFP or the protein of interest is recovered in the flow through. Optionally, the GST-6xHis-CTHS-GFP construct may not contain the 6xHis tag and be retained on the Ni resin by its affinity for 6xHis-NTHS. These methods preclude the necessity to remove eluting agent prior to the subtraction step.

EXAMPLE VII

Adaptation of Other Ubiquitin-like Proteins (Ubls) for Use with the Described Technology The examples presented above demonstrate usefulness of partial SUMO sequences (CTHS and NTHS) for expression, purification and release of the protein of interest. In principle, any Ubl including ubiquitin (for examples see Table 1 and FIG. 1) may be utilized in a similar fashion. This example describes how other Ubl halves or domains may be generated and used in similar applications. FIG. 3 shows a 3-D structure of SUMO and the approximate position of the boundary between NTHS and CTHS. FIGS. 14, 15 and 25 give exact boundary positions and the sequences of two versions of CTHS and NTHS. The boundary between CTHS and NTHS was either introduced as in FIG. 14 or as in FIG. 25. It is important to note that when version 1 and version 2 of CTHS and NTHS were matched, the efficient cleavage was still achieved (see FIG. 7B). FIG. 26 gives examples of N-terminal domains (NTDs) and carboxy-terminal domains (CTDs) for each Ubl listed in Table 1. Two versions for each NTD and CTD are given. NTDs and CTDs for other Ubls (i.e. not listed in FIG. 26) can be deduced and utilized as follows. (1) The amino-acid sequence of the Ubl is aligned with the amino-acid sequences of SUMO (FIG. 14 or 25) or other Ubls (FIG. 26) either manually or using specialized software (e.g., pair-wise alignment at www.ncbi.nlm.nih.gov/BLAST). It is sufficient to perform the alignment with just one other Ubl which is known to be closely related (e.g. Rub1 may be aligned with Nedd8); (2) The boundaries are determined with respect to the examples given in FIG. 26; (3) Respective coding DNA sequences are deduced from the sequence of the gene; (4) Cloning of the sequences encoding CTD and NTD is performed by standard methods as described above; (5) CTD is operably linked to the coding sequence of the protein of interest as described above; (6) proteins are expressed and purified as above; and (7) reconstitution of cleavable structure and cleavage by a specific hydrolase (e.g. DEN-1 if CTD and NTD of Rub1 is used; see FIG. 1) as described above.

EXAMPLE VIII

Adaptation of Other Ubiquitin Fold Proteins (Ubfs) for Use with the Described Technology Example VII provides information on how partial sequences of any Ubl, including SUMO and ubiquitin (for examples see Table 1 and FIG. 1), may be utilized for expression, purification and cleavage of proteins of interest. It is important to emphasize that structurally Ubls are not unique but have easily traceable structural similarities to some other proteins which may not be evolutionary or functionally related and may have minimal or no sequence similarity (44). These proteins may be classified as having a Ubiquitin fold (also referred to as beta-Grasp fold or beta-Grasp domain) (24, 54-59). Examples of Ubiquitin fold proteins (Ubfs) are provided in Table 4 (see also references 54-59). The structural feature that separates these proteins from others and places them in a specific class is a sequence of β-sheets and an α-helix (β-β-α-β-β) in the molecule that folds into a structure with specific positioning of the β-sheets in the order 2143 (25). Interestingly, the first two β-sheets (2 and 1) are anti-parallel as well as the two last ones (4 and 3), whereas the first and the last ones (1 and 4) are parallel. This arrangement may be referred to as β2, antiparallel-β1, parallel-β4, antiparallel-β3. Slight variations to the ubiquitin fold can be observed. The lengths of structural determinants (β-sheets and α-helix) and connecting loops may be different. Some proteins may contain additional β-sheets or α-helices (e.g., Ubls possess an extra strand in the β-sheet and a very short helix in the loop), yet the overall fold (β2, antiparallel-β1, parallel-β4, antiparallel-β3) is easily and unambiguously recognized. Yearly updates on Ubf family are found at the SCOP database (Structural Classification of Proteins) at the following URL (scop-.mrc-lmb.cam.ac.ukscop/data/scop.b.e.bi.html).

A careful analysis of the body of literature available on proteins that contain ubiquitin fold beta-Grasp domain) as part of their sequence reveals that all of the domains are easily produced as recombinant proteins. Furthermore, some data demonstrate that these domains serve as natural chaperones that stabilize a large protein that contains such beta-Grasp domain. It is therefore our conclusion that beta-Grasp fold, either in its entirety or as a part thereof (e.g. CTHS), may be successfully used as a fusion partner for enhancement of expression, stability and solubility of C-terminally fused recombinant proteins. Importantly, all the methods described hereinabove can be directly used with any of the Ubfs. Additionally, the NTD of any Ubf may be expressed and immobilized on solid support and further used as an affinity matrix for purification of CTD fused with the protein of interest.

Methods are provided herein for employing Ubfs as tags that enhance expression, stability and solubility of the fused proteins and that NTD of said Ubf as a part of an affinity matrix for purification of the fusion of CTD of said Ubf with the protein of interest. FIG. 3 shows a 3-D structure of SUMO and the approximate position of the boundary between NTHS and CTHS. FIGS. 14, 15 and 25 give exact boundary positions and the sequences of two versions of CTHS and NTHS. The boundary between CTHS and NTHS was either introduced as in FIG. 14 or as in FIG. 25. FIG. 26 gives examples of NTDs and CTDs for each Ubl listed in Table 1. FIG. 27 gives examples of NTDs and CTDs for some Ufds listed in Table 4. Two versions for each NTD and CTD are given. NTDs and CTDs for other Ufds (i.e., not listed in FIG. 27) can be deduced and utilized as follows. (1) The amino-acid sequence of the Ufd (ubiquitin fold domain) is aligned with amino-acid sequences of a homologous Ufd found in FIG. 27 either manually or using specialized software (e.g., pairwise alignment at www.ncbi.nlm.nih.gov/BLAST). It is sufficient to perform the alignment with just one other Ufd that is known to be closely related (e.g. CIDA may be aligned with CPAN); (2) The boundaries are determined with respect to the examples given in FIG. 27; (3) Respective coding DNA sequences are deduced from the sequence of the gene; (4) Cloning of the sequences encoding CTD and NTD is performed by standard methods as described above; (5) CTD is operably linked to the coding sequence of the protein of interest as described above; (6) a recognition site for specific protease (e.g. multibasic cleavage site such as RvRR and recognition sequences of thrombin, Factor Xa, enterokinase, and Tev) may be engineered into the construct following the CTD and before the protease; (7) proteins are expressed and purified as above; and (8) cleavage is performed by the specific protease and the reaction products are purified as described hereinabove. Notably, because the cleavage site may be a movable entity in this aspect of the invention, the fusion protein may, alternatively, comprise the NTD, the cleavage site, and the protein of interest and be purified by immobilized CTD.

If, based on its solved secondary structure, a new protein or its part is classified as having a ubiquitin fold, then the boundaries of the sequence suitable for use as a fusion tag can be determined using the following criteria: (1) full length tag must contain the sequences coding for two β-sheets, an α-helix and two β-sheets (β2, antiparallel-β1, parallel-β4, antiparallel-β3); (2) NTD must contain two anti-parallel β-sheets and an α-helix (β-β-α-, however, the α-helix may not necessarily be full-length) with or without the loop that connects the α-helix with the following β-sheet; and (3) CTD must contain two antiparallel β-sheets, whether or not interrupted by an extra sheet and/or helix (however, the first β-sheet may not necessarily be full-length).

TABLE 4

Properties of Ubiquitin-fold Proteins (Ufds)

| Domain or domain class name | Function of Ubf domain | Function of the protein | Examples | Similarity to Ub | ACC Nos. |
| --- | --- | --- | --- | --- | --- |
| UDP, Ubx, UBQ, UBA, etc. | Interaction with proteasome, chaperone | Ubiquitin ligases, signal transduction | RAD23, Parkin, Dsk2 Fbx7 | 20-80% | NP_010877 XP_011437 NP_014003 |
| CAD and PB1 | Protein-protein interaction | Caspase activated DNAse, signaling | Bem1p, CPAN DEF-40, CIDE-B | None | AAC39709 1IP9_A |
| MoaD/ThiS | Sulfide transfer | Regulation of mitosis. | MoaD ThiS | None | NP_752796 |
| Tgs-like | unknown | Threonyl-tRNA synthetase | ThrRS | None | NP_288153 |
| Ferredoxin/ ferredoxin-like | Electron transport | Electron transport | Ferredoxin, Xanthine oxidase | None | NP_442127 NP_355267 |
| Staphylokinase/ Streptokinase | Unknown | Plasminogen activator | Staphylokinase | None | NP_375053 |
| Superantigen toxins | Unknown | Cell surface protein | Enterotoxin c2, superantigen Spe-C | None | NP_269186 |
| Immunoglobulin binding | Immunoglobulin binding | Cell surface protein, | Protein G | None | P06654 |
| IF3 | Ribosome binding | Translation initiation | Translation initiation factor IF3 | None | P03000 |
| Glutamine synthetase | unknown | Glutamine synthesis | Glutamine synthetase | None | NP_458042 |

EXAMPLE IX

Examples of Various Classes of Proteins Whose Fusion with Carboxy-Terminal Half of SUMO (CTHS) Will Improve Quantity and Quality of Proteins The design and construction of all the pET vectors expressing GPP has been described above. As with GFP, any DNA sequence can be cloned as a fusion with 6×His-CTHS. Furthermore, the 6×His-CTHS-protein of interest fusion protein can be recloned into any yeast (e.g., Yep), baculoviral (e.g., pFastBac), mammalian (e.g., pCDNA3) or other host vectors Table 5 provides representative molecules and GenBank Accession numbers for the expression of the proteins listed using the methods of the invention.

TABLE 5

Examples of Proteins and Protein Classes for use with current invention

| Protein class | Success rate with conventional systems | Protein | Requirement for specific N-terimini | Requirement for glycosylation | ACC# |
|---|---|---|---|---|---|
| Cytokine | High/inclusion bodies | IL-15 IFNγ | Yes | No | P40933 P01579 P01375 |
| Chemokine | High/inclusion bodies | Myb-1β | Yes | No | P13236 |
| Growth factors | low | TGFα | Yes | Varies | P01135 |
| Enzymes | Low | DNA polymerase | Yes | No | 1RDR |
|  | Very low | DNase II alpha | Yes | Yes | AAC77366 |
|  | Very low | Cathepsin (peptidase) | Unknown | Yes | P07858 |
|  | Very low | BMP-1 protease | Unknown | Yes | NP_001190 |
| Peptides including therapeutic | Low/proteolysis | Calcitonin | Yes | varies | CAA26189 |
| Nuclear receptors | high | LXR | No | varies | Q13133 |
| Cytokine/chemokine/growth factor receptors | Low/inclusion bodies | IFNAR, VEGFR, CCR9 | No | varies | P15260 P35968 NP_034043 P00533 |
| Ser-Thr kinases | Low | MAPK | No | No | P49137 |
| Tyr kinases | Extremely low/inactive | Zap 70 | No | No | P43403 |
| Transcription factors | low | CREB | Unknown | Yes | NP_005185 |
| Initiation factors | low | eIF2 | Unknown | Yes | NP_004085 |
| Viral/parasite/bacterial proteins (vaccines) | Low | Spike protein, Apa (Rv1860), RAP-1 | Varies | varies | AAP33697 Q50906 AAF15365 | by, for example, a simple cut-and-paste procedure identical or similar to the one described above. Cell propagation, protein expression, harvesting, lysis, and purification of fusion are performed described above or according to one of the established procedures described elsewhere. Cleavage of fusions and subtraction of NTHS and Ulp1 is performed as described, for example, in Example III. The system described in this application has several major advantages as compared to other systems currently in use. One or more of these advantages may create a precedent for preferred use of the system described here over other systems. Industrial needs for protein manufacturing may suggest that the following classes or groups of proteins may be exemplified as the ones most likely to benefit from use of the current invention. Some of the factors that may be considered when expression system is selected are (1) the success of expression of the protein in various systems, (2) requirement for specific N-terminus, and (3) requirement for glycosylation. Each of these factors can be successfully addressed by the system described herein: (1)CTHS enhances the production of proteins, (2) robust cleavage by Ulp1 allows generation of any amino-terminus, and (3) expression in insect or mammalian cells will allow introduction of necessary post-translational modifications.

EXAMPLE X

Use of Carboxy-Terminal Half of SUMO (CTHS) for Enhanced Secretion of the Proteins in *E. coli*, Yeast, Insect and Mammalian Cells The basic characteristics of CTHS (e.g. small size and compact structure), should allow the use of CTHS in combination with secretion signals. The design and construction of all the vectors described above may be employed to allow a suitable secretion signal to be operably linked to the N-terminus of CTHS and affinity tag (see Table 6).

TABLE 6

Examples of secretion signals and construct configurations

| Host | Secretion signal | Fusion configurations | Ref. |
|---|---|---|---|
| Bacterial *E. coli* | PelB | PelB-AffinityTag-CTHS-PassengerProtein PelB-CTHS-PassengerProtein (periplasmic localization and release) | (45) |

TABLE 6-continued

Examples of secretion signals and construct configurations

| Host | Secretion signal | Fusion configurations | Ref. |
|---|---|---|---|
| Bacterial Caulobacter crescentus | RsaA | RsaA-AffinityTag-CTHS-PassengerProtein<br>RsaA-CTHS-PassengerProtein (true secretion) | (46) |
| Yeast Saccharomyces cerevisiae | α-factor PHO | α-AffinityTag-CTHS-PassengerProtein<br>α-CTHS-PassengerProtein | (47) |
| Yeast Pichia pastoris | | α-AffinityTag-CTHS-PassengerProtein<br>α-CTHS-PassengerProtein | (48) |
| Yeast Saccharomyces pombe | | PHO-AffinityTag-CTHS-PassengerProtein<br>PHO-CTHS-PassengerProtein | (49) |
| Insect cells Sf9<br>Insect cells HY5<br>Insect cells Drosophila melanogaster | gp67 Hbm (honey bee mellitin) | gp67-AffinityTag-CTHS-PassengerProtein<br>gp67-CTHS-PassengerProtein<br>Hbm-AffinityTag-CTHS-PassengerProtein<br>Hbm-CTHS-PassengerProtein | (50)<br><br>(51) |
| Mammalian cells CHO<br>Mammalian cells 293 | IgK | IgK-AffinityTag-CTHS-PassengerProtein<br>IgK-CTHS-PassengerProtein | (52) |

*E. coli* can not efficiently express and secrete mid-size and large proteins and, therefore, is not a preferred organism. However, certain peptides can be efficiently expressed and secreted from *E. coli* in very large quantities (53) and it is possible that fusions with CTHS will further improve yield and quantity of the peptides. More frequently used systems for extracellular production of proteins in prokaryotes include *Bacillus brevis*, *Caulobacter crescentus* and several others. Other hosts (yeast, insect and mammalian cells) are also used to produce proteins extracellularly. The secretion involves endoplasmic reticulum mediated pathway that ensures that only properly folded proteins are secreted. Therefore, at least in some cases, extracellular production of proteins may me advantageous because (1) the starting material will contain less contaminated proteins and non-proteinacious substances and (2) most of the protein will be properly folded. Upon capturing, and, if needed, further purification, CTHS is conveniently cleaved by Ulp1 and subtracted using appropriate affinity support.

REFERENCES

1. Ryan, T. E. and S. D. Patterson, *Proteomics: drug target discovery on an industrial scale*. Trends Biotechnol, 2002. 20(12 Suppl): p. S45-51.
2. Weickert, M. J., et al., *Optimization of heterologous protein production in Escherichia coli*. Curr Opin Biotechnol, 1996. 7(5): p. 494-9.
3. Ecker, D. J., et al., *Increasing gene expression in yeast by fusion to ubiquitin*. J Biol Chem, 1989. 264(13): p. 7715-9.
4. Butt, T. R., et al.; *Ubiquitin fusion augments the yield of cloned gene products in Escherichia coli*. Proc Natl Acad Sci U S A, 1989. 86(8): p. 2540-4.
5. Kapust, R. B. and D. S. Waugh, *Eschlerichia coli maltose-binding protein is uncommonly effective at promoting the solubility of polypeptides to which it is fused* Protein Sci, 1999. 8(8): p.1668-74.
6. Ikonomou, L., Y. J. Schneider, and S. N. Agathos, *Insect cell culture for industrial production of recombinant proteins*. Appl Microbiol Biotechnol, 2003.
7. Jonasson, P., et al., *Genetic design for facilitated production and recovery of recombinant proteins in Escherichia coli*. Biotechnol Appl Biochem, 2002. 35(Pt 2): p. 91-105.
8. Georgiou, G. and P. Valax, *Isolating inclusion bodies from bacteria*. Methods Enzymol, 1999. 309: p. 48-58.
9. Waldo, G. S., et al., *Rapid protein-folding assay using green fluorescent protein*. Nat Biotechnol, 1999. 17(7): p. 691-5.
10. Jentsch, S. and G. Pyrowolakis, *Ubiquitin and its kin: how close are the family ties?* Trends Cell Biol, 2000. 10(8): p. 335-42. __00001785 __00001785.
11. Yeh, E. T., L. Gong, and T. Kamitani, *Ubiquitin-like proteins: new wines in new bottles*. Gene, 2000. 248(1-2): p. 1-14.
12. Larsen, C. N. and H. Wang, *The ubiquitin superfamily: members, features, and phylogenies*. J Proteome Res, 2002. 1(5): p. 411-9.
13. Muller, S., et al., *SUMO, ubiquitin's mysterious cousin*. Nat Rev Mol Cell Biol, 2001. 2(3): p. 202-10.
14. Kim, K. I., S. H. Baek, and C. H. Chung, *Versatile protein tag, SUMO: its enzymology and biological function*. J Cell Physiol, 2002. 191(3): p. 257-68.
15. Saitoh, H. and J. Hinchey, *Functional heterogeneity of small ubiquitin-related protein modifiers SUMO-1 versus SUMO-2/3*. J Biol Chem, 2000. 275(9): p. 6252-8.
16. Mossessova, E. and C. D. Lima, *Ulp1-SUMO crystal structure and genetic analysis reveal conserved interactions and a regulatory element essential for cell growth in yeast*. Mol Cell, 2000. 5(5): p. 865-76.
17. Bayer, P., et al., *Structure determination of the small ubiquitin-related modifier SUMO-1*. J Mol Biol, 1998. 280 (2): p. 275-86.
18. Kim, K. I., et al., *A new SUMO-1-specitfic protease, SUSP1, that is highly expressed in reproductive organs*. J Biol Chem, 2000. 275(19): p. 14102-6.
19. Goettsch, S. and P. Bayer, *Structural attributes in the conjugation of ubiquitin, SUMO and RUB to protein substrates*. Front Biosci, 2002. 7: p. a148-62.
20. Kretz-Remy, C. and R. M. Tanguay, *SUMO/sentrin: protein modifiers regulating important cellular functions*. Biochem Cell Biol, 1999. 77(4): p. 299-309.
21. Davis, G. D., et al., *New fusion protein systems designed to give soluble expression in Escherichia coli*. Biotechnol Bioeng, 1999. 65(4): p. 382-8.
22. Smith, D. B. and K. S. Johnson, *Single-step purification of polypeptides expressed in Escherichia coli as fusioins with glutathione S-transferase*. Gene, 1988. 67(1): p. 31-40.
23. di Guan, C., et al., *Vectors that facilitate the expression and purification of foreign peptides in Escherichia coli by fusion to maltose-binding protein*. Gene, 1988. 67(1): p. 21-30.
24. Lo Conte, L., et al., *SCOP: a structural classification of proteins database*. Nucleic Acids Res, 2000. 28(1): p. 257-9.
25. Buchberger, A., et al., *The UBX domain: a widespread ubiquitin-like module*. J Mol Biol, 2001. 307(1): p. 17-24.
26. Link, A.J., K. Robison, and G. M. Church, *Comparing the predicted and observed properties of proteins encoded in the genome of Escherichia coli K-12*. Electrophoresis, 1997. 18(8): p. 1259-313.

27. Varshavsky, A., *The N-end rule and regulation of apoptosis.* Nat Cell Biol, 2003. 5(5): p. 373-6.
28. Ben-Bassat, A., *Methods for removing N-terminal methionine from recombinant proteins.* Bioprocess Technol, 1991. 12: p. 147-59.
29. Li, S. J. and M. Hochstrasser, *A new protease required for cell-cycle progression in yeast.* Nature, 1999. 398(6724): p. 24-51.
30. Li, S. J. and M. Hochstrasser, *The yeast ULP2 (SMT4) gene encodes a novel protease specific for the ubiqutin-like Smt3 protein.* Mol Cell Biol, 2000. 20(7): p. 2367-77.
31. Suzuki, T., et al., *A new 30-kDa ubiquitin-related SUMO-1 hydrolase from bovine brain.* J Biol Chem, 1999. 274(44): p. 31131-4.
32. Gong, L., et al., *Differential regulation of sentritnized proteins by a novel sentrin-specific protease.* J Biol Chem, 2000. 275(5): p. 3355-9.
33. Polo, S., et al., *A single motif responisible for ubiquitin recognition and monoubiquitination in endocytic proteins.* Nature, 2002. 416(6879): p. 451-5.
34. Hershko, A. and A. Ciechanover, *The ubiquitin system.* Annu Rev Biochem, 1998. 67: p. 425-79.
35. Chung, C. H. and S. H. Baek, *Deubiquitinating enzymes: their diversity and emerging roles.* Biochem Biophys Res Commun, 1999. 266(3): p. 633-40.
36. Layfield, R., et al., *Chemically synthesized ubiquitin extension proteins detect distinct catalytic capacities of deubiquitinating enzymes.* Anal Biochem, 1999. 274(1): p. 40-9.
37. Malakhov, M. P., et al., *UBP43 (USP18) specifically removes ISG15 from conjugated proteins.* J Biol Chem, 2002. 277(12): p. 9976-81.
38. Hu, M., et al., *Crystal structure of a UBP-family deubiquitinating enzyme in isolation and in complex with ubiquitin aldehyde.* Cell, 2002. 111(7): p. 1041-54.
39. Johnson, E. S., et al., *The ubiquitin-like protein Smt3p is activated for conjugation to other proteins by an Aoslp/Uba2p heterodimer.* Embo J, 1997. 16(18): p.5509-19.
40. Terpe, K., *Overview of tag protein fusions: from molecular and biochemical fundamentals to commercial systems.* Appl Microbiol Biotechnol, 2003. 60(5): p. 523-33.
41. Lyttle, C. R., et al., *Human estrogen receptor regulation in a yeast mnodel system and studies on receptor agonists and antagonists.* J Steroid Biochem Mol Biol, 1992. 42(7): p. 677-85.
42. Sherman, F., G. Fink, and J. Hicks, *Methods in yeast genetics.* Cold Spring Harbor Laboratory, Cold Spring Harbor, N.Y. 1986.
43. Woods, R. A. and R. D. Gietz, *High-efficiency transformation of plasmid DNA into yeast.* Methods Mol Biol, 2001. 177: p. 85-97.
44. Orengo, C. A., D. T. Jones, and J. M. Thornton, *Protein superfamilies and domain superfolds.* Natures 1994. 372 (6507): p. 631-4.
45. Lin, Z., T. Thorsen, and F. H. Arnold, *Functional expression of horseradish peroxidase in E. coli by directed evolution.* Biotechnol Prog, 1999. 15(3): p. 467-71.
46. Bingle, W. H., J. F. Nomellini, and J. Smit, *Secretion of the Caulobacter crescentus S-layer protein: further localization of the C-terminal secretion signal and its use for secretion of recombinant proteins.* J Bacteriol, 2000. 182 (11): p. 3298-301.
47. Ngamkitidechakul, C. and S. S. Twining, *Buffered nonfermenter system for lab-scale production of secreted recombinant His-tagged proteins in Saccharomyces cerevisiae.* Biotechniques, 2002. 33(6): p. 1296-300.
48. Lawson, C., et al., *Purification and characterization of recombinant rat mast cell protease 7 expressed in Pichia pastoris.* Protein Expr Purif, 2002. 25(2): p. 256-62.
49. Elliott, S., et al., *Isolation and characterization of the structural gene for secreted acid phosphatase from Schizosaccharomyces pombe.* J Biol Chem, 1986. 261(6): p. 2936-41.
50. Rupp, B., et al., *High level expression of the IL-1 receptor related T1 receptor in insect cells.* Biochem Biophys Res Commun, 1995. 216(2): p. 595-601.
51. Tessier, D. C., et al., *Enhanced secretion from insect cells of a foreign protein fused to the honeybee melittin signal peptide.* Gene, 1991. 98(2): p. 177-83.
52. Coloma, M. J., et al., *Novel vectors for the expression of antibody molecules using variable regions generated by polymerase chain reactions* J Immunol Methods, 1992. 152(1): p. 89-104.
53. Ray, M. V., et al., *Production of salmon calcitonin by direct expression of a glycine-extended precursor in Escherichia coli.* Protein Expr Purif, 2002. 26(2): p. 249-59.
54. Sakata E. et al., *Parkin binds the Rpn10 subunit of 26S proteasomes through its ubiquitin-like domain.* EMBO Rep. 2003 March;4(3):301-6.
55. Lake et al., *Mechanism of ubiquitin activation revealed by the structure of a bacterial MoeB-MoaD complex.* Nature. 2001 Nov. 15;414(6861):325-9.
56. Terasawa et al., *Structure and ligand recognition of the PBI domain: a novel protein module binding to the PC motif.* EMBO J. 2001 Aug. 1;20(15):3947-56.
57. Zhou P, et al., *Solution structure of DFF40 and DFF45 N-terminal domain complex and mutual chaperone activity of DFF40 and DFF45.* Proc Natl Acad Sci U S A. 2001 May 22;98(11):6051-5.
58. Arcus V L, et al., *Conservation and variation in superantigen structure and activity highlighted by the three-dimensional structures of two new superantigens from Streptococcus pyogenes.* J Mol Biol. 2000 May 26;299(1):157-68.
59. Derrick J P and Wigley D B. *The third IgG-binding domain from streptococcal protein G. An analysis by X-ray crystallography of the structure alone and in a complex with Fab.* J Mol Biol. 1994 Nov. 11;243(5):906-18.
60. Kycia J H, et al. *Prokaryotic translation initiation factor IF3 is an elongated protein consisting of two crystallizable domains.* Biochemistry. 1995 May 9;34(18):6183-7.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for enhancing the expression a protein of interest in a host cell comprising:
   a) providing a nucleic acid construct which encodes a fusion protein wherein said construct consists of:
      i) a nucleic acid sequence encoding a carboxy-terminal domain of SUMO, wherein said carboxy-terminal domain of SUMO consists of the amino acid sequence from between position 50 and position 62 through position 98 of SEQ ID NO: 1;
      ii) a nucleic acid sequence encoding said protein of interest; and
      iii) a nucleic acid sequence encoding at least one purification tag;
      wherein said carboxy-terminal domain of SUMO is attached to the amino-terminus of said protein of interest in the expressed fusion protein, wherein said at least one purification tag is attached to the amino-terminus of said carboxy-terminal domain of SUMO in said expressed fusion protein, and wherein said fusion protein begins with a methionine;
   b) expressing said nucleic acid construct in said host cell, whereby the presence of said carboxy-terminal domain of SUMO in said fusion protein increases the expression level of said protein of interest in said host cell.

2. The method of claim 1, wherein said host cell is selected from the group consisting of a yeast cell, *E. coli*, a bacterial cell, a mammalian cell, and an insect cell.

3. The method of claim 1, wherein said nucleic acid construct encoding a fusion protein is in a vector.

4. The method as claimed in claim 1, wherein the fusion protein, when expressed, comprises the carboxy-terminal domain of SUMO attached to the amino-terminus of the protein of interest such that cleavage site of SUMO is immediately amino terminal to the protein of interest, said method further comprising;
   c) contacting said expressed fusion protein with an amino-terminal domain of SUMO, thereby generating a reconstituted SUMO; and
   d) contacting said reconstituted SUMO with a protease specific to SUMO, thereby cleaving said fusion protein such that said protein of interest is produced.

5. The method of claim 4, wherein said amino terminal domain of SUMO of step c) comprises a purification tag, said method further comprising purifying said reconstituted SUMO generated in step c) on a solid support capable of specifically binding said purification tag on said amino terminal domain of SUMO, prior to step d); and said method further comprising:
   e) purifying said protein of interest.

6. The method of claim 5, wherein the purification tag on said amino-terminal domain of SUMO is selected from the group consisting of a polyhistidine tag (6xHis), a polyarginine tag, glutathione-S-transferase (GST), maltose binding protein (MBP), S-tag, influenza virus HA tag, thioredoxin, staphylococcal protein A tag, SEQ ID NO: 140, AviTag epitope, and the c-myc epitope.

7. The method of claim 4, wherein said fusion protein is purified prior to contacting said amino-terminal domain of SUMO by immunoprecipitation with an antibody specific to a protein selected from the group consisting of SUMO (SEQ ID NO: 1) and CTHS (SEQ ID NO: 9).

8. The method of claim 5, wherein said fusion protein comprises at least one purification tag attached to the amino-terminus of the carboxy-terminal domain of SUMO, said method further comprising purifying said fusion protein expressed in step b) on a solid support capable of specifically binding said at least one purification tag on said carboxy-terminal domain of SUMO, prior to said contacting with said amino-terminal domain of said SUMO molecule in c).

9. The method of claim 8, wherein said at least one purification tag on said carboxy-terminal domain of SUMO and said purification tag on said amino-terminal domain of SUMO are selected from the group consisting of a polyhistidine tag (6xHis), a polyarginine tag, glutathione-S-transferase (GST), maltose binding protein (MBP), S-tag, influenza virus HA tag, thioredoxin, staphylococcal protein A tag, SEQ ID NO: 140, AviTag epitope, and the c-myc epitope.

10. The method of claim 8, wherein said at least one purification tag on said carboxy-terminal domain of SUMO and said purification tag on said amino-terminal domain of SUMO are the same.

11. The method of claim 8, wherein said at least one purification tag on said carboxy-terminal domain of SUMO and said purification tag on said amino-terminal domain of SUMO are different.

12. The method of claim 5, wherein said amino-terminal domain of SUMO is attached to said solid support capable of specifically binding said purification tag on said amino-terminal domain of SUMO prior to contacting said purified fusion protein.

13. The method of claim 8, wherein said carboxy-terminal domain of SUMO comprises more than one purification tag and said purification tags on said carboxy-terminal domain of SUMO are different.

14. The method of claim 12, wherein said purification tag on said amino-terminal domain of SUMO is a cysteine residue and said solid support possesses a thiol-reactive group.

15. The method of claim 4, wherein said protease specific to SUMO is Ulp1.

16. The method of claim 4, wherein said protease specific to SUMO further comprises a purification tag.

17. The method of claim 16, wherein said purification on said protease specific to SUMO is the same as said purification tag on said amino-terminal domain of SUMO.

18. The method of claim 16, wherein said purification tag on said protease specific to SUMO is different than said purification tag on said amino-terminal domain of SUMO.

19. The method of claim 16, further comprising contacting said protease to SUMO with a solid support capable of binding said purification tag on said protease specific to SUMO, thereby removing said specific protease from said protein of interest and thereby further purifying said protein of interest.

20. The method of claim 5, further comprising an inhibitor of said protease specific to SUMO during step c).

21. The method of claim 20, wherein said protease inhibitor is selected a salt of heavy metal.

22. The method of claim 21, wherein said heavy metal is selected from the group consisting of zinc and cobalt.

23. The method of claim 20, further comprising removing said protease inhibitor with a metal ion chelator.

24. The method of claim 23, wherein said metal ion chelator is EDTA.

25. The method of claim 5, further comprising eluting said reconstituted SUMO from the solid support prior to contacting with said specific protease.

26. The method of claim 25, wherein said reconstituted SUMO is eluted by the addition of excess said amino terminal domain of SUMO or a derivative thereof.

27. The method of claim 25, wherein said reconstituted SUMO is eluted by changing a characteristic of the solvent selected from the group consisting of pH, salt concentration, chaotropic status, and polarity.

28. A method for generating an altered amino terminus in a protein of interest in a host cell comprising:
  a) providing a nucleic acid sequence encoding said protein of interest;
  b) altering the N-terminal amino acid coding sequence in said nucleic acid;
  c) operably linking a nucleic acid encoding a carboxy-terminal domain of SUNO to said nucleic acid sequence, thereby producing a nucleic acid encoding a fusion protein consisting of said carboxy-terminal domain of SUMO at the amino terminus of the protein of interest, wherein said fusion protein begins with a methionine;
  d) expressing said nucleic acid encoding said fusion protein in a eukaryotic cell; and
  e) expressing a nucleic acid molecule encoding a amino terminal domain of SUMO, thereby producing said protein of interest in said cell, wherein said protein of interest has an altered amino terminus; and wherein said carboxy-terminal domain of SUMO consists of the amino acid sequence from between position 50 and position 62 through position 98 of SEQ ID NO: 1.

29. The method of claim 1, wherein said carboxy-terminal domain of SUMO consists of SEQ ID NO: 9 or SEQ ID NO: 31.

30. A method for enhancing the expression a protein of interest in a host cell comprising:
  a) providing a nucleic acid construct which encodes a fusion protein wherein said construct consists of:
    i) a nucleic acid sequence encoding a carboxy-terminal domain of SUMO, wherein said carboxy-terminal domain of SUMO consists of the amino acid sequence from between position 50 and position 62 through position 98 of SEQ ID NO: 1; and
    ii) a nucleic acid sequence encoding said protein of interest;
  wherein said carboxy-terminal domain of SUMO is attached to the amino-terminus of said protein of interest in the expressed fusion protein, and wherein said fusion protein begins with a methionine;
  b) expressing said nucleic acid construct in said host cell, whereby the presence of said carboxy-terminal domain of SUMO in said fusion protein increases the expression level of said protein of interest in said host cell.

31. The method of claim 30, wherein said host cell is selected from the group consisting of a yeast cell, *E. coil*, a bacterial cell, a mammalian cell, and an insect cell.

32. The method of claim 30, wherein said nucleic acid construct encoding a fusion protein is in a vector.

33. The method as claimed in claim 30, wherein the fusion protein, when expressed, comprises the carboxy-terminal domain of SUMO attached to the amino-terminus of the protein of interest such that cleavage site of SUMO is immediately amino terminal to the protein of interest, said method further comprising;
  c) contacting said expressed fusion protein with an amino-terminal domain of SUMO, thereby generating a reconstituted SUMO; and
  d) contacting said reconstituted SUMO with a protease specific to SUMO, thereby cleaving said fusion protein such that said protein of interest is produced.

34. The method of claim 33, wherein said amino terminal domain of SUMO of step C) comprises a purification tag, said method further comprising purifying said reconstituted SUMO generated in step c) on a solid support capable of specifically binding said purification tag on said amino terminal domain of SUMO, prior to step d); and said method further comprising:
  e) purifying said protein of interest.

35. The method of claim 34, wherein the purification tag on said amino-terminal domain of SUMO is selected from the group consisting of a polyhistidine tag (6xHis), a polyarginine tag, glutathione-S-transferase (GST), maltose binding protein (MBP), Stag, influenza virus HA tag, thioredoxin, staphylococcal protein A tag, SEQ ID NO: 140, AviTag epitope, and the c-myc epitope.

36. The method of claim 33, wherein said fusion protein is purified prior to contacting said amino-terminal domain of SUMO by immunoprecipitation with an antibody specific to a protein selected from the group consisting of SUMO (SEQ ID NO: 1) and OTHS (SEQ ID NO: 9)

37. The method of claim 34, wherein said amino-terminal domain of SUMO is attached to said solid support capable of specifically binding said purification tag on said amino-terminal domain of SUMO prior to contacting said purified fusion protein.

38. The method of claim 37, wherein said purification tag on said amino-terminal domain of SUMO is a cysteine residue and said solid support possesses a thiol-reactive group.

39. The method of claim 33, wherein said protease specific to SUMO is Ulp1.

40. The method of claim 33, wherein said protease specific to SUMO further comprises a purification tag.

41. The method of claim 40, wherein said purification on said protease specific to SUMO is the same as said purification tag on said amino-terminal domain of SUMO.

42. The method of claim 40, wherein said purification tag on said protease specific to SUMO is different than said purification tag on said amino-terminal domain of SUMO.

43. The method of claim 40, further comprising contacting said protease to SUMO with a solid support capable of binding said purification tag on said protease specific to SUMO, thereby removing said specific protease from said protein of interest and thereby further purifying said protein of interest.

44. The method of claim 34, further comprising an inhibitor of said protease specific to SUMO during step c)

45. The method of claim 44, wherein said protease inhibitor is selected a salt of heavy metal.

46. The method of claim 45, wherein said heavy metal is selected from the group consisting of zinc and cobalt.

47. The method of claim 44, further comprising removing said protease inhibitor with a metal ion chelator.

48. The method of claim 47, wherein said metal ion chelator is EDTA.

49. The method of claim 34, further comprising eluting said reconstituted SUMO from the solid support prior to contacting with said specific protease.

50. The method of claim 49, wherein said reconstituted SUMO is eluted by the addition of excess said amino terminal domain of SUMO or a derivative thereof.

51. The method of claim 49, wherein said reconstituted SUMO is eluted by changing a characteristic of the solvent selected from the group consisting of pH, salt concentration, chaotropic status, and polarity.

52. The method of claim 30, wherein said carboxy-terminal domain of SUMO consists of SEQ ID NO: 9 or SEQ ID NO: 31.

* * * * *